US012515029B2

(12) United States Patent

Maaskamp et al.

(10) Patent No.: US 12,515,029 B2
(45) Date of Patent: *Jan. 6, 2026

(54) OBLONG SHAPED MEDICINAL DISPENSER

(71) Applicants: Ryan Maaskamp, Scottsdale, AZ (US); Armand Maaskamp, Scottsdale, AZ (US)

(72) Inventors: Ryan Maaskamp, Scottsdale, AZ (US); Armand Maaskamp, Scottsdale, AZ (US)

(73) Assignee: Ryan Maaskamp, Scottsdale, AZ (US)

(*) Notice: Subject to any disclaimer, the term of this patent is extended or adjusted under 35 U.S.C. 154(b) by 923 days.

This patent is subject to a terminal disclaimer.

(21) Appl. No.: 17/733,815

(22) Filed: Apr. 29, 2022

(65) Prior Publication Data

US 2022/0249816 A1 Aug. 11, 2022

Related U.S. Application Data

(63) Continuation-in-part of application No. 17/379,950, filed on Jul. 19, 2021, now Pat. No. 11,351,297, which is a continuation-in-part of application No. 17/160,295, filed on Jan. 27, 2021, now abandoned, which is a continuation-in-part of application No. 16/714,977, filed on Dec. 16, 2019, now abandoned.

(60) Provisional application No. 62/804,106, filed on Feb. 11, 2019.

(51) Int. Cl.

| | |
|---|---|
| ***A61M 31/00*** | (2006.01) |
| ***A61M 3/02*** | (2006.01) |
| ***A61M 5/32*** | (2006.01) |

(52) U.S. Cl.

CPC ........ *A61M 31/007* (2013.01); *A61M 3/0262* (2013.01); *A61M 5/3291* (2013.01); *A61M 2210/1067* (2013.01); *A61M 2210/1475* (2013.01)

(58) Field of Classification Search

CPC .. A61M 31/00; A61M 31/002; A61M 35/003; A61M 35/00; A61M 2210/1475; A61M 2210/1067

See application file for complete search history.

(56) References Cited

U.S. PATENT DOCUMENTS

| | | | |
|---|---|---|---|
| 3,667,461 | A | 6/1972 | Zamarra |
| 3,894,539 | A | 7/1975 | Tallent |
| 5,695,481 | A | 12/1997 | Heinzelman et al. |
| 7,090,654 | B2 | 8/2006 | Lotito et al. |
| 7,125,394 | B2 | 10/2006 | Berman et al. |
| 7,322,953 | B2 | 1/2008 | Redinger |
| 7,465,295 | B2 | 12/2008 | Bergeron et al. |

(Continued)

*Primary Examiner* — Tasnim Mehjabin Ahmed
(74) *Attorney, Agent, or Firm* — Kenneth Altshuler

(57) ABSTRACT

A medicinal applicator that is defined by a base, a medicinal cream receiving port in the base, and a shaft extending along a shaft axis from the base and terminating at an applicator tip is useful in smearing medicinal cream in a person's colon. There is at least one exit aperture located along a portion of the shaft through which the cream can exit. The medicinal applicator has an unobstructed pathway is in communication with the receiving port and the exit aperture in addition to a stop plate that extends radially from the base delineating the base from the shaft. The shaft's outer shape is defined by an oblong cross section that is uniform along the entire length of the shaft.

20 Claims, 32 Drawing Sheets

(56) References Cited

U.S. PATENT DOCUMENTS

| | | | | |
|---|---|---|---|---|
| 8,092,415 | B2 | 1/2012 | Moehle et al. | |
| 9,132,262 | B2 | 9/2015 | Berman et al. | |
| 11,351,297 | B2 * | 6/2022 | Maaskamp | A61M 3/0279 |
| 2005/0010174 | A1 * | 1/2005 | Berman | A61M 31/00 604/187 |
| 2005/0054996 | A1 | 3/2005 | Gregory | |

* cited by examiner

650

690

Section D-D

Section E-E

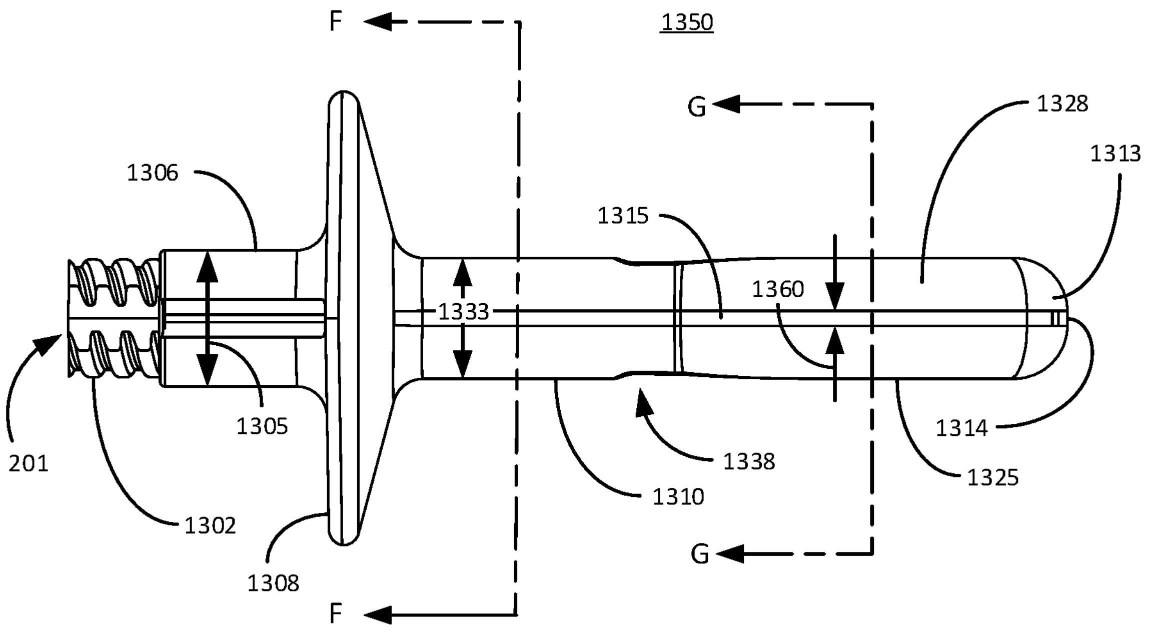
FIG. 17A
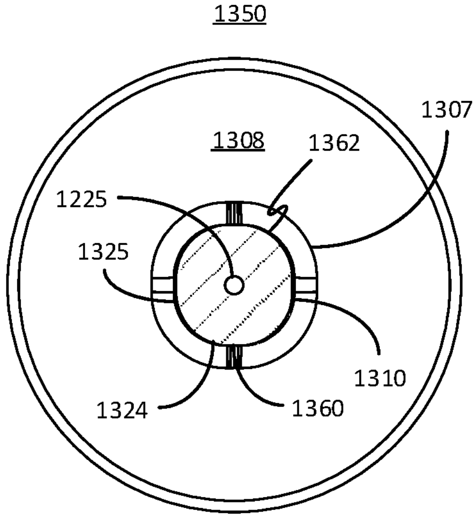
SectionFF
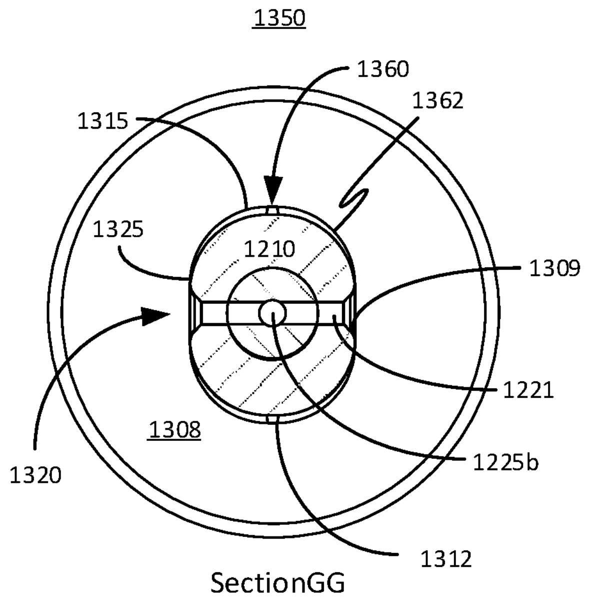
SectionGG
FIG. 17B
FIG. 17C

OBLONG SHAPED MEDICINAL DISPENSER

CROSS-REFERENCE TO RELATED APPLICATIONS

This continuation-in-part application claims priority to and the benefit of U.S. patent application Ser. No. 17/379,950 entitled: PADDLE SHAPED MEDICINAL DISPENSER filed on Jul. 19, 2021, which is a continuation-in-part application claims priority to and the benefit of U.S. patent application Ser. No. 17/160,295 entitled: PADDLE SHAPED MEDICINAL DISPENSER filed on Jan. 27, 2021, which is a continuation-in-part application claiming priority to and the benefit of U.S. patent application Ser. No. 16/714,977 entitled: MEDICINAL DISPENSER filed on Dec. 16, 2019, which claims priority to and the benefit of U.S. provisional Patent Application No. 62/804,106 entitled Medicinal Dispenser, filed on Feb. 11, 2019.

FIELD OF THE INVENTION

The present embodiments are generally directed to a medicinal dispenser probe for more uniformly spreading a coat of medicinal cream within the contours of an anal or vaginal canal.

DESCRIPTION OF RELATED ART

Certain medical ailments afflict regions of human anal and vaginal canals. In some instances, these medical ailments (such as infections, viral related blisters, cancers, fissures or some other pathological pain or disease) are treatable with a medicinal cream when applied to the surface tissue of the anal and/or vaginal canal. Presently, such medicinal creams are often applied manually in the anal or vaginal canal by spreading the cream on the canal surface via a finger. One problem with using a finger to spread the medicinal cream is that it often requires the help of a second person because it is difficult to auto apply (i.e., self-apply) the medicinal cream. Accordingly, applicators for dispensing a medicinal cream to these canals exist so that people can independently apply (auto apply) medicinal cream to themselves (their anal or vaginal canal) without the help of a second person.

FIG. 1A, in view of FIG. 1B, illustratively depicts a line drawing of a prior art applicator for auto application of a medicinal substance in an anal canal. As shown, the applicator 100 possesses a handle 106, a shaft 110 that extends from the handle 106 and terminates in a rounded dome 104 at the distal end of the applicator 100. As shown, the rounded dome 104 has a diameter that never exceeds the diameter of the shaft 110 in order to facilitate easy insertion in a human anus. The proximal end 102 of the applicator 100 is adapted to receive a medicinal cream (or other viscous material/s) by way of an aperture 101. There is an unobstructed pathway 121 (see FIG. 1B) between the aperture and two slots 120, the two slots are axially located along the length of the shaft 110. As a note, the cross-section of the outer physical surface 119 (as opposed to the phantom circular shape 117) does not extend beyond, or outside the boundary of, the circular shape 161 (FIG. 1B). The applicator 100 is universal to any natural opening of the anatomy of a human body including vaginal openings and anal openings. Accordingly, the applicator 100 is nonspecific to any particular anatomy of any specific opening of a human body.

In practice, the applicator 100 can be gripped via the handle 106, inserted through the anus and into the anal canal whereby medicinal cream can be forced through the aperture 101 and out through the slots 120. While the medicinal cream is being pushed out of the slots when the shaft is deployed in the human anal canal, a person can rotate the shaft 110 by way of turning the handle 106 to coat the surface of the anal canal. Because the applicator 100 is not specific to any particular anatomy of any specific opening of a human body, the cross-section of the shaft 110 maps to a circular profile or shape 161.

FIG. 1B illustratively depicts a line drawing of the cross-section of the prior art applicator shaft along the cut-line A-A 160 of the shaft 110. As shown, the shaft 110 has two openings 120 through which the medicinal cream can be expelled from the applicator 100. As shown, the cross-section of the outer surface of the shaft 110 at the longitudinal slot 120 maps to a circular shape 161. Moreover, the cross-section of essentially any location along the shaft 110 maps to a circular shape whereby the physical surface at the cross-section is greater than 50% (the physical surface depicted by the shaded regions 110 of the cross-section 160, mapped projected circular region depicted by the dashed circle 161). As previously mentioned, because the shaft 110 maps to a circular shape, the applicator 100 is nonspecific to any particular anatomy of any specific opening of a human body which makes the applicator 100 deficient for applying medicinal cream to any specific contours of an orifice, such as in an anal canal, for example. In other words, the circular shape and size of the shaft makes it difficult to impossible to reach into folds within an anal canal.

Hence, with regards to an anal canal, a human finger is well adapted to spread medicinal cream in the contours within the anal canal thereby providing good coverage of the medicinal cream. The downside to applying medicinal cream using a finger is that the recipient typically needs a partner to help (i.e., the partner's finger). The applicator 100 provides the benefit of auto application, however, it is deficient in applying medicinal cream to the specific contours of the anal canal (i.e., the applicator 100 does not provide good coverage of the medicinal cream to the entire surface of the anal canal).

It is to innovations related to this subject matter that the claimed invention is generally directed.

SUMMARY OF THE INVENTION

The present embodiments are generally directed to a medicinal dispenser probe for auto application to improve uniformly spreading a coat of medicinal cream within the contours of an anal or vaginal canal.

Certain embodiments contemplate a medicinal applicator generally comprising a base, a medicinal cream receiving port in the base and a shaft extending along a shaft axis from the base and terminating at an applicator cap. The shaft having a cross-section that is essentially a rectangle with upper rounded corners that extend from rectangle sides and the upper rounded corners connect at the leading edge via an uninterrupted upper uninterrupted linear extension and lower rounded corners that extend from the rectangle sides and connect at the trailing edge via an uninterrupted lower uninterrupted linear extension. The upper uninterrupted linear extension resides along a shaft leading edge and the lower uninterrupted linear extension resides along a shaft trailing edge. The leading edge is diametrically opposed to the trailing edge. There is at least one exit aperture located in one of the rectangle sides that is in communication with a receiving port via an unobstructed pathway.

Yet another embodiment of the present invention envisions an applicator for medicinal cream comprising a rectal/ vaginal shaft separated from a handle via a stop plate. The shaft defined by a shaft axis that extends through the center of the handle to a shaft cap to where the shaft terminates distally. The shaft further defined by a leading edge diametrically opposed to a trailing edge. An unobstructed pathway is in communication with a receiving port in the handle and an exit aperture in the shaft. The shaft's cross-section is oblong shaped and the cross-section is essentially uniform along the entire length of the shaft.

Still yet another embodiment contemplates a method for applying medicinal cream. The method can start with providing a medicinal applicator that includes a shaft separated from a handle via a stop plate. A cross-section of the shaft is essentially oblong shaped along a substantial portion of the shaft length. The shaft is defined by a leading edge and a trailing edge that are diametrically opposed wherein the leading edge mirrors the trailing edge. The method further includes attaching a tube or syringe, that contains medicinal cream, to an attachment zone at a proximal end of the handle. The shaft can be inserted into an anal or a vaginal cavity (cavity) in a neutral position, which defines a neutral axis. While the medicinal applicator is in the cavity, injecting medicinal cream via an exit aperture that is located along the shaft sides between the shaft apexes. The cream that is injected in the cavity can be dispersed by rotating the shaft about the neutral axis and/or tipping the shaft at an angle of greater than 10° from the neutral axis. The shaft can be moved back and forth and/or clockwise and counter clockwise.

BRIEF DESCRIPTION OF THE DRAWINGS

FIG. 17A is a top view line drawing of the medicinal applicator consistent with embodiments of the present invention;

FIGS. 17B and 17C are line drawings of cross-sections of the shaft at the corresponding cross-section cut lines FF and GG of FIG. 17A consistent with embodiments of the present invention;

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving similar uses of anal probes for use in spreading medicinal cream. In what follows, similar or identical structures may (and may not) be identified using identical callouts.

Described herein includes embodiments of an anal or vaginal medicinal applicator that, in certain configurations, possess an oblong cross-sectional shaped shaft, or probe. The oblong shaped shaft enhances the ability of the shaft to more easily be made to move into the folds and contours in the anal canal thereby more evenly spreading medicinal cream on the full surface of the anal canal. Certain other embodiments include an enlarged dome that helps to keep the medicinal cream in the anal canal by blocking the cream from spreading beyond the distal end of the anal medicinal applicator up into and beyond the rectum. Other embodiments include a medicine blocking ring on the shaft near the handle that prevents the medicinal cream from flowing out of the anus when the anal medicinal applicator is being used (i.e., deployed). The anal medicinal applicator generally comprises a base, a medicinal cream receiving port in the base, a shaft and at least one longitudinal slot through which an uninterrupted passageway extends. Medicinal cream can be made to flow through the uninterrupted passageway and out through the longitudinal slot/s to apply the medicinal cream to needed areas within an anal canal when the medicinal applicator is deployed. Certain embodiments envision the outer surface of the shaft not mapping to a circular shape (i.e., less than 50% of the circular outer surface maps to a circle) to improve spreading the medicinal cream.

Figure 1A:
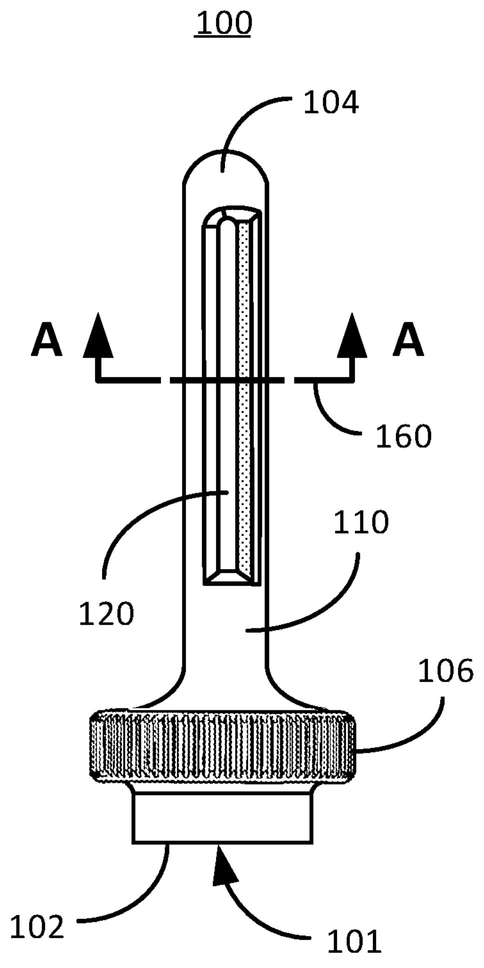
FIG. 1A illustratively depicts a line drawing of a prior art applicator for auto application of a medicinal substance in an anal canal.
Figure 1B:
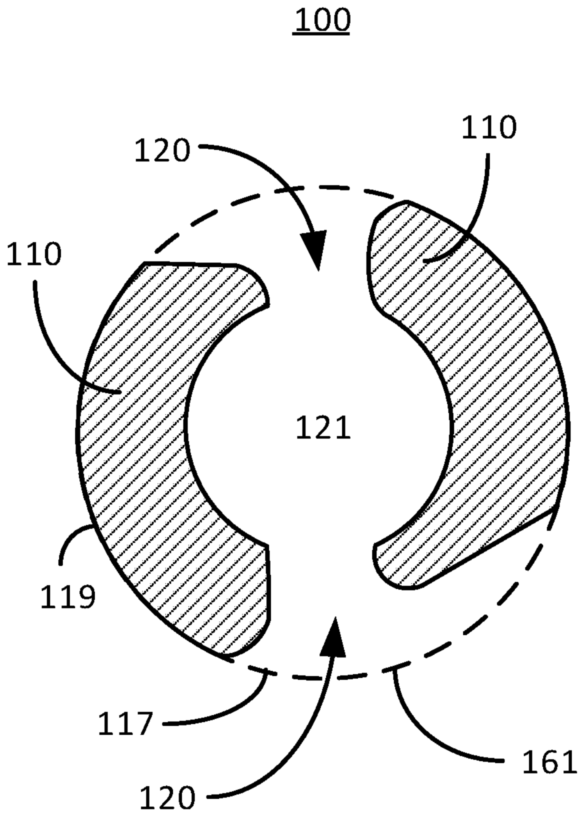
FIG. 1B Prior Art
FIG. 1B illustratively depicts a line drawing of the cross-section of the prior art applicator shaft along the cut-line A-A of the shaft.
Figure 2A:
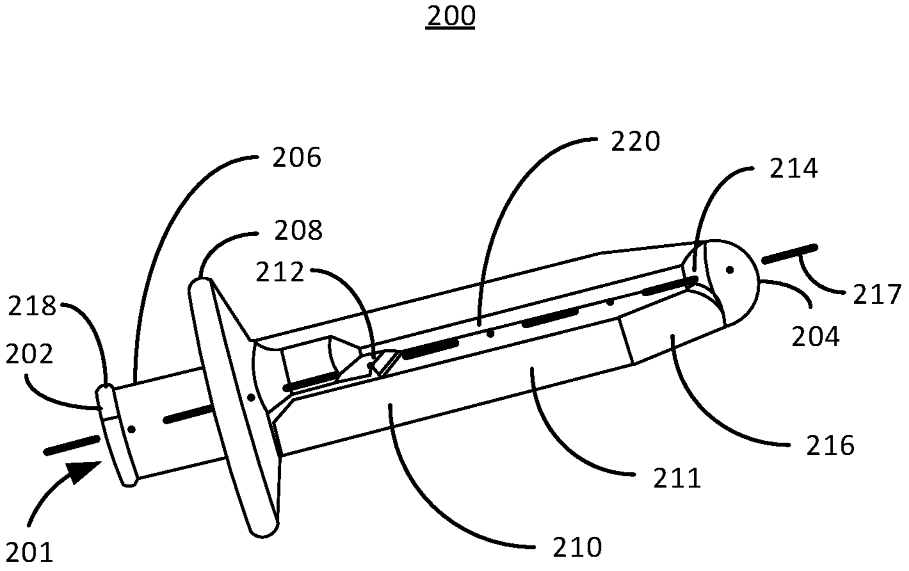
FIGS. 2A-2D illustratively depict different drawing views of an anal medicinal applicator embodiment 200 consistent with embodiments of the present invention.

FIGS. 2A-2D illustratively depict different drawing views of an anal medicinal applicator embodiment 200 consistent with embodiments of the present invention. FIG. 2A shows a three-quarter side view illustration of the anal medicinal applicator 200 generally comprising a base 206 and an anal shaft 210 (or just shaft) separated by an anus abutting stop plate 208, which in this embodiment is a flange. More specifically, the anal medicinal applicator 200 comprises a base 206 defining a proximal end 202 and a shaft 210 that extends along a shaft axis 217 from the base 206 and terminates at a distal end 204 (also referred to herein as an anal tip because when deployed, or otherwise used, it resides inside of an anal canal 804). In the present embodiment, the region distal to the anus abutting stop plate 208 (and anus contact surface 222) is defined as the anal cavity region of the anal medicinal applicator 200. In other words, the anal cavity region consists of the anal shaft 210 and the anal tip 204 in this embodiment. The base 206 is essentially a cylinder that possesses a syringe connector lip 218 at the proximal end 202. The connector lip 218 is adapted to receive and lock in place a medicinal cream dispensing syringe 700 (shown in FIG. 7). The proximal end 202 further comprises a medicinal cream receiving port 201, which is essentially an aperture leading into a pathway 225 (shown in FIG. 3A) that passes through the base 206 and into the shaft 210, discussed in more detail infra. Certain embodiments further envision the base portion 206 used as a handle that can be grasped by a human hand to hold and manipulate the anal medicinal applicator 200. The anus abutting stop plate (or just stop plate) 208 can possess a sloped anus contact surface 222 that transitions into the shaft 210. The sloped anus contact surface 222 butts up against the anus (not shown) when the anal medicinal applicator 200 is inserted in the anal canal. The stop plate 208 extends radially from the axis 217 beyond the shaft 210 and essentially confines only the elements (shaft 210, dome 214, etc.) of the anal medicinal applicator 200 that are distal to the sloped surface 222 as being capable of going inside of an anal canal. In other words, the stop plate 208 prevents the base portion 206 from being pushed inside of the anal canal when the anus abutting stop plate 208 is pressed normally against the anus. Accordingly, when in normal use, the anus abutting stop plate 208 is essentially incapable of being pushed into an anal canal. Exceptions to normal use, and hence, "essentially incapable" is defined as situations when a user misuses the anal medicinal applicator 200 by intentionally pressing the stop plate 208 into their (or someone else's) anus overcoming the functionality of the stop plate 208 by way of excessive force.

With more detail to the shaft portion 210, which in certain embodiments is envisioned to be between 2-5 inches long, a pair of opposing longitudinal dispensing slots (or just longitudinal slot/s) 220 extend along a portion of the shaft 210 in-line (in line?) with the axis 217 as shown. The longitudinal slots 220 essentially serve as exit apertures that dispense medicinal cream, or some other viscous material, in an anal canal. Here, the shaft 210 has a narrowing tapered transition 216 that terminates at the dome 214 that defines the anal tip distal end 204 of the anal medicinal applicator 200. In this embodiment, the dome 214 is essentially a spherical knob at the anal tip 204 of the shaft 210. The narrowing tapered transition embodiment 216 is advantageous for easy insertion into an anus and into the anal canal.

Figure 2B:
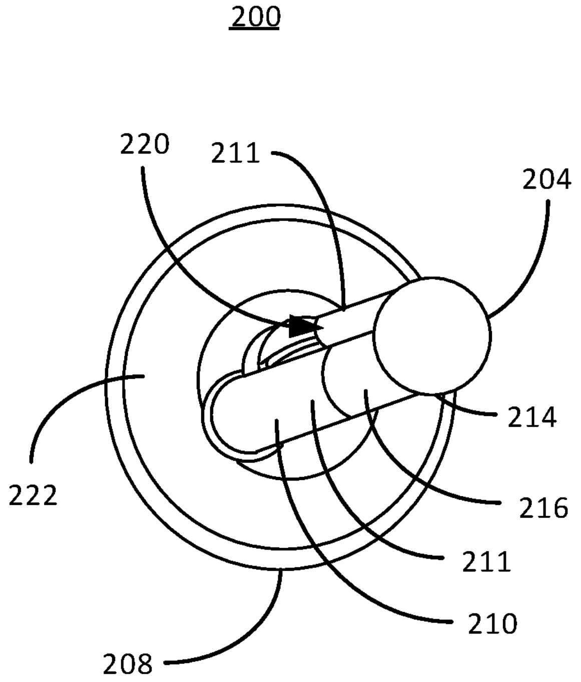

FIG. 2B is a three-quarter front view illustration of the anal medicinal applicator 200 consistent with embodiments of the present invention. As illustratively shown, the shaft 210 comprises two lobes 211 on either side of the longitudinal slots 220. The lobes 211 improve spreading the medicinal cream expelled through the longitudinal slots 220 by more easily reaching into the folds and contours of the anal canal. The stop plate 208 is blocking the view of the base 206. As can be more clearly seen in this figure, the stop plate 208 extends essentially radially from the axis 217 beyond the shaft 210, thereby butting up against an anus when the anal medicinal applicator 200 is inserted in an anal canal.

Figure 2C:
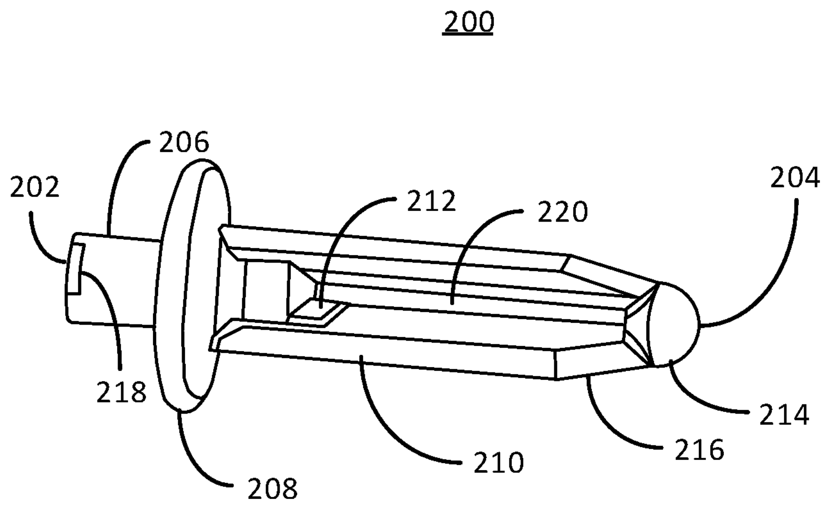

FIG. 2C it is a slightly tilted side view illustration of the anal medicinal applicator 200 consistent with embodiments of the present invention. The syringe connector lip 218 at the proximal end 202 of the base 206 is in view to better show the structure adapted to lock in place with a receiving channel (shown in FIG. 7) associated with a syringe. Also better shown is the longitudinal slot/s 220, which extends along the length of the shaft 210. A spreading plate 212 improves the distribution of the medicinal cream when expelled from the longitudinal slot 220 while the anal medicinal applicator 200 is deployed in an anal canal.

Figure 2D:
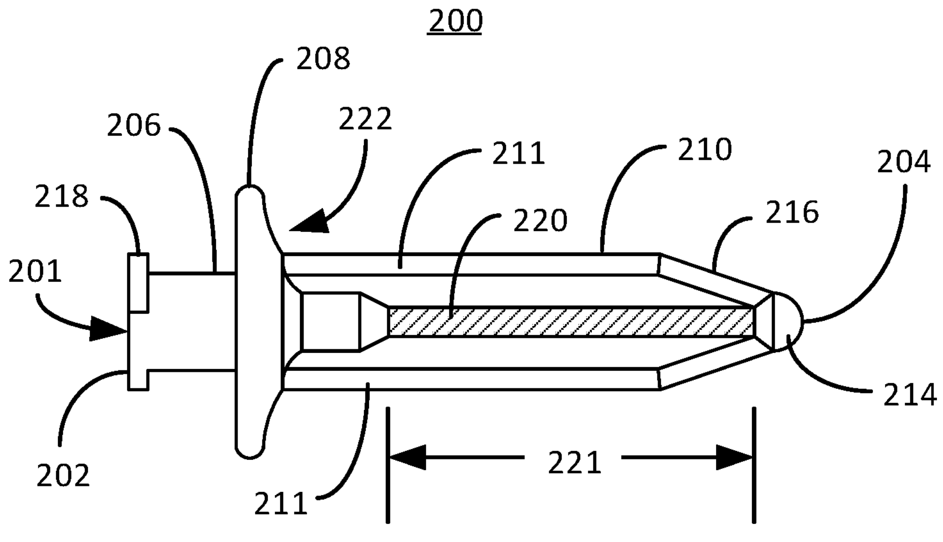

FIG. 2D illustratively depicts a side view line drawing of the anal medicinal applicator 200 consistent with embodiments of the present invention. As shown, the longitudinal slot 220 is hashed to indicate that it is an aperture through which medicinal cream can exit (i.e., be expelled) from the shaft 210. The longitudinal slot length 221 (which in this case is defined as extending along the axis 217) is approximately 80% the shaft length, in this embodiment. The lobes 211 of the shaft 210, the receiving port location 201, the proximal end 202 of the base 206, and the sloped surface 222 of the stop plate 208 are all labeled for reference.

Figure 3A:
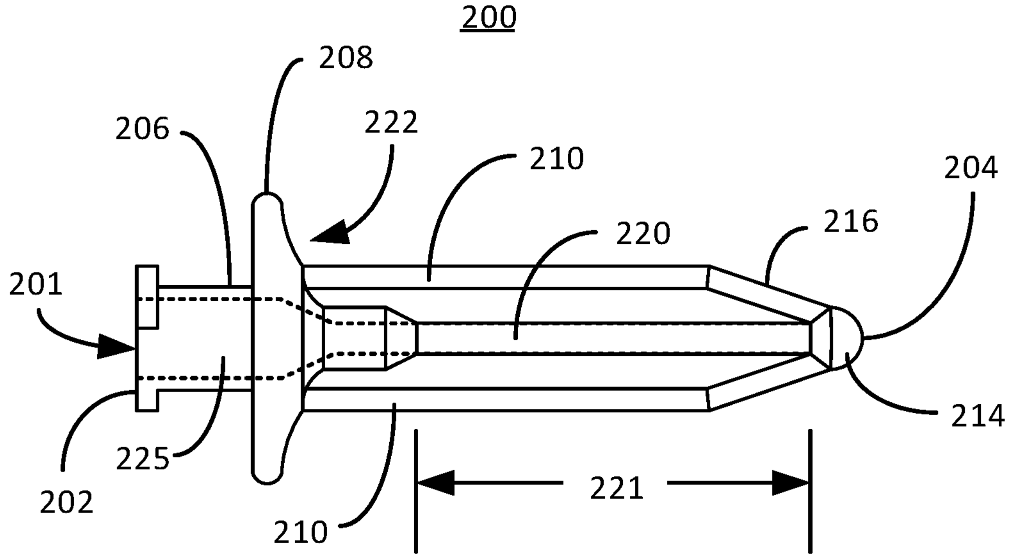
FIGS. 3A and 3B illustratively depict a side view of the anal medicinal applicator with detail to the unobstructed pathway system with embodiments of the present invention.
Figure 3B:
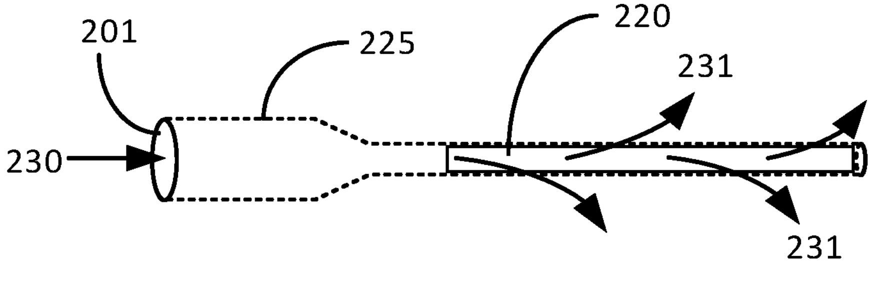

FIGS. 3A and 3B illustratively depict a side view of the anal medicinal applicator 200 with the unobstructed pathway system 225 detailed consistent with embodiments of the present invention. Similar to FIG. 2D, the side view of the anal medicinal applicator 200 is depicted with the unobstructed pathway 225 shown by dotted lines. The unobstructed pathway 225 possesses an inlet, or receiving, port 201 in the proximal end 202 depicted by arrow 201. The inlet port 201 is adapted to receive medicinal cream from a syringe or other cream (viscous material) dispensing device. The inlet port 201 is further adapted to cooperate with an outlet port of a syringe (shown in FIG. 7) by way of the connector lip 218 or some other mechanical configuration capable of locking, or otherwise forming, a cooperating relationship between the anal medicinal applicator 200 and the syringe. The unobstructed pathway 225 passes through the hub of the base 206, through a passageway in the stop plate 208, and out through the longitudinal dispensing slot/s 220. Certain embodiments contemplate the unobstructed pathway 225 symmetrically in line with the axis 217.

FIG. 3B illustratively depicts the unobstructed pathway 225 of FIG. 3A including the flow path for medicinal cream. The medicinal cream enters in the inlet/receiving port 201, as shown by the arrow 230, and out the at least one longitudinal dispensing slot 220 (which is part of the unobstructed pathway 225), as shown by the curved arrows 231. In practice, the flow of the medicinal cream (as illustratively depicted by the arrows 230 and 231) dispenses into the anal canal when the anal medicinal applicator 200 is deployed in the anal canal accordingly.

Figure 4A:
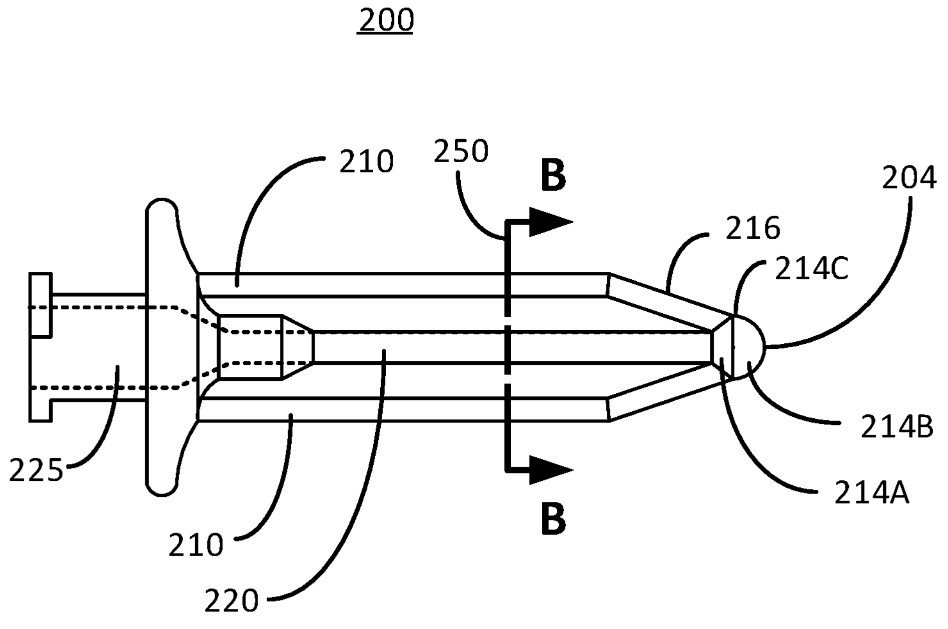
FIG. 4A-4C illustratively depicts cross-sectional line drawings of the anal medicinal applicator in accordance with embodiments of the present invention.
Figure 4B:
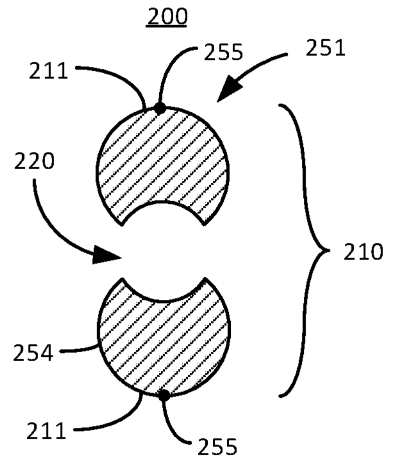
Figure 4C:
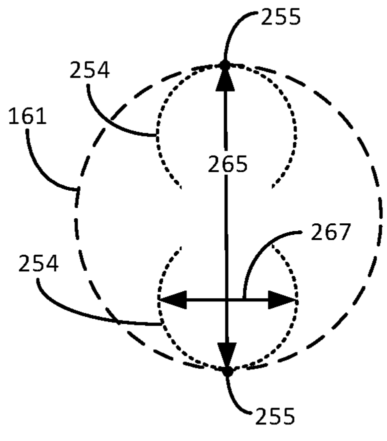

FIG. 4A-4C illustratively depict cross-sectional line drawings of the anal medicinal applicator 200 in accordance with embodiments of the present invention. FIG. 4A shows the side view of the anal medicinal applicator 200 of FIG. 3A, but with a cross-sectional cut-line 250 B-B through the middle of the shaft 210 at the two lobes 211. Note, in this embodiment the dome 214 is smaller in diameter of the shaft 210 (the largest diameter of the shaft 210 as measured orthogonally from the axis 217). The largest diameter of this dome embodiment 214 is at the dome midpoint 214C. The dome 214 extends from a proximal dome section 214A at the tapered shaft 216 and terminates at a dome anal tip 214B.

FIG. 4B illustratively depicts the cross-section 251 of the two lobes 211 of the shaft 210 at the cut-line 250 B-B. A true cross-section would reveal all of the elements visible below the cut-line 250 B-B, however, in the interest of clarity, only the elements at the cut-line 250 B-B are shown. As is readily apparent, the cross-section 251 of the outer surface (out profile) 254 of the two lobes 211, that comprise the shaft 210 at the longitudinal slot 220, do not map (overall) to a circular shape 161. Even though one might argue that two apex points 255 could conceivably define a circular shape, embodiments of the present invention do not consider two apex points 255 as mapping to a circular shape within the scope and spirit of the present invention.

FIG. 4C illustratively depicts the outer profile of the outer surface of the shaft 254 (shown here as the dotted lines) not mapping to a circular outer profile shape 161 (shown here as the dashed lines). The outer profile 254 is defined by the orthogonal cross-section 250 (i.e., the cross-section at 90° to the shaft axis 217) of the shaft 210 at, or otherwise over the location of, the longitudinal slots 220. The duel lobed anal medical applicator 200 is oblong shaped defined by a major axis 265 that is longer than a minor axis 267, the minor axis 267 being the lobe width at a right angle to the major axis 265 in this embodiment.

Figure 5A:
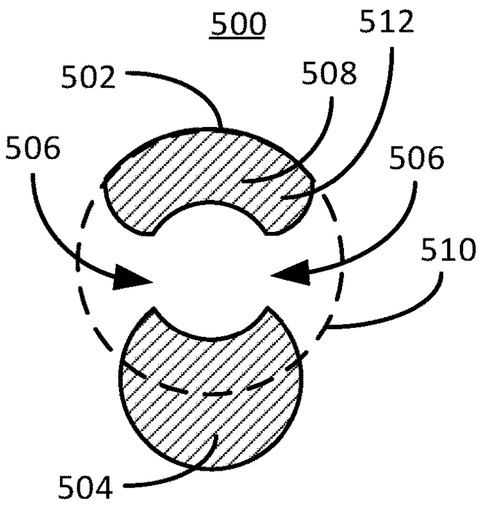
FIGS. 5A-5C illustratively depict line drawings of cross-sections of different shaft shapes of anal medicinal applicator embodiments consistent with embodiments of the present invention.
Figure 5B:
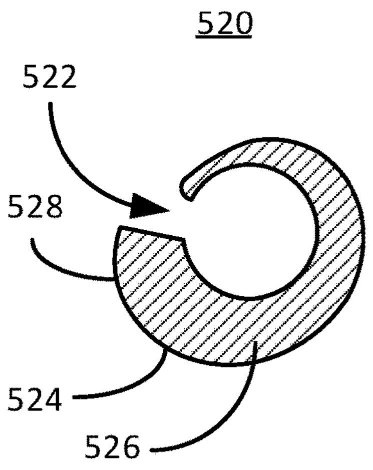
Figure 5C:
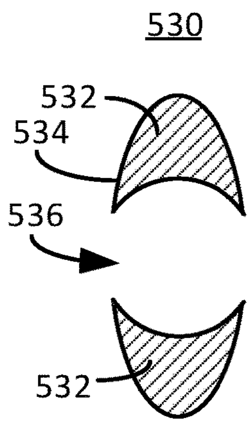

FIGS. 5A-5C illustratively depict line drawings of cross-sections of various shaft species shapes of anal medicinal applicator embodiments consistent with embodiments of the present invention. FIG. 5A shows yet another embodiment of a cross-section 508 of a shaft 502 (taken at 90° over the axis 217 running through the center of the shaft 502) at a pair of longitudinal slots 506 of an anal medicinal applicator embodiment 500. Here, a first lobe 512 has an outer surface (physical outer surface) that maps to the circular shape 510, and a second lobe 504 that does not map to the circular shape 510. FIG. 5B shows another embodiment of a cross-section 526 of a shaft 528 (taken at 90° over axis 217 running through the center of the shaft 528) at a single longitudinal slot 522 of an anal medicinal applicator embodiment 520. Here, the outer cross-sectional shape 524 is a spiral. FIG. 5C illustratively depicts another oblong shaped anal medicinal applicator 530 embodiment as viewed in cross-section 534 at a pair of longitudinal slots 536. The outer shape of the anal medicinal applicator embodiment 530 maps to an ellipse, as shown by the two lobes 532.

Figure 6A:
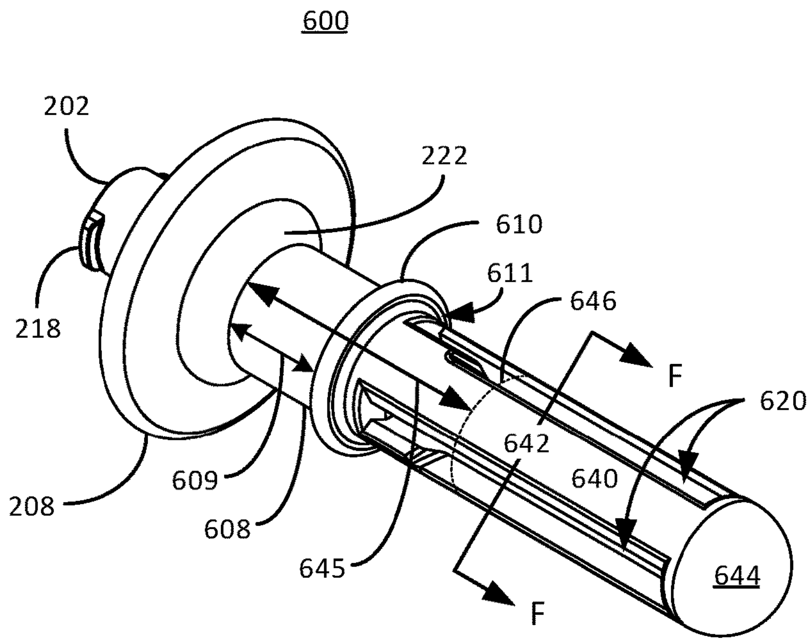
FIGS. 6A-6F illustratively depict line drawings of anal medicinal applicator embodiment using a medicine blocking ring consistent with embodiments of the present invention.

FIG. 6A illustratively depicts an isometric line drawing of an anal medicinal applicator embodiment 600 consistent with embodiments of the present invention. Here, the shaft 640 maps to a circular outer profile shape 161. The anal shaft 640 further possesses three longitudinal slots 620 (two of which are shown in this figure). An anal medicine blocking ring 610 is disposed along a lower half 646 of the anal shaft 640 (depicted by the double-headed arrow 645 extending from the sloped anal contact surface 222 of the anus abutting stop plate 208 to the dotted line 646). The anal medicinal blocking ring 610 extends essentially radially outward from the anal shaft 640 to help prevent medicinal cream 710 from back-flowing out of the anus 820 when dispensed in the anal canal 804 (via the longitudinal slots 620). In the present embodiment, the anal medicine blocking ring 610 terminates 611 just shy (i.e., less than one-half a centimeter in this embodiment) of the longitudinal slots 620, as shown. A proximal shaft region 608 is devoid of any slots or openings and is defined as the distance 609 between the anal medicine blocking ring 610 and the sloped anal contact surface 222. In the present embodiment, the proximal shaft region 608 is approximately the same diameter as the rest of the anal shaft 640. Some embodiments envision the anal medicine blocking ring 610 fixedly attached to, or integrated as, a molded feature with the anal shaft 640. Certain other embodiments envision the distance 609 of the anal medicine blocking ring 610 located at least one centimeter from the anus contact surface 222. Some embodiments envision the anal medicine blocking ring 610 extending as far as three centimeters distance 609 from the anus abutting stop plate 208.

Figure 6B:
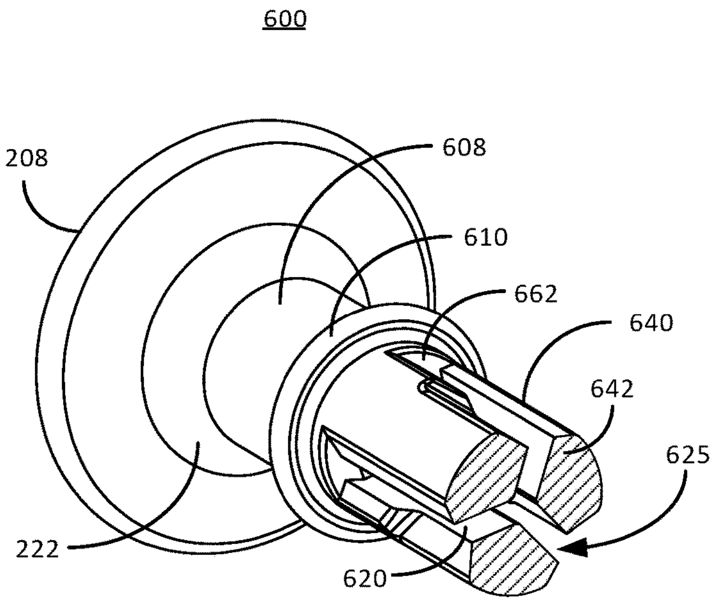
Figure 6C:
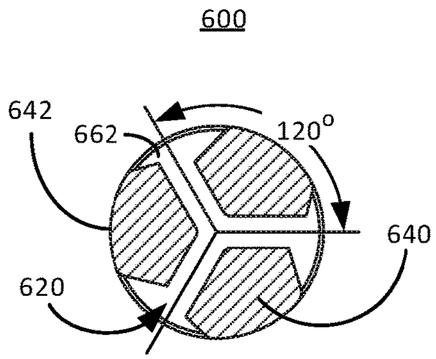

FIG. 6B is an isometric line drawing cross-sectional view 642 of the anal medicinal applicator 600 consistent with embodiments of the present invention. The cross-section 642 is taken orthogonally (at a right angle) across the longitudinal slots 620, as shown in FIG. 6A. The uninterrupted pathway 625 exits through the three longitudinal slots 620. As shown in the front facing view of the cross-section 642 of FIG. 6C, the longitudinal slots 620 are equally positioned along the anal shaft 640, 120° apart.

Figure 6D:
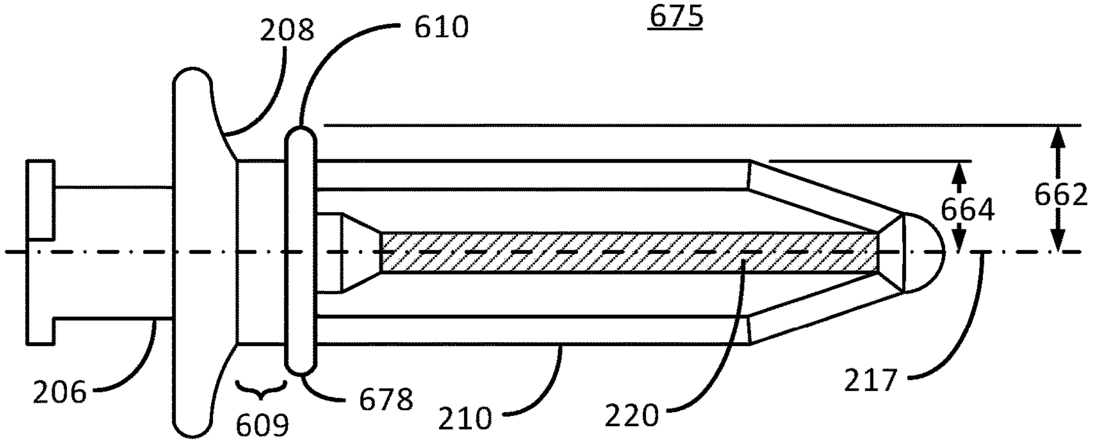

FIG. 6D is a side view line drawing of a dual-longitudinal slotted anal medicinal applicator 675 embodiment with the anal medicine blocking ring 610 located at the proximal shaft region distance 609 from the anus abutting stop plate 208. In this embodiment, the ring radius 662 is larger than the shaft radius 664 thereby reducing medicinal cream 710 from back-flowing out of the anus 820 when dispensed in the anal canal 804. Certain embodiments envision the ring radius 662 being at least one-quarter of a centimeter larger than the shaft radius 664, while other embodiments envision the ring radius 662 ranging between one-quarter of a centimeter to three-quarters of a centimeter larger than the shaft radius 664. Also shown here, the anal medicine blocking ring 610 has a rounded outer edge 678 to improve comfort of the ring inside of an anal canal.

Figure 6E:
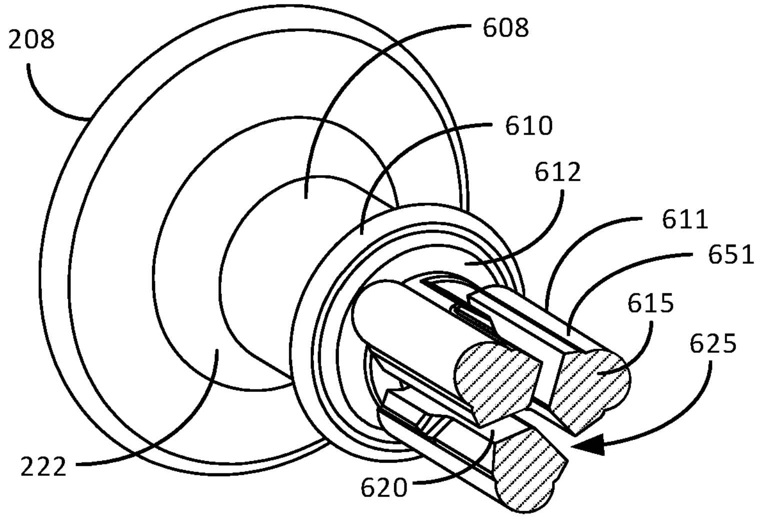

FIG. 6E is an isometric line drawing cross-sectional view 615 of an anal medicinal applicator embodiment 650 consistent with embodiments of the present invention. The cross-section 615 is taken orthogonally (at a right angle) across the longitudinal slots 620. As shown from this perspective, the uninterrupted pathway 625 exits along the three longitudinal slots 620. In this embodiment, the longitudinal slots 620 are equally positioned along the anal shaft 651, 120° apart. This anal medicinal applicator 650 comprises three longitudinal slots 620 in the anal shaft 651 wherein the outer profile 254 of the anal shaft 651 does not map to a circular outer profile shape 161. Rather, the anal shaft 651 is generally comprised of three protruding bulbous lobes 611. As discussed in conjunction with the anal medical applicator 200, the lobes 611 provide enhancements to spread medicinal cream 710 inside of an anal canal 804. In this embodiment, the bulbous lobes 611 extend distally from a flat surface 612 approximately where the anal medicine blocking ring 610 is disposed (between zero centimeters and 1 cm from anus contact surface 222).

Figure 6F:
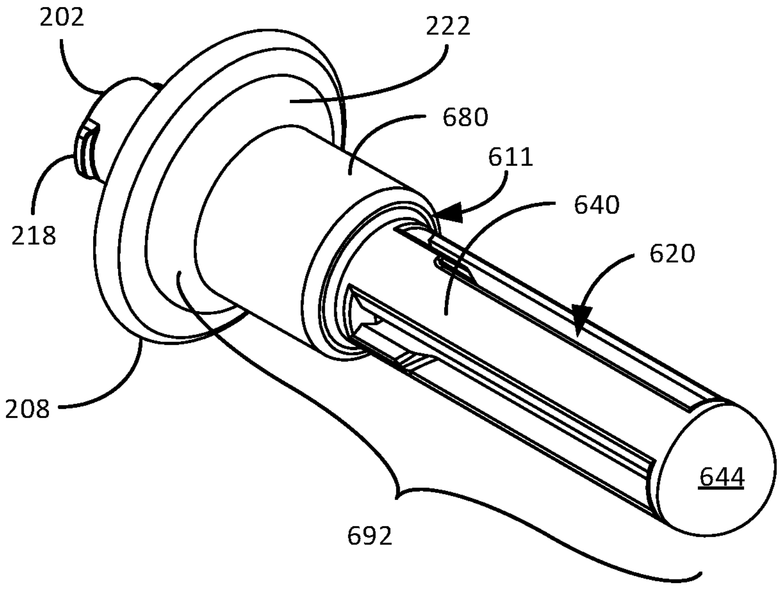

FIG. 6F is an isometric line drawing of an anal medicinal applicator embodiment 690 consistent with embodiments of the present invention. Here, the anal medicine blocking ring 680 extends from the anus abutting stop plate 208 (and more specifically, from the anus contact surface 222) to a terminating ring edge 611 at a distal location of the anal medicinal blocking ring 680. In the present embodiment, the anal medicine blocking ring 680 is essentially a cylinder that has a larger diameter than the anal shaft 640. It is envisioned in this embodiment that the anal medicinal blocking ring 680, the anal shaft 640 and the anal tip 644 comprise an anal canal region 692, while other embodiments envision the anal canal region 692 consisting of the anal medicinal blocking ring 680, the anal shaft 640 and the anal tip 644.

Figure 7A:
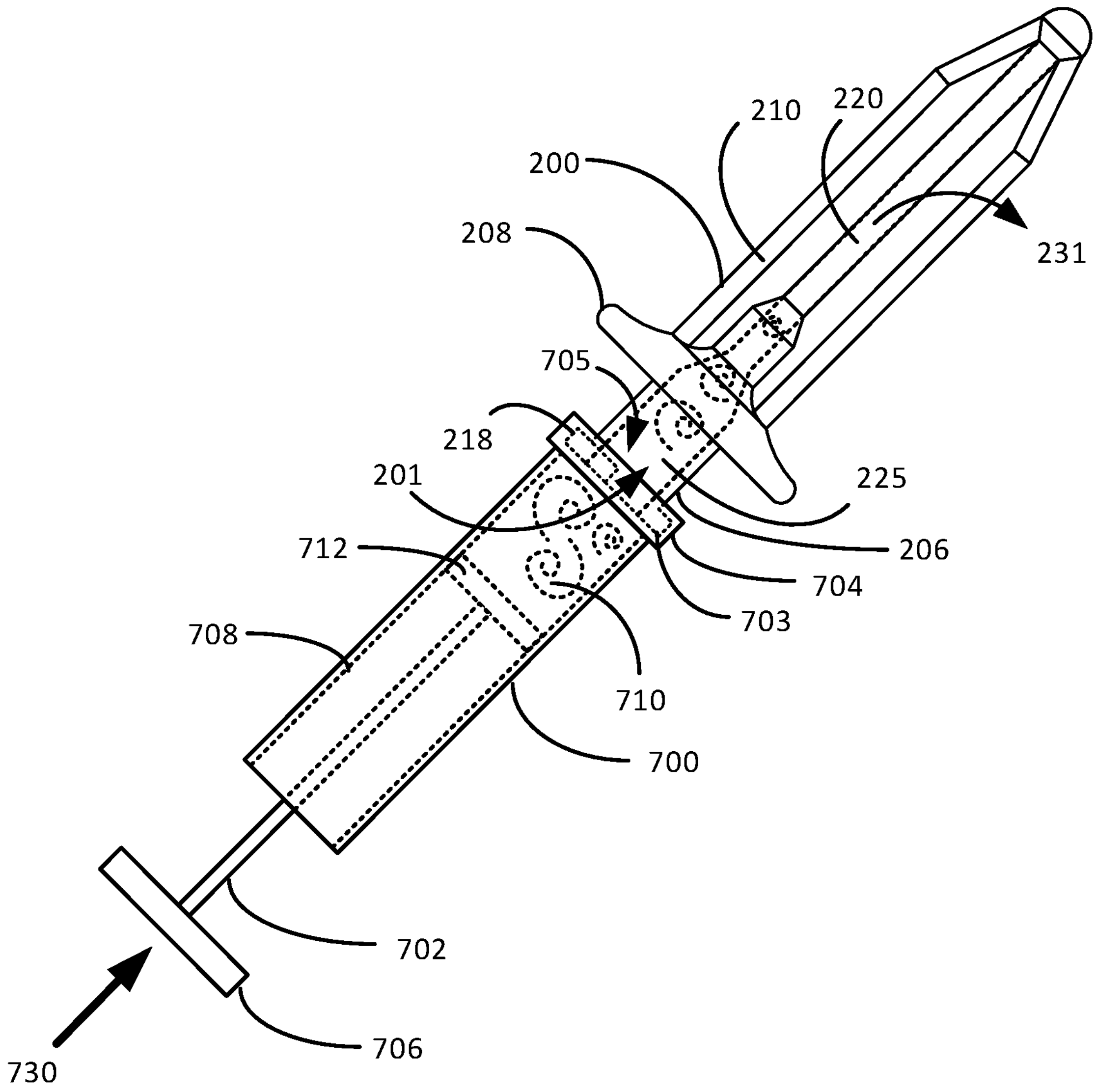
FIG. 7A illustratively depicts a drawing of an anal medicinal applicator cooperating with a syringe consistent with embodiments of the present invention.

FIG. 7A illustratively depicts a line drawing of an anal medicinal applicator cooperating with a syringe consistent with embodiments of the present invention. The anal medicinal applicator 200 is fixedly attached with a syringe 700 by way of the connector lip 218 and receiving channel 703 inside of an attachment sleeve 704, which is located at the exit port 705 of the syringe 700. In this example, the syringe 700 is partially depressed, i.e., the plunger seal 712 is displaced partway down barrel/tube 708. In practice, a person squirting/dispensing medicinal cream 710 either into their anal canal (self-administering) or someone else's anal canal will grip the syringe barrel 708 and depress the plunger top 706 in the direction of arrow 730. By depressing the plunger top 706, the plunger piston 702 physically pushes the medicinal cream 710, via the plunger seal 712, through the unobstructed pathway 225 and out through the longitudinal slot/s 220 and into the anal canal, as shown by arrow 231.

Figure 7B:
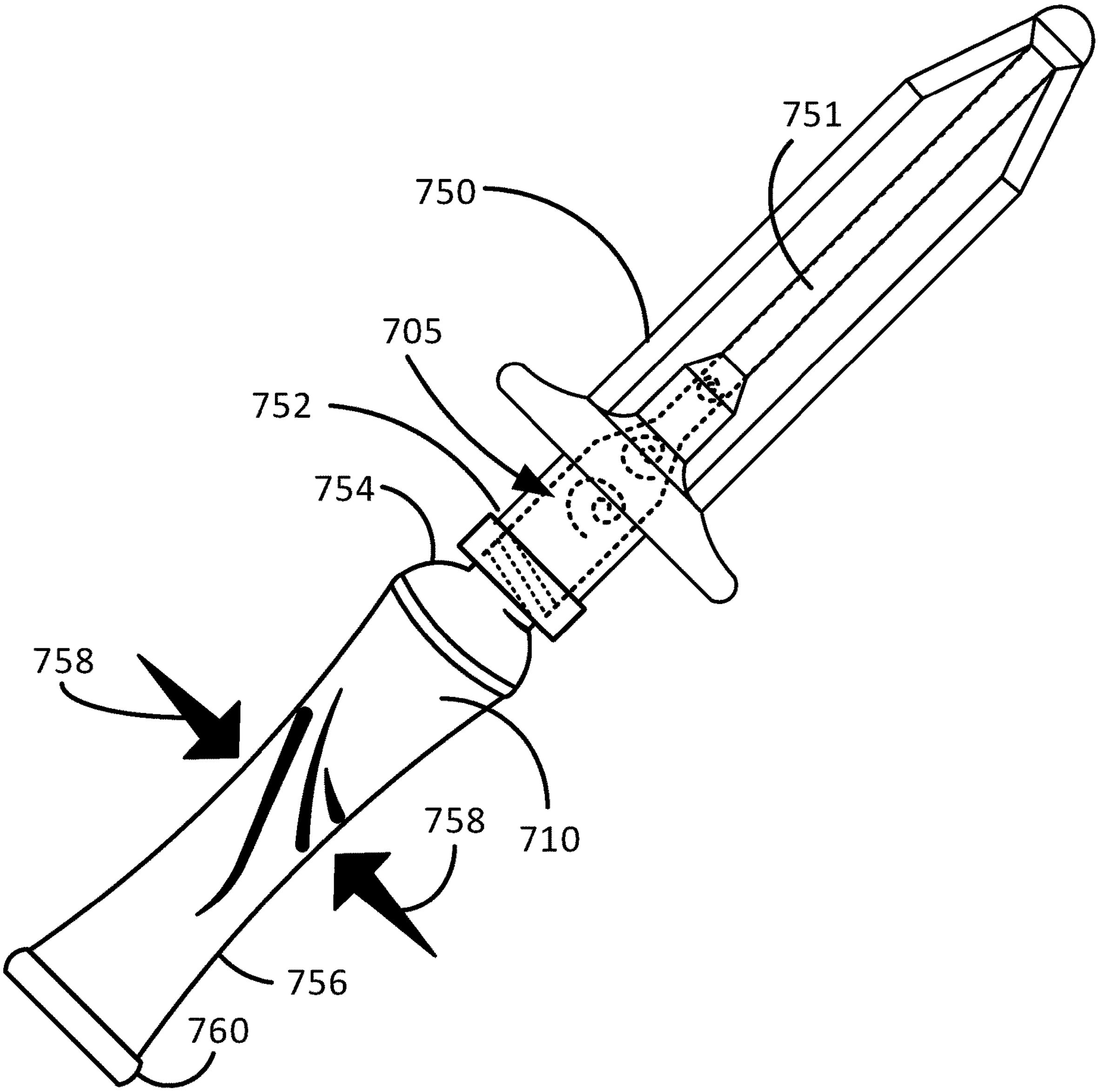
FIG. 7B illustratively depicts a drawing of an anal medicinal applicator cooperating with an optional deployment device consistent with embodiments of the present invention.

FIG. 7B illustratively depicts a drawing of an anal medicinal applicator cooperating with an optional deployment device consistent with embodiments of the present invention. As shown, an embodiment of an anal medicinal applicator 750 (which is similar to the anal medicinal applicator 200 with the exception of the base 752) is connected with a bag dispenser 755. More specifically, the bag dispenser 755 comprises a flexible body 756 that can be squeezed by a human hand in the direction of the arrows 758 to deploy medicinal cream (not shown) residing in the bag dispenser 755 through the anal medicinal applicator 750 and into an anal canal via the dispensing slots 751. In the present embodiment, the bag dispenser 755 possesses a base 760 and a rigid or semi-rigid top portion 754 that is joined to a connecting element (not shown). The connecting element is adapted to connect to the base handle 752, such as through a screw-thread relationship, a clip relationship, or some other attachment configuration known to those skilled in the art. In the present embodiment, the base handle 752 possesses longitudinal ribs to enhance gripping by a human hand between a human thumb and finger/s. The bag dispenser 755 can be any flexible material known to those skilled in the art including a flexible polymer, metal foil, or the flexible materials known to those skilled in the art. As a skilled artisan will appreciate, the syringe 700 and the flexible bag dispenser 755 are hardly exhaustive of the number of medicinal cream dispensing devices known to those skilled in the art, which are adapted to cooperate with the anal medicinal applicator embodiments described herein or otherwise understood within the scope and spirit of the present invention.

Figure 8A:
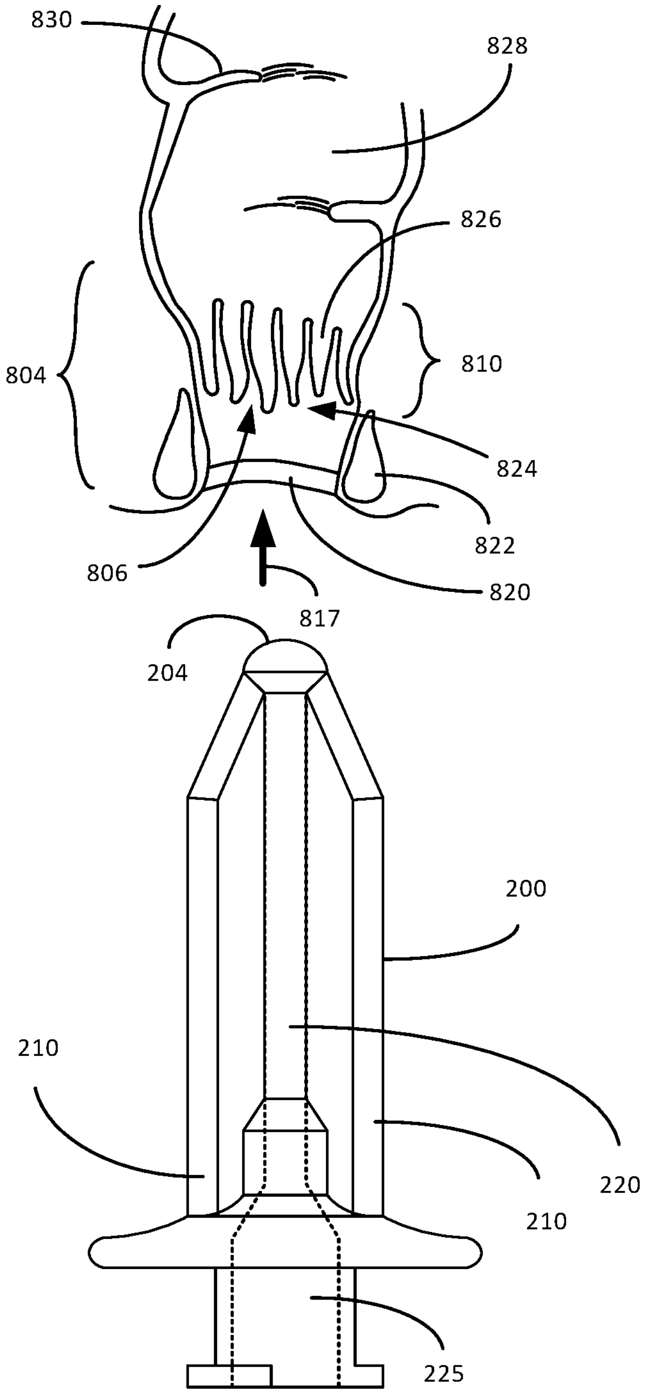
FIGS. 8A and 8B illustratively show a line drawing of an application embodiment of an anal medicinal applicator applied with an anal canal consistent with embodiments of the present invention.
Figure 8B:
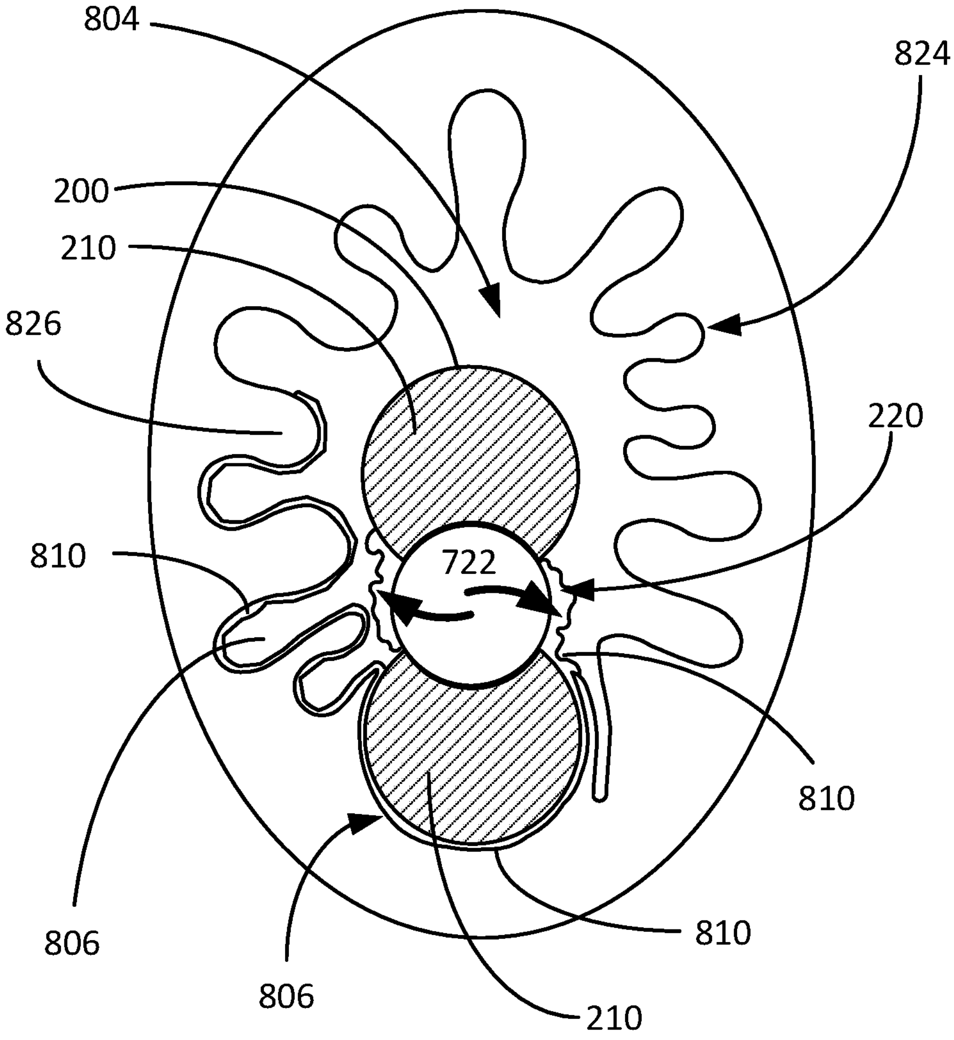

FIGS. 8A and 8B illustratively show a line drawing of an embodiment of an anal medicinal applicator engaging with an anal canal consistent with embodiments of the present invention. FIG. 8A depicts the anal medicinal applicator 200 about to be inserted in the anal canal 804 (shown by the arrow 817 pointing to the opening of the anus 820). The general anatomy of the anal canal 804 includes a transition zone 810 that illustratively shows corrugations/folds formed by anal crypts 806 and anal columns 826. The dentate line 824 defines the start of the corrugations/folds in the anal canal 804. For reference, the internal anal sphincter 822, that constricts the anus 820, is shown on either side of the anus 820, further up the anal canal 804 is the rectum 828 and the levator ani muscle 830. This is a very coarse artistic impression of the intestine and anal canal that meets the resolution needed for explanation for this disclosure, but may not have the anatomical resolution known to those skilled in the art. For example, the term "anal canal" as used herein may include all parts of the inner intestinal tract that interfaces the anal medicinal applicator 200, thereby possibly deviating from the technical specificity of the term.

FIG. 8B illustratively depicts a line drawing of a cross-section of the anal canal 804 with an anal medicinal applicator embodiment 200 deployed therein consistent with embodiments of the present invention. The cross-section of the anal canal 804 and the cross-section 251 of the anal medicinal applicator 200 (of FIG. 4B) is shown at the dentate line 824. The oblong/non-circular anal medicinal applicator 200 can more easily reach into the corrugated folds formed by the anal columns 826 and anal crypts 806, thereby spreading the medicinal cream 710 more evenly on the surface of the anal canal 804. By spinning the anal medicinal applicator 200 either clockwise or counterclockwise about the axis 217, the medicinal cream 710 can reach inside the folds at the dentate line 824 as shown when the medicinal cream 710 is dispensed out through the longitudinal slots 220, shown by the arrows 722. Spreading the medicinal cream may be enhanced when holding the base 206 and possibly tipping the shaft 210 away from a neutral axis 217. This is a very coarse artistic impression of the intestine and anal canal that meets the resolution needed for explanation for this disclosure, but may not have the anatomical resolution known to those skilled in the art.

Figure 9A:
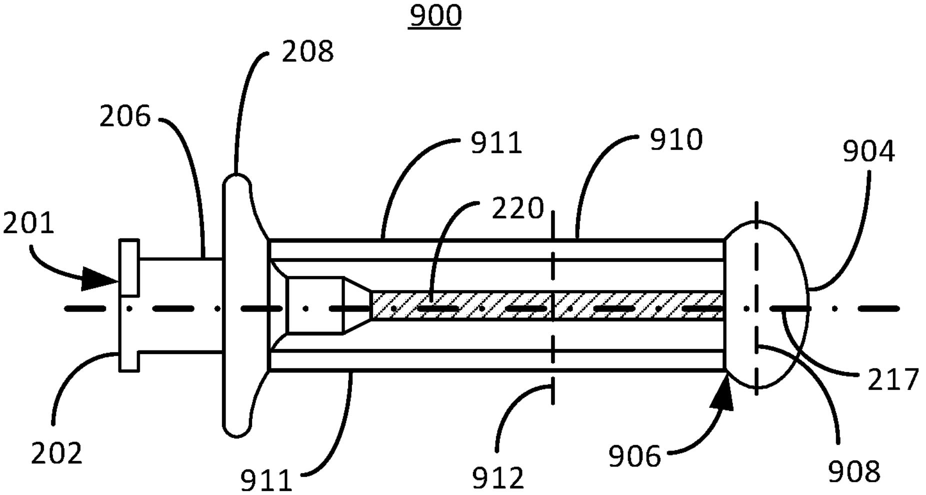
FIGS. 9A-9D illustratively depict drawings of various embodiments of an enlarged dome cap consistent with embodiments of the present invention.

FIGS. 9A-9D illustratively depict drawings of various embodiments of an enlarged dome cap consistent with embodiments of the present invention. With reference to FIG. 9A, an anal medicinal applicator embodiment 900 is shown with many of the same features described in conjunction with FIG. 2D. In this particular embodiment, however, the shaft 910 is not tapered at the dome transition 906, rather the dome 904 is larger than the dome 214 of FIG. 2D, comprising a maximum dome radius 908 that is larger than the maximum shaft radius 912. In this embodiment, the lobes 911 extend to the dome transition 906. The maximum shaft radius 912 is defined as the furthest distance to the outer edge (furthest outer edge point) of the shaft 910 from the axis 217, as measure orthogonally relative to the axis 217. The dome radius 908 is defined as the distance from the axis 217 to the outer edge of the dome 904 as measured orthogonally relative to the axis 217. In the present embodiment, the dome 904 is bulbous, mechanically limiting medicinal cream 710 leaking higher up in the intestines (from the anal canal 804 towards the rectum 828, for example). Embodiments of the anal medicinal applicator 900 further contemplate including an anal medicine blocking ring 610/680, for example.

Figure 9B:
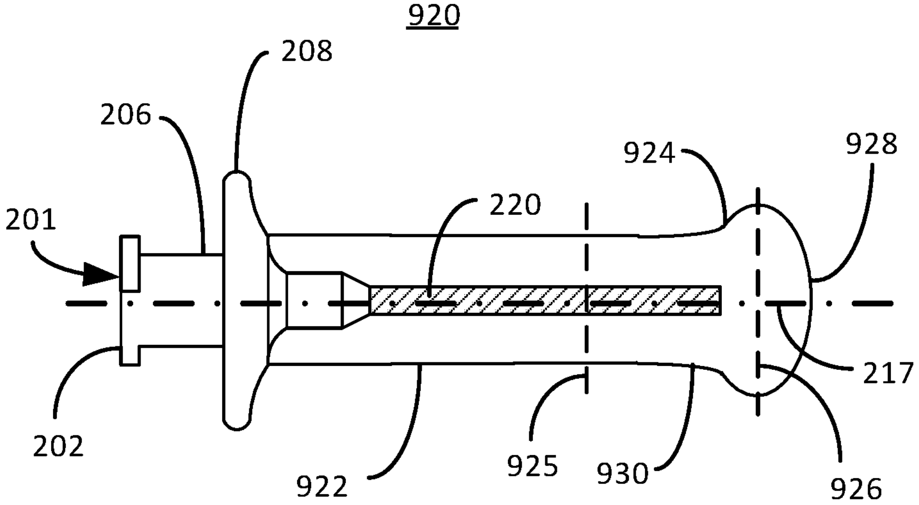

FIG. 9B is another embodiment of an anal medicinal applicator 920 consistent with embodiments of the present invention. This anal medicinal applicator embodiment 920 may comprise a circular shaft or a non-circular shaft with a bulbous-shaped dome 928. There is a smooth transition 930 (perhaps tapered) between the bulbous-shaped dome 928 and the shaft 922. Other embodiments do not contemplate a transition. As with FIG. 9A, the maximum dome radius 926 is larger than the maximum shaft radius 925 (the radii as previously defined). Embodiments of the anal medicinal applicator 920 further contemplate including an anal medicine blocking ring 610/680, for example.

Figure 9C:
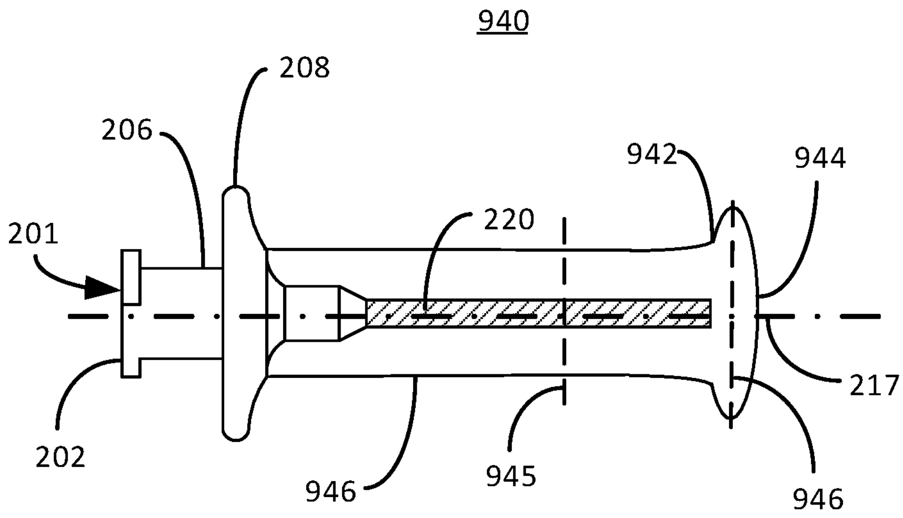

FIG. 9C is yet another embodiment of an anal medicinal applicator 940 consistent with embodiments of the present invention. This anal medicinal applicator embodiment 940 may possess a circular shaft or a non-circular shaft with a shorter mushroom-shaped dome 944. The mushroom-shaped dome 944 possesses a transition 942 between the shaft 946 and the mushroom-shaped dome 944. As with FIG. 9A, the maximum dome radius 946 is larger than the maximum shaft radius 945 (the radii as previously defined). Embodiments of the anal medicinal applicator 940 further contemplate including an anal medicine blocking ring 610/680, for example.

Figure 9D:
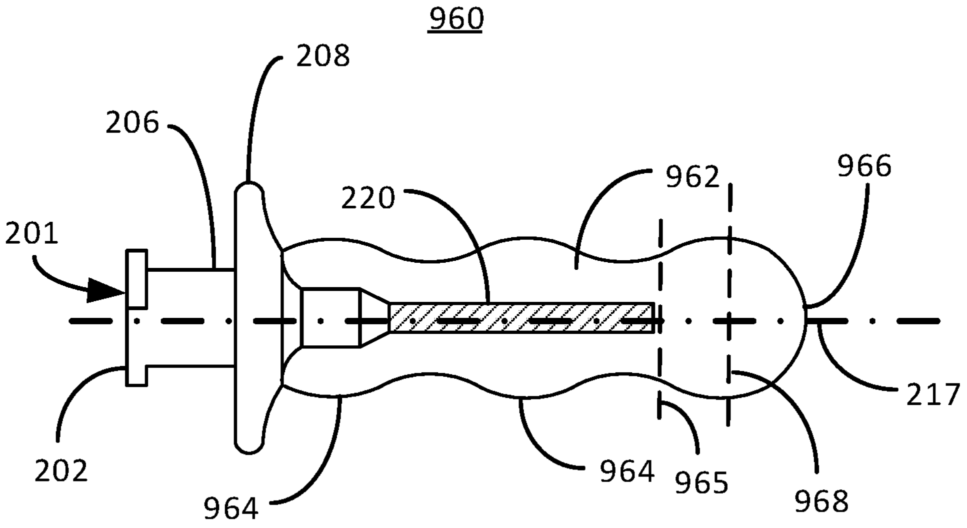

FIG. 9D is another embodiment of an anal medicinal applicator 960 consistent with embodiments of the present invention. This anal medicinal applicator embodiment 960 may possess a circular or a non-circular shaft 962 that undulates 964 along the length of the shaft 962, terminating at a bulbous dome 966. The bulbous dome 966 comprises a maximum radius which is larger than the radius of the shaft 962 at the transition 965 proximal to the bulbous dome 966 (the radii as previously defined). In the present embodiment, the shaft 962 possesses a plurality of undulations 964, as shown. Certain embodiments envision the undulations 964 being the maximum radius along the shaft 962, while other embodiments envision different sized undulations 964. Some embodiments contemplate the undulations 964 comprising an undulation radius that is approximately the same size as the bulbous dome radius 968, while other embodiments contemplate at least one smaller undulation radius than the bulbous dome radius 968. Embodiments of the anal medicinal applicator 960 further contemplate including an anal medicine blocking ring 610/680, for example.

Figure 9E:
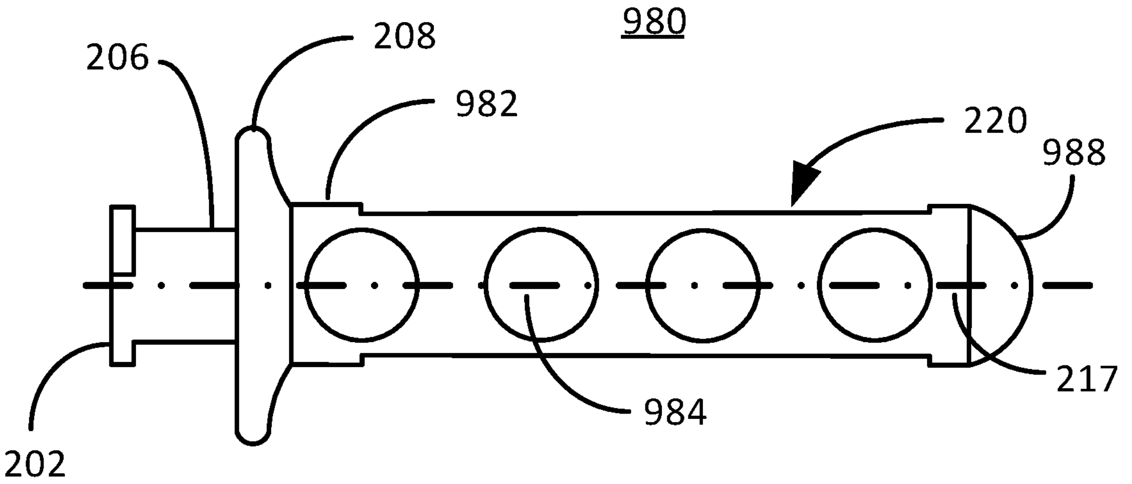
FIGS. 9E and 9F illustratively depict yet another embodiment of an anal medicinal applicator 980 consistent with embodiments of the present invention.
Figure 9F:
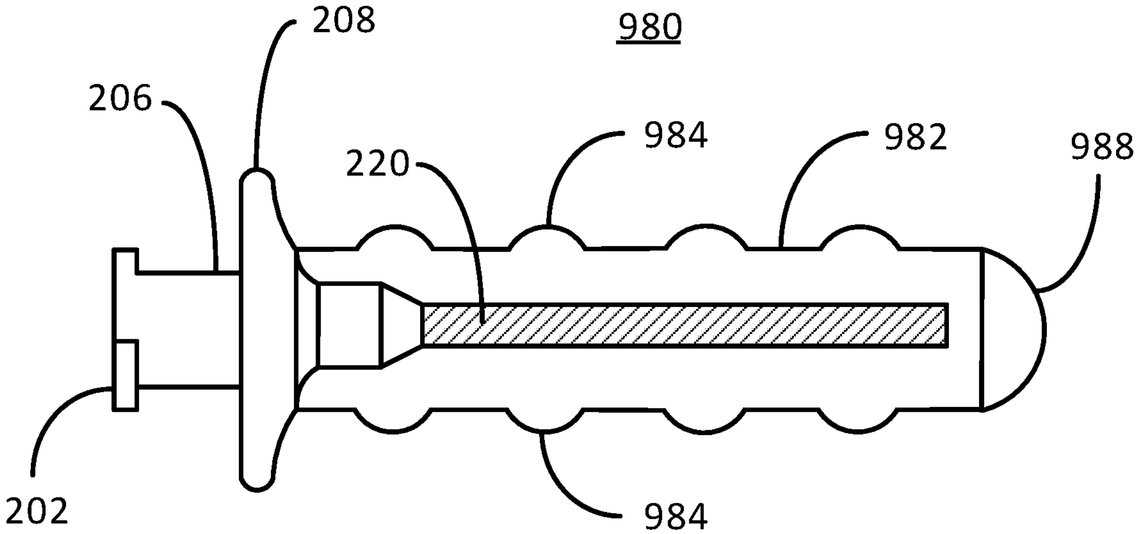

FIGS. 9E and 9F illustratively depict yet another embodiment of an anal medicinal applicator 980 consistent with embodiments of the present invention. As shown in FIG. 9E, the anal medicinal applicator 980 is rotated with the top view revealing four semi-spherical bumps 984 evenly distributed along the length of the shaft 982. For reference, the longitudinal slots 220 are shown as recesses. The dome 988 is depicted as a semi-sphere at the distal end of the anal medicinal applicator 980, but could easily assume any of the shapes depicted in the other figures or optionally other shapes appreciated by skilled artesian in possession of the scope and spirit of the present invention. Embodiments of the anal medicinal applicator 980 further contemplate including an anal medicine blocking ring 610/680, for example.

FIG. 9F illustratively depicts a side view of the anal medicinal applicator 980 (rotated 90° about the axis 217 from the illustration of FIG. 9E) showing the bumps 984, which may improve the spreading and dispersion of medicinal cream in an anal canal 804. From this angle, a side view of the semi-spherical bumps 984 are shown dispersed across the length of the shaft 982. The semispherical bumps 984 can extend from a circular cross-sectional shaft or from a noncircular cross-sectional shaft without departing from the scope and spirit of the present invention. Other embodiments envision similar bumps being non-semispherical, such as oblong, elliptical or other shapes. Furthermore, the bumps can be uniformly spread as shown, randomly spread or otherwise distributed in some other chosen interval. Other embodiments envision the bumps extending further or closer from the axis 217 (bump height) from the bumps 984 as shown.

Figure 10:
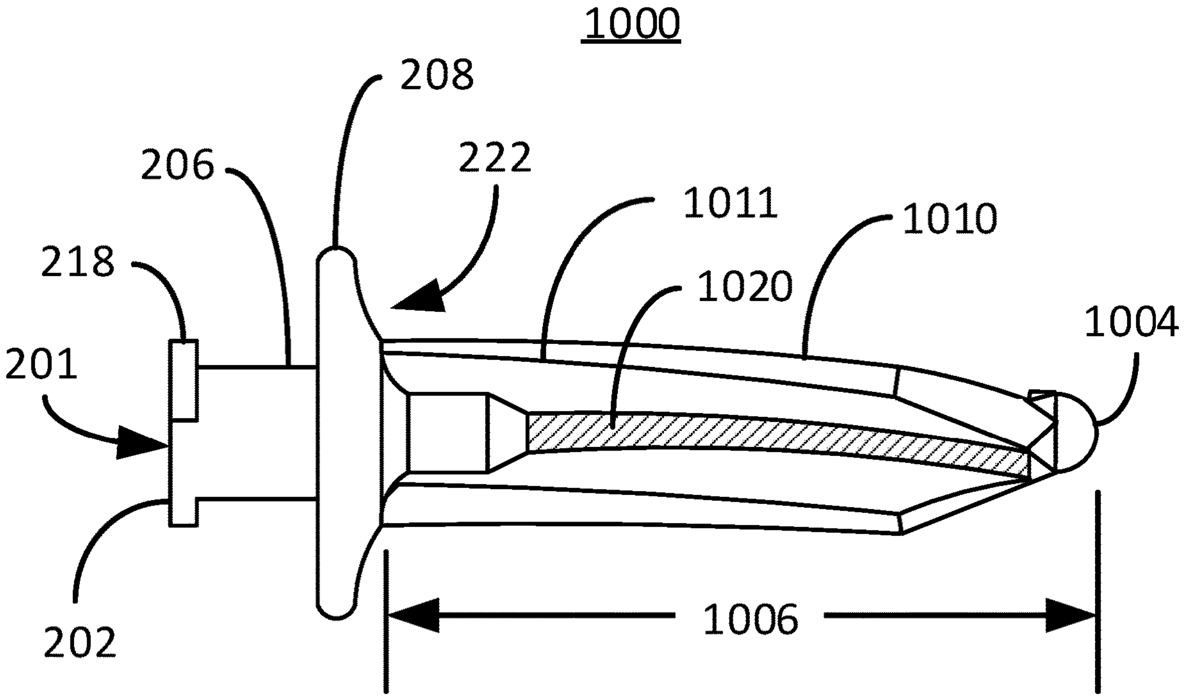
FIG. 10 illustratively depicts a side view of and alternative anal medicinal applicator embodiment consistent with embodiments of the present invention.

FIG. 10 illustratively depicts a side view of an alternative anal medicinal applicator embodiment 1000 consistent with embodiments of the present invention. This corkscrew anal medicinal applicator 1000 is similar to the anal medicinal applicator 200 of FIG. 2A with the exception that the longitudinal slots 1020 and the lobes 1011 of the anal shaft 1010 are twisted in a corkscrew arrangement. The anal shaft 1010 does not map to a circular outer profile shape 161. Other embodiments envision an anal shaft that does map to a circular outer profile shape 161 and has nonlinear (e.g., corkscrew/twisted) longitudinal slots. Certain embodiments envision the present depiction defining an anal cavity region 1006 consisting of all elements distal to the anus contact surface 222 of the anus abutting stop plate 208. The anal cavity region 1006 are those elements of the anal medical applicator 1000 that reside in the anal cavity 804 (and as deep into the rectum 828 as the anal medicinal applicator 1000 can reasonably go) when inserted into an anal cavity, whereby the anus contact surface 222 is butting up against the surface of the anus 820.

Figure 11A:
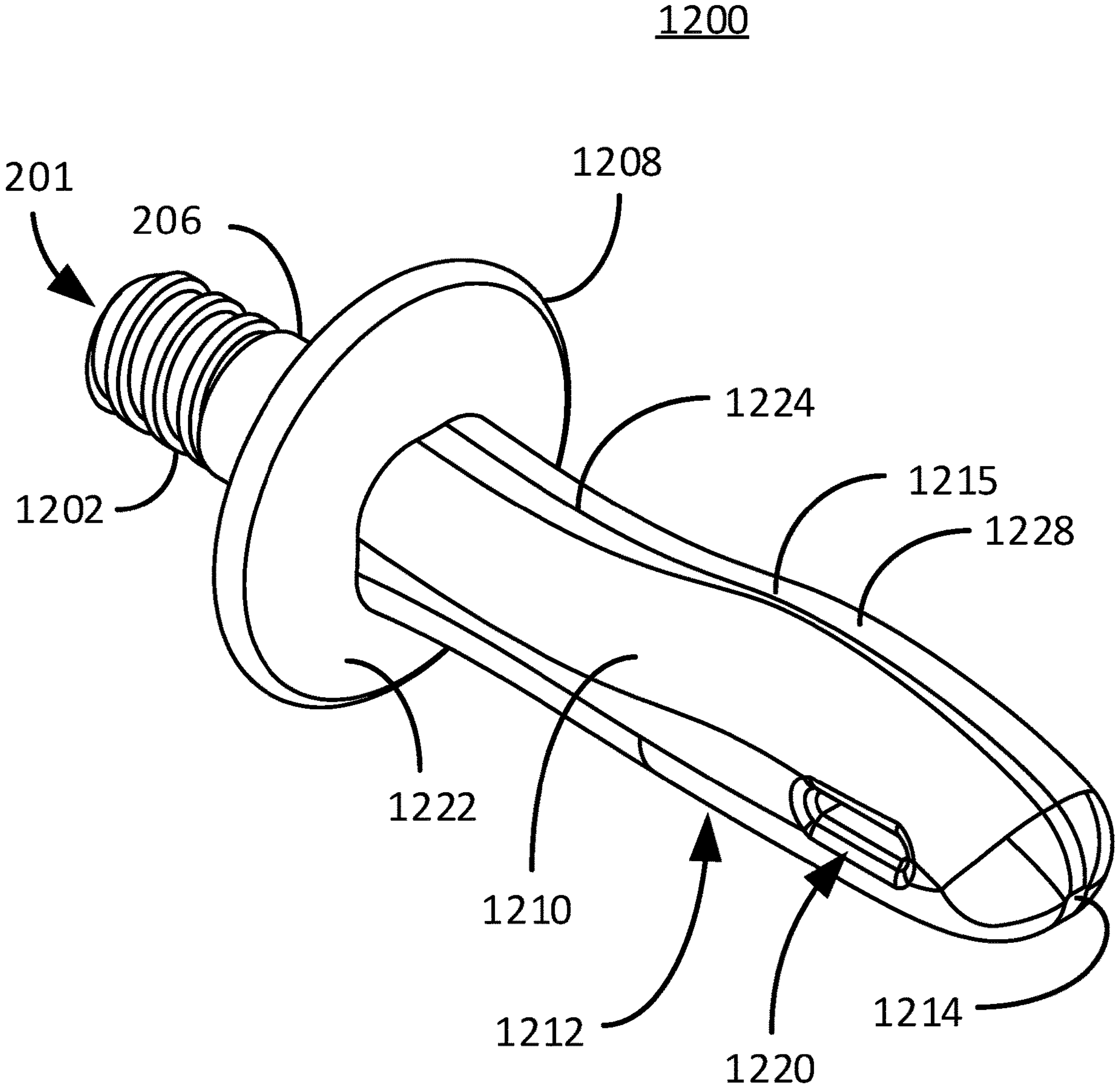
FIGS. 11A and 11B are front and rear view isometric line drawings of yet another optional medicinal applicator embodiment consistent with embodiments of the present invention.
Figure 11B:
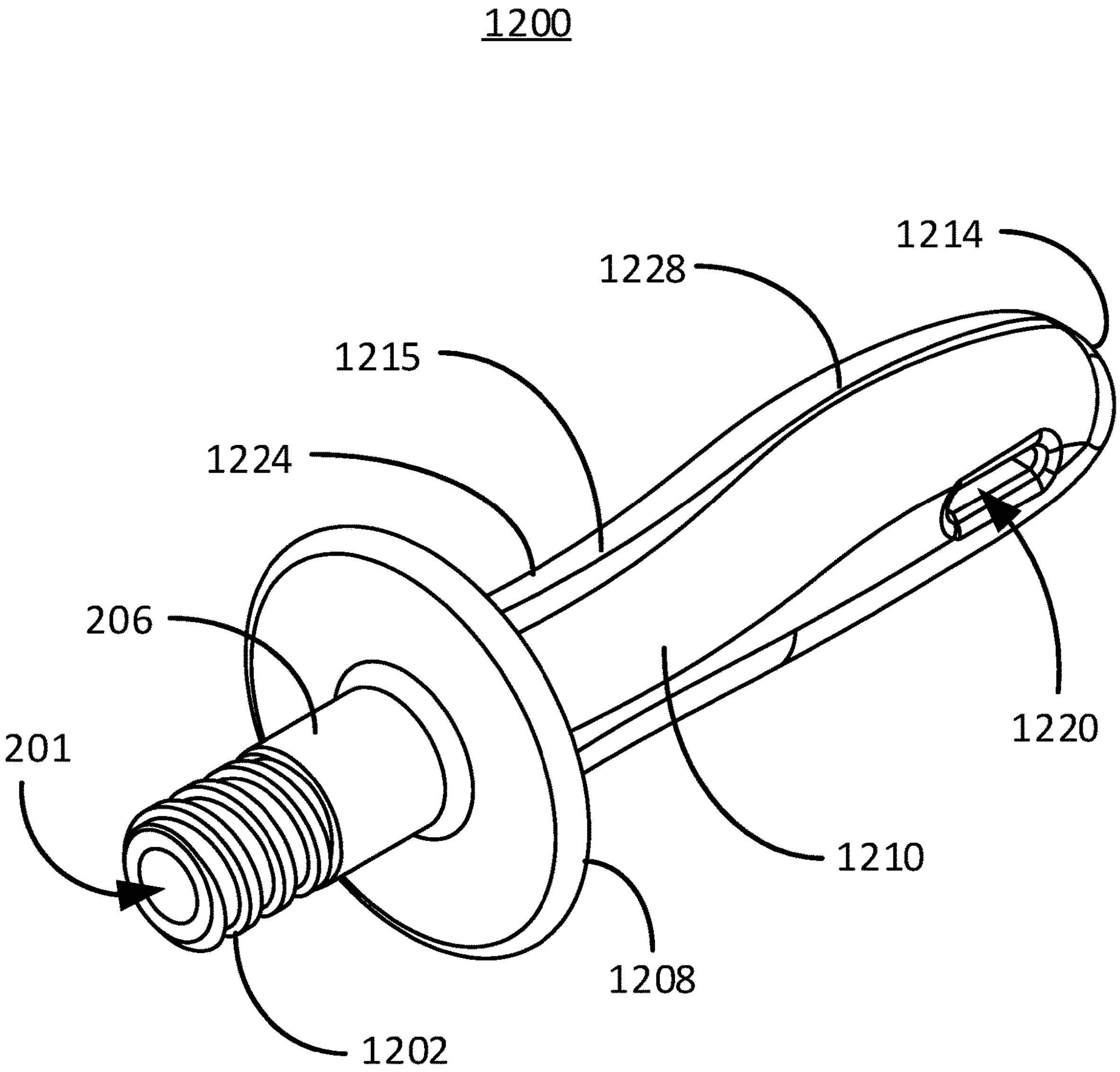

FIGS. 11A and 11B are front and rear view isometric line drawings of yet another optional medicinal applicator embodiment consistent with embodiments of the present invention. FIG. 11A is a front view isometric line drawing of a medicinal applicator 1200, which generally comprises a handle 206 that is separated from the shaft 1210 by a stop plate 1208. The shaft 1210 is defined by a shaft trailing edge 1212 and shaft leading edge 1215 that is generally shaped like a finger with a thin proximal shaft region 1224 and a larger shaft paddle 1228. Near the distal end 1214 of the side of the shaft 1210 is an exit aperture 1220 through which a medicinal cream 710 (of FIG. 7A) can exit into the anal canal 804 (of FIG. 8A) or vagina. The stop plate contact surface 1222 is configured to rest up against a person's anus 820 or vaginal opening under normal use with the handle 206 and syringe 700 (of FIG. 7A) permanently outside of the human body. Similar to the other embodiments, medicinal cream 710 is configured to flow into the medicinal cream receiving port 201 by way of a syringe 700 or tube 755 (of FIG. 7B). A syringe 700 or tube 755 can be screwed onto the attachment threads 1202.

FIG. 11B is a rear view isometric line drawing of a medicinal applicator 1200, showing the medicinal cream receiving port 201 comprising syringe attachment threads 1202 on which a syringe 700 or tube 755 can be attached. Medicinal cream 710 can be made to flow through the medicinal cream receiving port 201 and exit through the exit aperture 1220. More specifically, the exit aperture 1220 is in communication with the medicinal cream receiving port 201 via the passageway 1225 (shown in FIG. 12B). The distal end 1214 of the shaft 1210 is dome-shaped to be easily inserted in an anus 820 (of FIG. 8A) or vagina (not shown) as far as the stop plate 1208 will allow. As shown, the shaft paddle 1228, which is shaped a little like a finger, protrudes from the shaft leading edge 1215, relative to the proximal shaft region 1224.

Figure 12A:
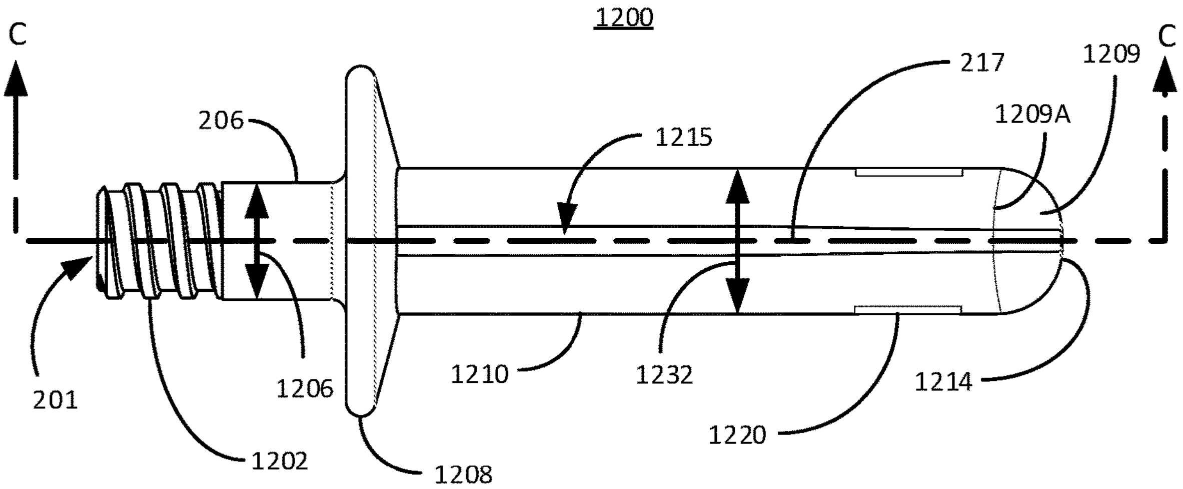
FIG. 12A is a top view line drawing of the medicinal applicator from FIGS. 11A and 11B in accordance with embodiments of the present invention.

FIG. 12A is a top view line drawing of the medicinal applicator 1200 from FIGS. 11A and 11B. As shown here, the shaft 1210, as viewed from the shaft leading edge 1215, essentially defines a uniform shaft width 1232 of approximately 0.4 inches across with certain embodiments envisioning a shaft width 1232 in the range between 0.25 inches and 1.0 inches. The cut-line C-C, which aligns with the shaft axis 217 (which is a conceptual mid-line/axis), cuts through the shaft leading edge 1215 and shaft trailing edge 1212 (hidden but shown in FIG. 12B) from the medicinal cream receiving port 201 through the applicator distal end 1214. The distal end 1214 is the tip of a dome-shaped region 1209 that is shown starting from the dotted line 1209A and ending at the distal end 1214. With detail, the cut-line C-C extends along the syringe attachment threads 1202 and handle 206, bisecting the stop plate 1208 and the length of the shaft 1210. In the present embodiment, the shaft width 1232 is larger than the handle diameter 1206, with certain commercial embodiments contemplating a shaft width 1232 comprising a diameter in the range of between 0.25 inches and 1.0 inches. Certain embodiments envision the handle diameter 1206 being larger than the shaft width 1232 that could reach a diameter of 2 inches. As shown here, there are two exit aperture 1220 located on both sides of the shaft 1210, approximately where the shaft paddle 1228 is located.

Figure 12B:
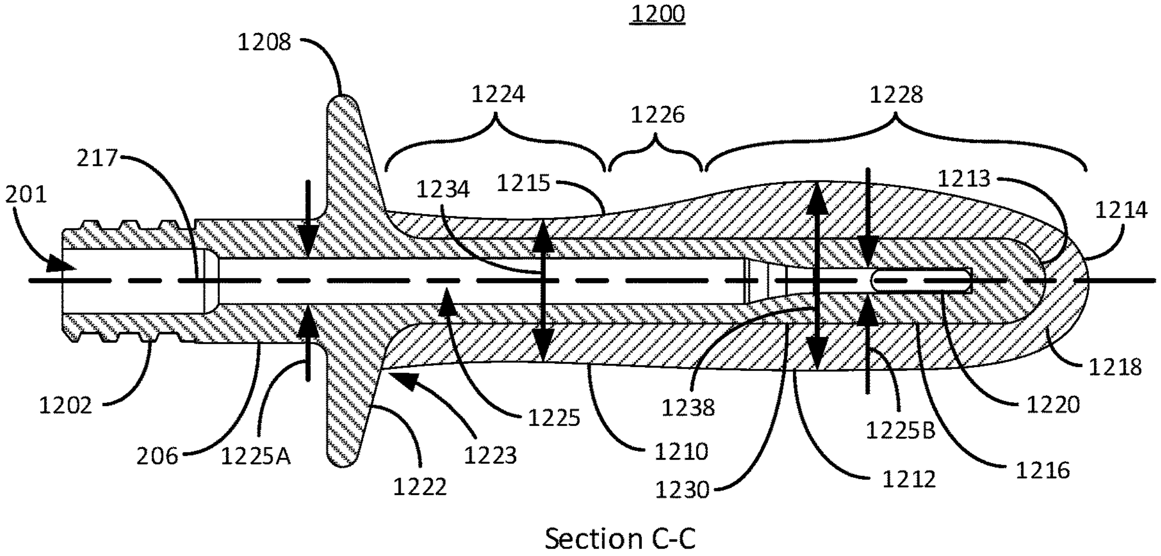
FIG. 12B is a side view cross-sectional line drawing along the cut-line C-C of the medicinal applicator from FIG. 12A consistent with embodiments of the present invention.

FIG. 12B is a side view cross-sectional line drawing along the cut-line C-C of the medicinal applicator 1200 from FIG. 12A consistent with embodiments of the present invention. In this embodiment, the shaft 1210 generally comprises a shaft core 1216 surrounded and encased by shaft outer sleeve 1218. Certain other embodiments do not have a shaft core 1216 completely covered by the shaft outer sleeve 1218. Some embodiments envision the shaft core 1216, the syringe attachment threads 1202, the handle 1206 and the stop plate 1208 being a unitary element as depicted by the upwardly left tilting crosshatched section. A unitary element is considered a single piece of molded or printed polymer, carbon fiber composite, metal, or some other material that does not start with two or more elements fixed, adhered, or otherwise connected together. Certain embodiments envision the shaft core 1216 being essentially rigid, while other embodiments envision the shaft core 1216 allowing for some noticeable deflection when used (i.e., perhaps deflecting upwards of an inch at the distal end 1214), which can be accomplished by a medium to stiff rubber or silicone, for example. The passageway 1225 extends from the medicinal cream receiving port 201, through the exit aperture 1220, with the exit aperture 1220 in communication with the medicinal cream receiving port 201. Accordingly, medicinal cream 710 can flow into the medicinal cream receiving port 201, through the passageway 1225 and out through the exit aperture 1220 into the anal canal 804 or vaginal cavity (not shown). In this embodiment, the passageway 1225 comprises a wide passageway portion 1225A that extends from the handle 206 to at least a portion of the shaft paddle 1228 and then transitions into a narrow passageway portion 1225B. The exit aperture 1220 exits from the narrow passageway portion 1225B. Certain commercial embodiments contemplate the wide passageway portion 1225A having a diameter of between 0.05 inches and 0.2 inches, and the narrow passageway portion 1225B having a diameter between 0.025 inches and 0.2 inches. The shaft core distal end 1213 of the shaft core 1216 extends past the exit aperture 1220. Certain other embodiments contemplate a passageway portion having a uniform diameter or optionally a plurality of different diameters, while still other embodiments envision a non-uniform or non-circular cross-sectional shape. For reference, the shaft axis 217, which is a conceptual centerline extends through the center of the handle 206. In other words, the shaft axis 217 is equidistant equidistant the handle 206, which is considered equivalent to running equidistant 'along' the handle 206. However, in this embodiment the shaft axis 217 is not necessarily in the center of the shaft 1210. In other words, the leading edge shape 1215 and the trailing edge shape 1212 are not equidistant from the shaft axis 217 in this embodiment.

One embodiment envisions the shaft outer sleeve 1218 bonded to the shaft core 1216, whether fixedly or removably, starting at least from the stop plate contact surface 1222 at the shaft-to-stop plate interface 1223. The shaft outer sleeve 1218 essentially encapsulates the shaft core 1216. The shaft outer sleeve 1218 defines a shaft trailing edge 1212 and a shaft leading edge 1215. In one embodiment, a straight line to the dome of the distal end 1214 can define the shaft trailing edge 1212, or as shown in the present embodiment, the shaft trailing edge 1212 is slightly curved to a narrow point at the shaft paddle minimum diameter 1234. Optional embodiments contemplate a shaft trailing edge 1212 possessing other shapes, such as one similar to the leading edge 1215. The shape of the shaft leading edge 1215 is more notably curved than the shaft trailing edge 1212. More specifically, in the present embodiment, from the stop plate contact surface 1222 to the distal end 1214, the shaft leading edge 1215 comprises a small diameter proximal shaft region 1224, a paddle transition zone 1226, and a large diameter shaft paddle 1228. The proximal shaft region 1224 defines a shaft paddle minimum diameter 1234 that in certain embodiments is between 0.3 inches and 1 inch. In one commercial example, the shaft paddle minimum diameter 1234 is approximately 0.37 inches. The paddle transition zone 1226 defines a transition between the thin proximal shaft region 1224 and the wide shaft paddle 1228. The shaft paddle 1228 is the widest portion of the shaft 1210 with certain embodiments contemplating a maximum width of between 0.4 inches and 1.25 inches. In one commercial example, the shaft paddle maximum diameter 1238 is approximately 0.48 inches. Certain embodiments contemplate the shaft outer sleeve 1218 being composed of a material that is different from material composing shaft core 1216. The material that makes up the shaft outer sleeve 1218 can be comprised of a softer durometer than that of the shaft core 1216. The shaft outer sleeve 1218 can be composed of a rigid or semi-rigid plastic material, rubber, silicone, or other elastic or compliant material known to those skilled in the art. As previously mentioned, the finger-like shape of the shaft paddle 1228 enhances spreading medicinal cream on the inner skin surface of an anal canal 804 or vaginal cavity. The exit aperture 1220 is located at or near the shaft paddle 1228, which further enhances spreading medicinal cream 710 by way of the shaft paddle 1228.

Figure 12C:
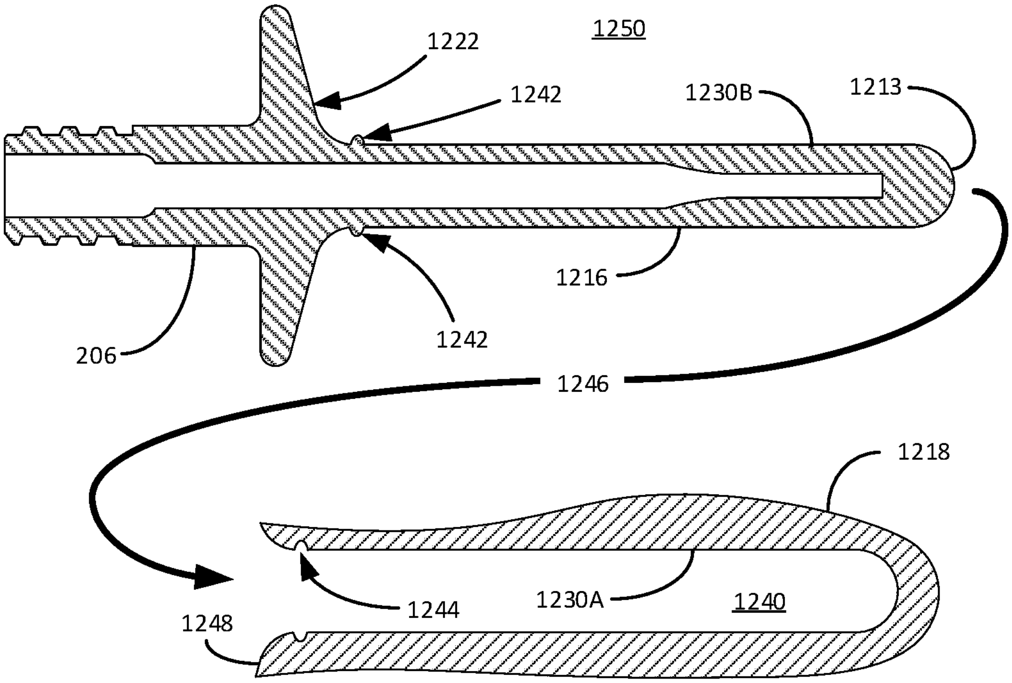
FIGS. 12C and 12D are line drawings of a cross-section view of another medicinal applicator embodiment consistent with embodiments of the present invention.
Figure 12D:
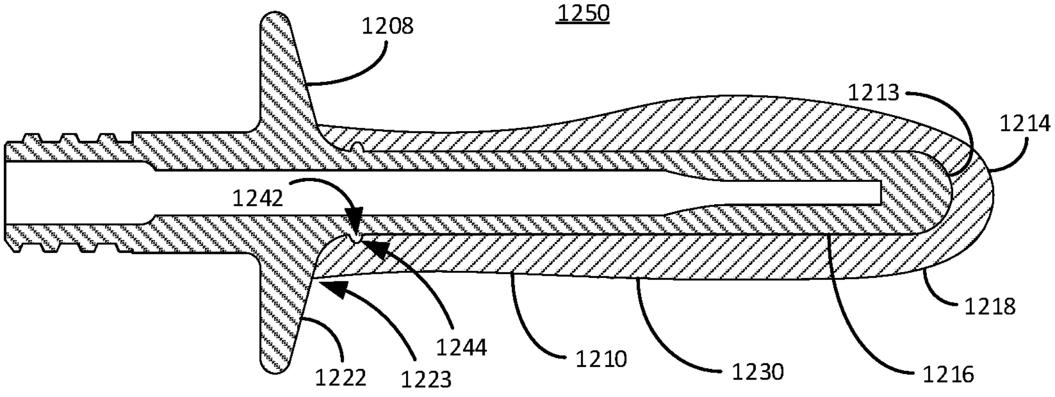

FIGS. 12C and 12D are line drawings of a cross-section view of another medicinal applicator embodiment consistent with embodiments of the present invention. The present removable sleeved medicinal applicator embodiment 1250 comprises a removable sleeve 1218 that can be taken off the shaft core 1216. In this way, the removable sleeve 1218 can be replaced with a new removable sleeve 1218 after use. As depicted in FIG. 12C, a shaft core 1216 is positioned to be inserted into a slotted region 1240 of the shaft outer sleeve 1218 as shown by the curved arrow 1246. The shaft outer sleeve 1218, as shown by the upwardly tilting right cross-hatched section, is configured to extend from the stop plate contact surface 1222 beyond the shaft core distal end 1213. Here, the shaft core 1216 comprises a shaft retaining ring 1242 that extends outwardly from the shaft outer surface 1230B near the stop plate contact surface 1222. When the shaft core 1216 is inserted in the shaft outer sleeve slotted region 1240, the outer sleeve 1218 locks over the shaft retaining ring 1242 by way of a mating sleeve retaining ring recess 1244. Certain other embodiments envision the shaft outer sleeve slotted region 1244 being narrower than the width of the shaft core 1216 to compress against the shaft core 1216 in order to fit snugly.

FIG. 12D depicts a cross-section line drawing of the shaft core 1216 inserted in the shaft outer sleeve slotted region 1240. As shown, the shaft outer sleeve 1218 tightly conforms to the shaft core 1216 with the sleeve retaining ringed recess 1244 accommodating the shaft retaining ring 1242. As further shown, the sleeve proximal end 1248 not shown in 12D is butt-up against the stop plate contact surface 1222 of the stop plate 1208. Certain embodiments envision a silicone, or like material, shaft outer sleeve 1218 that grips the shaft core surface 1230B not shown in 12D via friction at the sleeve/core interface 1230. Certain other embodiments envision a different kind of locking arrangement such as a peg and accommodating peg slot, or some other male/female feature that can cooperate to hold the removable shaft outer sleeve 1218 onto the shaft core 1216. As should be appreciated, the sleeve slotted surface 1230A not shown in 12D can comprise a male feature that fits into a female feature in the shaft core surface 1230B not shown in 12D while maintaining the same or similar functionality. Yet other embodiments envision a non-removable sleeve outer surface 1218 that is bonded to the shaft core 1216, such as by way of adhesive. The non-removable sleeve embodiment can further include the shaft retaining ring 1242 and sleeve retaining ringed recess 1244 as shown in FIG. 12D and without departing from the scope and spirit of the present invention.

Figure 13A:
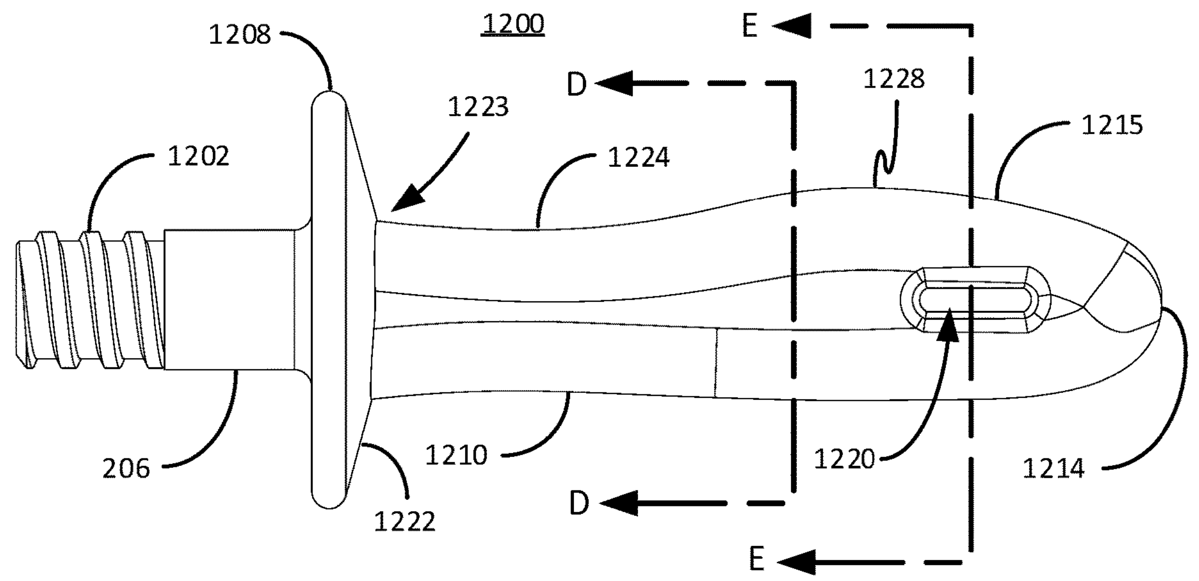
FIG. 13A is a side view line drawing of the medicinal applicator from FIGS. 11A and 11B consistent with embodiments of the present invention.

FIG. 13A is a side view line drawing of the medicinal applicator 1200 from FIGS. 11A and 11B. As shown here, there is a first cut-line D-D bisecting the shaft 1210 between the shaft paddle 1228 and the proximal shaft region 1224 on the shaft leading edge 1215, and a second cut-line E-E bisecting the exit aperture 1220 located between the proximal shaft region 1224 and the distal end 1214. For reference, the shaft 1210 extends from the stop plate contact surface 1222 at the shaft-to-stop plate interface 1223 and terminates at the distal end 1214. Also depicted are the syringe attachment threads 1202 that lead into the handle 206, which terminates at the stop plate 1208.

Figure 13B:
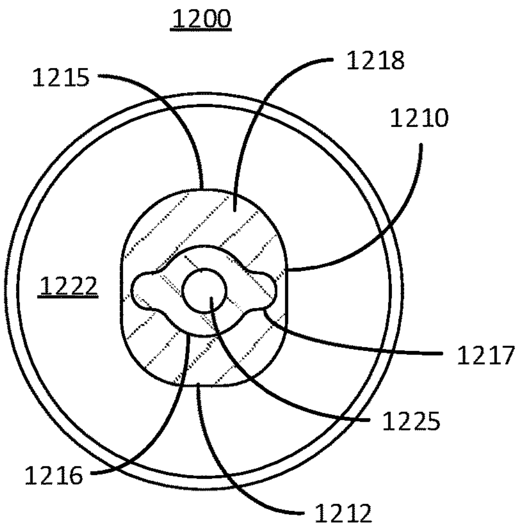
FIG. 13B is a line drawing cross-section view along cut-line D-D of the medicinal applicator embodiments as shown in FIG. 13A consistent with embodiments of the present invention.

FIG. 13B is a line drawing cross-section view along cut-line D-D of the medicinal applicator embodiments 1200 as shown in FIG. 13A. As shown, the shaft outer sleeve 1218 surrounds the shaft core 1216. Also shown, the cut-line D-D cuts through (or bisects) a portion of the shaft 1210 that includes the shaft paddle 1228 not shown in 13B. As to be expected, the shape of the shaft outer sleeve 1218 is oblong with the longest part of the shaft trailing edge 1212 extending from the 1212 to the shaft leading edge 1215. In the present configuration, the shaft core 1216 is molded to the shaft outer sleeve 1218 with a shaft core keyed feature 1217 to stabilize or otherwise lock the shaft core 1216 in the shaft outer sleeve 1218. The passageway 1225 runs down the middle of the shaft core 1216 as shown, which in the present embodiment is circular. The stop plate contact surface 1222 is shown for reference.

Figure 13C:
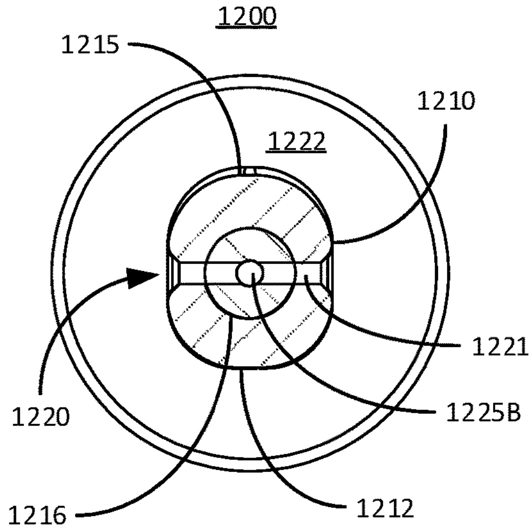
FIG. 13C is a line drawing cross-section view along cut-line E-E of the medicinal applicator as shown in FIG. 13A consistent with embodiments of the present invention.

FIG. 13C is a line drawing cross-section view along cut-line E-E of the medicinal applicator 1200 as shown in FIG. 13A. The cut-line E-E bisects the exit aperture 1220 to show an exit aperture channel 1221 that is in communication with the exit aperture 1220 and the narrow passageway portion 1225B. In this embodiment, the exit aperture 1220 is on either side of the shaft trailing edge 1212 along the thin part of the shaft trailing edge 1212. The stop plate contact surface 1222, the shaft leading edge 1215 and the 1212 are shown for reference.

Figure 14:
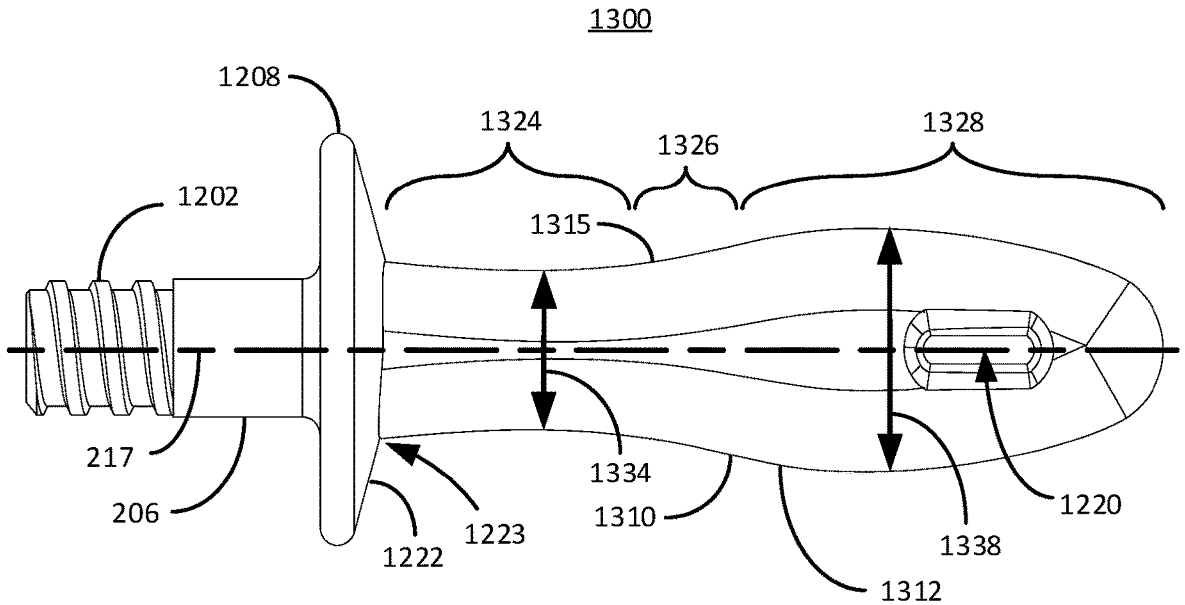
FIG. 14 is a side view line drawing of yet another embodiment of a medicinal applicator consistent with embodiments of the present invention.

FIG. 14 is a side view line drawing of yet another embodiment of a medicinal applicator consistent with embodiments of the present invention. In this medicinal applicator embodiment 1300, the shaft leading edge 1315 and the shaft trailing edge 1312 are symmetric. As shown here, the proximal shaft region 1324 has the smallest diameter 1334 of the shaft 1310 and the paddle region 1328 has the widest diameter 1338 in the shaft 1310. In the present embodiment, the cross-section of the shaft 1310 is more oblong than that shown in FIGS. 13B and 13C. The present medicinal applicator embodiment 1300 can comprise the same handle and medicinal syringe/tube attachment threads 1202 that are separated from the shaft 1310 via (by?) the stop plate 1208. Here, the exit aperture 1220 is located approximately in the paddle zone 1328 to utilize the shape of the paddle 1238 to disperse medicinal cream 710 expelled from the exit aperture 1220. In this embodiment, the leading edge shape 1315 and the trailing edge shape 1312 are equidistant from the shaft axis 217 (i.e., the shaft axis 217 is the center line between leading edge 1315 and the trailing edge 1312) along all points as viewed from right angles to the shaft axis 217.

Figure 15:
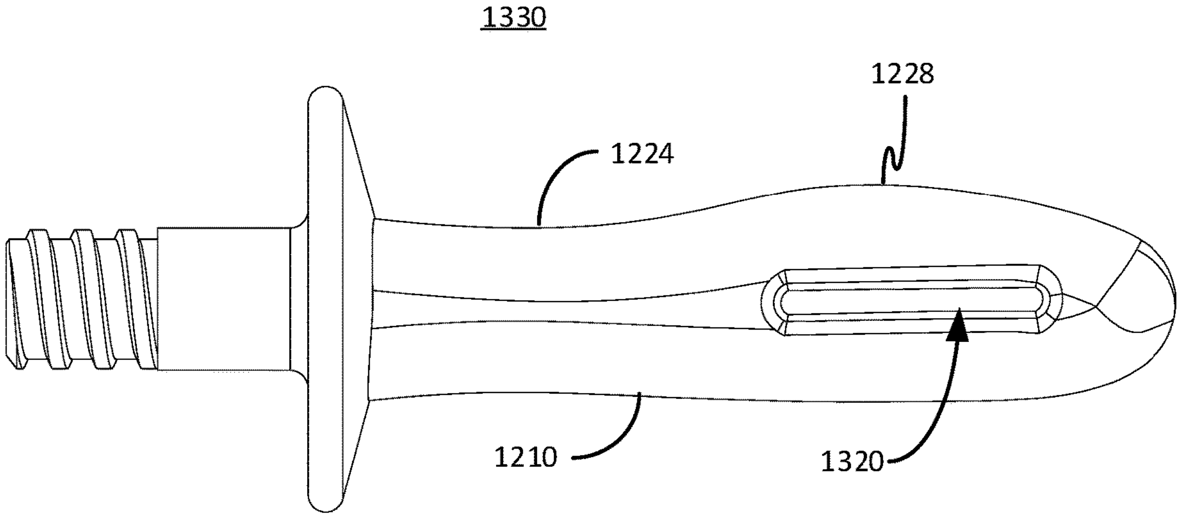
FIG. 15 is a side view line drawing of yet another embodiment of a medicinal applicator consistent with embodiments of the present invention.

FIG. 15 is a side view line drawing of yet another embodiment of a medicinal applicator consistent with embodiments of the present invention. As shown, the medicinal applicator embodiment 1330 is more or less the same as the embodiment of FIG. 13A with the exception that the exit aperture 1320 is an elongated slot that extends along a greater portion of the paddle region 1228. Other embodiments envision the exit aperture extending along more of the length of the shaft 1210 into the proximal shaft region 1224.

Figure 16A:
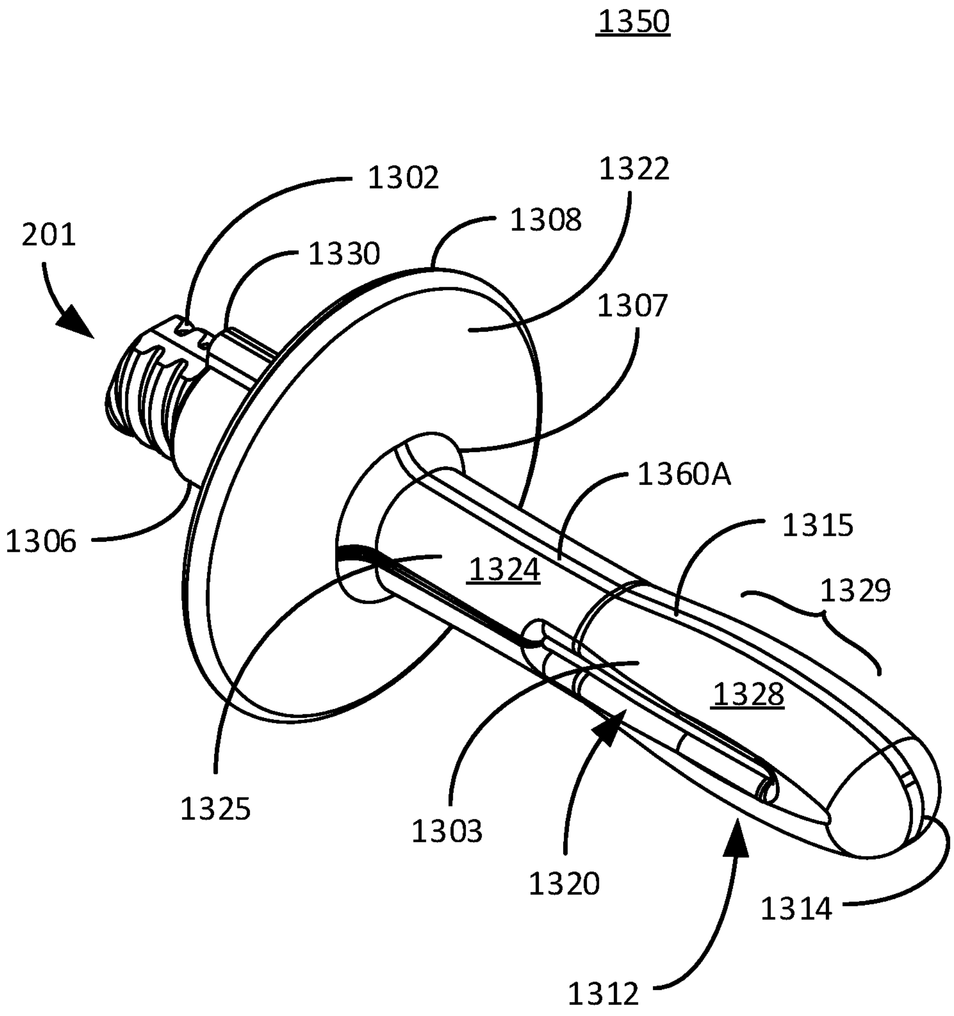
FIGS. 16A and 16B are line drawings of a variation of the medicinal applicator embodiment of FIG. 14 consistent with embodiments of the present invention.
Figure 16B:
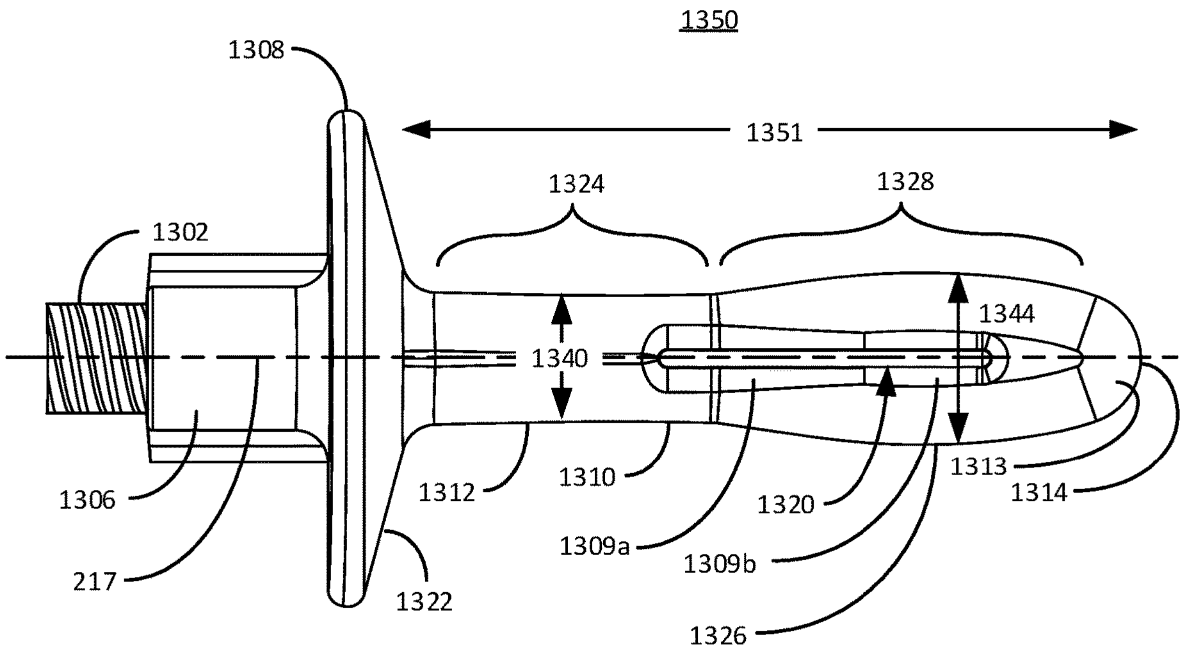

FIGS. 16A and 16B are line drawings of a variation of the medicinal applicator embodiment of FIG. 14 consistent with embodiments of the present invention. FIG. 16A is a front view isometric line drawings of a medicinal applicator 1350 with a symmetric paddle. The medicinal applicator 1350 generally comprises a handle 1306 that is separated from the shaft 1310 by a stop plate 1308. A medicinal cream receiving port 201 is located at the proximal end of the base 1306. The base 1306 includes a male threaded post 1302 that is configured to matingly engage or otherwise screw into an opposing female threaded connector on a syringe 700 (of FIG. 7A) or optionally a tube/bag dispenser 755 (of FIG. 7B). The base 1306 further comprises diametrically opposed protruding ribs 1330 that can be used to twist the shaft 1310 either clockwise or counterclockwise when inserted in a vaginal cavity or anal cavity (cavity). The protruding ribs 1330 extend from the threaded post 1302 to the stop plate 1308. In the present embodiment, the stop plate 1308 is circular with a tapered contact surface 1322 that is in contact with a human body just outside of the orifice/cavity when the medicinal applicator 1350 is inserted in a cavity. The contact surface 1322 tapers into the proximal region 1324 of the shaft 1310 via a stop plate radius 1307, which may or may not be a constant radial arc.

With respect to the shaft 1310 as also depicted in FIG. 16B, the shaft 1310 extends along a shaft axis 217 from the base 1306 to a proximal region 1324 and then to paddle region 1328 wherein the shaft 1310 terminates at an applicator tip 1314. A leading shaft edge 1315 and a trailing shaft all edge 1312 are diametrically opposed and define a shaft top and shaft bottom. The side view of FIG. 16B depicts the narrow proximal region 1324 of the shaft 1310 extending about 40% of the shaft length 1351 between the base 1306 and the paddle region 1328 in this embodiment, however other embodiments contemplate different proportions. The profile of the leading edge 1315 and the trailing edge 1312 along the proximal zone 1324 can be essentially flat or slightly concave as depicted in FIG. 16B of the present embodiment. The profile of the leading edge 1315 and the trailing edge 1312 along the paddle zone 1328 is convex with the greatest distance between the leading edge 1315 and the trailing edge 1312 in the paddle zone central region 1329. In the present embodiment, the leading edge 1315 is symmetric with the trailing edge 1312. In other words, a proximal region distance 1340 (shown by the double arrow) is defined between the leading edge 1315 and the trailing edge 1312 in the proximal zone/region 1324, which is smaller than a peak paddle region distance 1344, defined between the leading edge 1315 and the trailing edge 1312 in the paddle zone/region 1328. In certain embodiments, the distance between the leading edge 1315 and the trailing edge 1312 at any point along the paddle region 1328 is greater than any point along the proximal region 1324. The leading edge 1315 depicts a flat 1360A (which in 2-D is an uninterrupted linear extension 1360) extending from the contact surface 1322 to the distal tip 1314. The shaft 1310 terminates at a dome-shaped cap 1313, which gradually and smoothly transitions from the paddle zone 1328 to ease penetration of the shaft 1310 into a vaginally or anal orifice/cavity. Here, the dome-shaped cap 1313 consistently tapers from the paddle zone 1328 to the distal tip 1314.

A longitudinal slot 1320, which is in communication with the receiving port 201 via a passageway 1225 (of FIG. 13B), is located along the shaft 1310 in the shaft side 1325 between the leading edge 1315 and the trailing edge 1312. In the present embodiment the longitudinal slot 1320 is essentially equidistant between the leading edge 1315 and the trailing edge 1312 and mostly resides in the paddle region 1328 but partially in the proximal region 1324, as shown. Also in the present embodiment, the shaft outer surface 1303 eases into the longitudinal slot 1320 via an upper and lower radius 1309. In this embodiment, a proximal radius 1309*a* is flared towards the stop plate 1308 and is a different shape than distal radius 1309*b* (the radiuses 1309*a* and 1309*b* are subsets of the generic radius 1309). The upper and lower radius 1309 are symmetric in this embodiment. There are diametrically opposing slots 1320 in this medicinal applicator 1350, however, other embodiments envision a single slot in one of the shaft sides 1325.

Figure 16C:
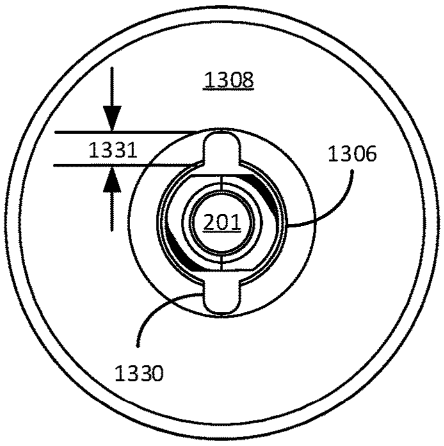
FIG. 16C is a line drawing of medicinal applicator embodiment as viewed from the base showing the medicinal cream receiving port concentrically located therein.

FIG. 16C is a line drawing of medicinal applicator embodiment 1350 as viewed from the base 1306 showing the medicinal cream receiving port 201 concentrically located therein. The protruding ribs 1330 are diametrically opposed and in some commercial embodiments protrude from the base 1306 with a dimension 1331 between 0.128 and 0.25 inches.

FIG. 17A is a top view line drawing of the medicinal applicator 1350 consistent with embodiments of the present invention. As shown, the shaft 1310 is a constant diameter 1333 as measured between the two shaft sides 1325*a* and 1325*b* except for a slight shaft side indent 1338 at the flared end of the longitudinal slot radius 1309*a* (1325*a* and 1325*b* are subsets of the generic side 1325). The medicinal applicator 1350 depicts a tangent or uninterrupted linear extension (flat) 1360A (which is an in that runs along the length of the leading edge 1315). The dome-shaped cap 1313 is depicted consistently tapering (rounded) from the paddle zone 1328 to the distal tip 1314. The base 1306 has a diameter 1305 that in certain embodiments is between 0.5 and 0.75 inches in diameter. The male threaded post 1302 is to the left of the base 1306, which at the proximal end defines where the medicinal cream receiving port 201 is located.

FIGS. 17B and 17C are line drawings of cross-sections of the shaft 1310 at the corresponding cross-section cut lines FF and GG of FIG. 17A consistent with embodiments of the present invention. FIG. 17B is a cross-section of the shaft 1310 at cut-line section FF in the proximal zone 1324. The cross-sectional shaft shape is essentially that of a square with rounded edges 1362, which in this embodiment are radiuses. The rounded edges 1362 come together in uninterrupted linear extensions 1360 but could optionally come together in arcs. Certain embodiments envision the medicinal cream passageway 1225 being about 0.095 inches in diameter. Some embodiments contemplate the shaft 1310 in this proximal zone 1324 being circular. The stop plate 1308 and the stop plate radius 1307 are shown here behind the cross-section of the shaft 1310 in the proximal zone 1324.

FIG. 17C is a cross-section of the shaft 1310 at cut-line section GG. The cross-sectional shaft shape is essentially that of a rectangle with rounded edges 1362, which in this embodiment are radiuses. The rounded edges 1362 come together in uninterrupted linear extensions 1360 but can optionally come together in arcs 1363. Certain embodiments envision the medicinal cream passageway 1225*b* being larger in diameter at the elongated slot 1320, as described in more detail in conjunction with FIG. 12B. The stop plate 1308 is shown behind the cross-section of the shaft 1310 in the paddle zone 1328. The cross-sectional shape of the shaft 1310 in the paddle zone 1328 is oblong shaped, which is defined herein is an object having an elongated 2-D shape such as a rounded rectangle or oval or a racetrack that is essentially a circle that has been stretched with linear sides and circular ends. As further defined herein, protrusions or features extending from either an elongated shape (e.g. an elongated rectangle, rounded cornered elongated rectangle, or elongated circle) or a non-elongated shape (e.g., square, a rounded square, circle, etc. that is elongated in one dimension) do not in themselves define and oblong shape. In other words, a square or circle with protrusions extending from opposite sides (i.e., a flat side with a bump or mound extending from a portion of a flat side) does not meet the definition of oblong as used herein. This particular oblong shaped cross-section in the paddle zone is rectangular shaped with rounded corners 1362. The elongated slots 1320 are in communication with the medicinal cream passageway 1225*b* via exit aperture channels 1221. The elongated slots 1320 transition to the shaft side 1325 via slot rounds 1309, which in certain embodiments are radiuses.

Figure 18A:
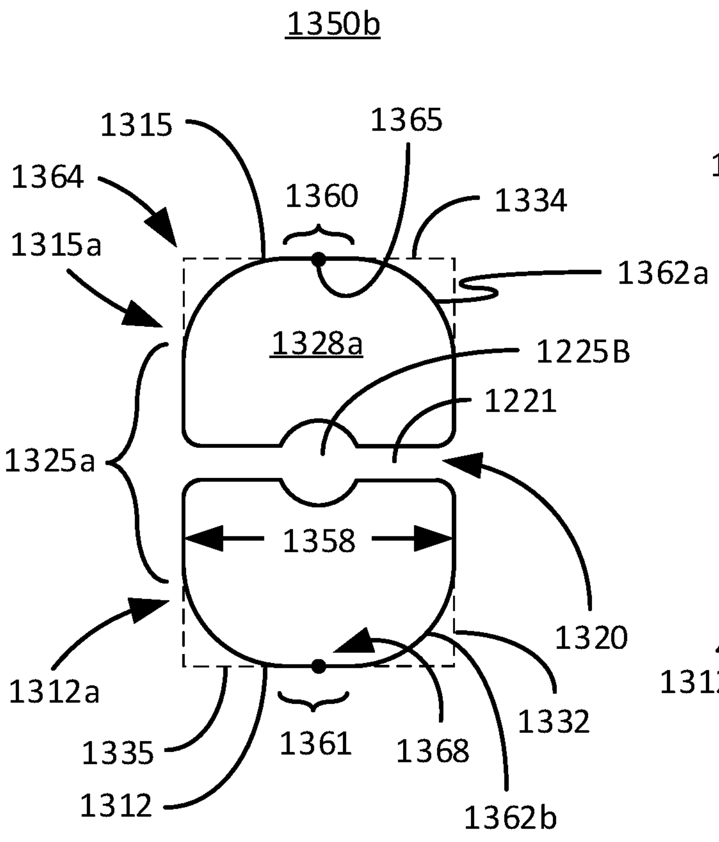
FIGS. 18A and 18B are line drawings of different cross-sectional paddle zone embodiments of the shaft consistent with embodiments of the present invention.
Figure 18B:
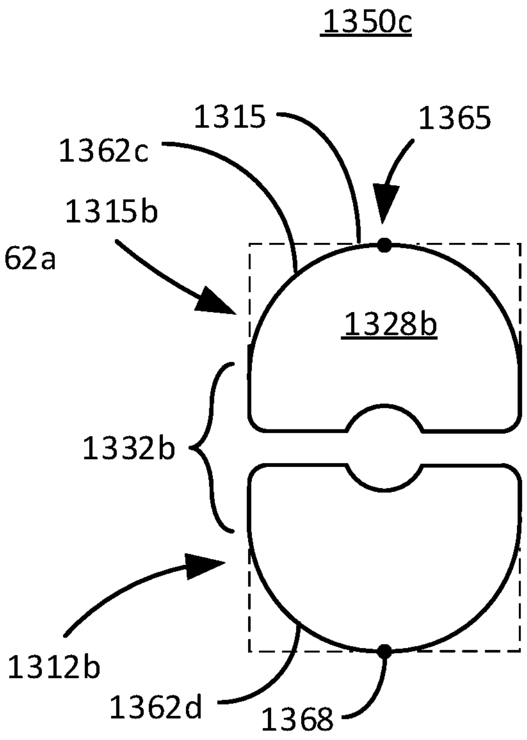

FIGS. 18A and 18B are line drawings of different cross-sectional paddle zone embodiments of the shaft 1310 consistent with embodiments of the present invention. FIG. 18A is an embodiment of the paddle zone 1328*a* (which is a variation of a generic paddle zone 1328) in a medicinal applicator 1350*b*. As shown, the overall shape is an oblong rounded cornered rectangle with slots 320 in the sides 1325*a*, wherein the distance between the leading edge 1315 and the trailing edge 1312 is larger than the side-to-side distance 1358. More specifically, the oblong shaped cross-section of the paddle zone 1328*a* tracks or otherwise stays in the boundary of a rectangle 1332 (shown by the dashed lines) with the upper apex 1365 of the rectangle top 1334 defining the leading edge 1315 and the lower apex 1368 of the rectangle bottom 1335 defining the trailing edge 1312. As shown by the solid curves at the triangle corners 1364, the oblong shaped paddle zone cross-section has upper rounded corners 1362*a* and lower rounded corners 1362*b*. The rounded corners 1362*a* and 1362*b* can be radiuses or some other shaped rounded corner. With detail to the shaft leading edge portion 1315*a* between the exit aperture channel 1221 and the upper shaft apex 1365, the upper rounded corners 1362*a* extend from rectangle sides 1325*a*, which in this embodiment tracks to a straight vertical line only interrupted by the longitudinal slot 1320. The upper rounded corners 1362*a* meet along the leading edge 1315 via an uninterrupted upper uninterrupted linear extension 1360. The upper linear extension 1360 is uninterrupted because there is nothing extending beyond the leading edge 1315 defined by the linear extension 1360 of the two upper rounds 1362*a*. The flat 1360A, as shown in FIG. 16A, is an infinitesimal sum of straight lines (uninterrupted linear extensions) between the rounded corners 1362*a* that essentially form a ribbon along the leading edge 1315 and trailing edge 1312 length 1351. The ribbon/flat 1360A is envisioned to improve spreading medicinal cream 710 on the contact surface of an anal or vaginal wall defined at the interior of the respective cavity. The sides 1325*a* essentially define a side tangent between a corresponding upper round 1362*a* and lower round 1362*b*, as shown. The shaft trailing edge portion 1312*a* between the exit aperture channel 1221 and the lower shaft apex 1368 is symmetric with the shaft leading edge portion 1315*a*. Accordingly, the lower rounded corners 1362*b* meet along the trailing edge 1312 via an uninterrupted lower tangent 1361.

FIG. 18B is yet a different embodiment of a paddle zone 1328*b* in a medicinal applicator 1350*c*, consistent with embodiments of the present invention. As shown, the overall shape is another oblong rounded cornered rectangle with slots 1320 in the paddle sides 1325. In this configuration, the upper rounded corners 1362*c* meet at the upper apex 1365 wherein there is essentially no tangent, or optionally wherein the tangent is infinitesimally small. Likewise, the lower rounded corners 1362*d* meet at the lower apex 1368 with essentially no tangent. The oblong shaped cross-section is shaped like a racetrack. The leading edge portion 1315*b* is symmetric with the trailing edge portion 1312*b*.

Figure 19:
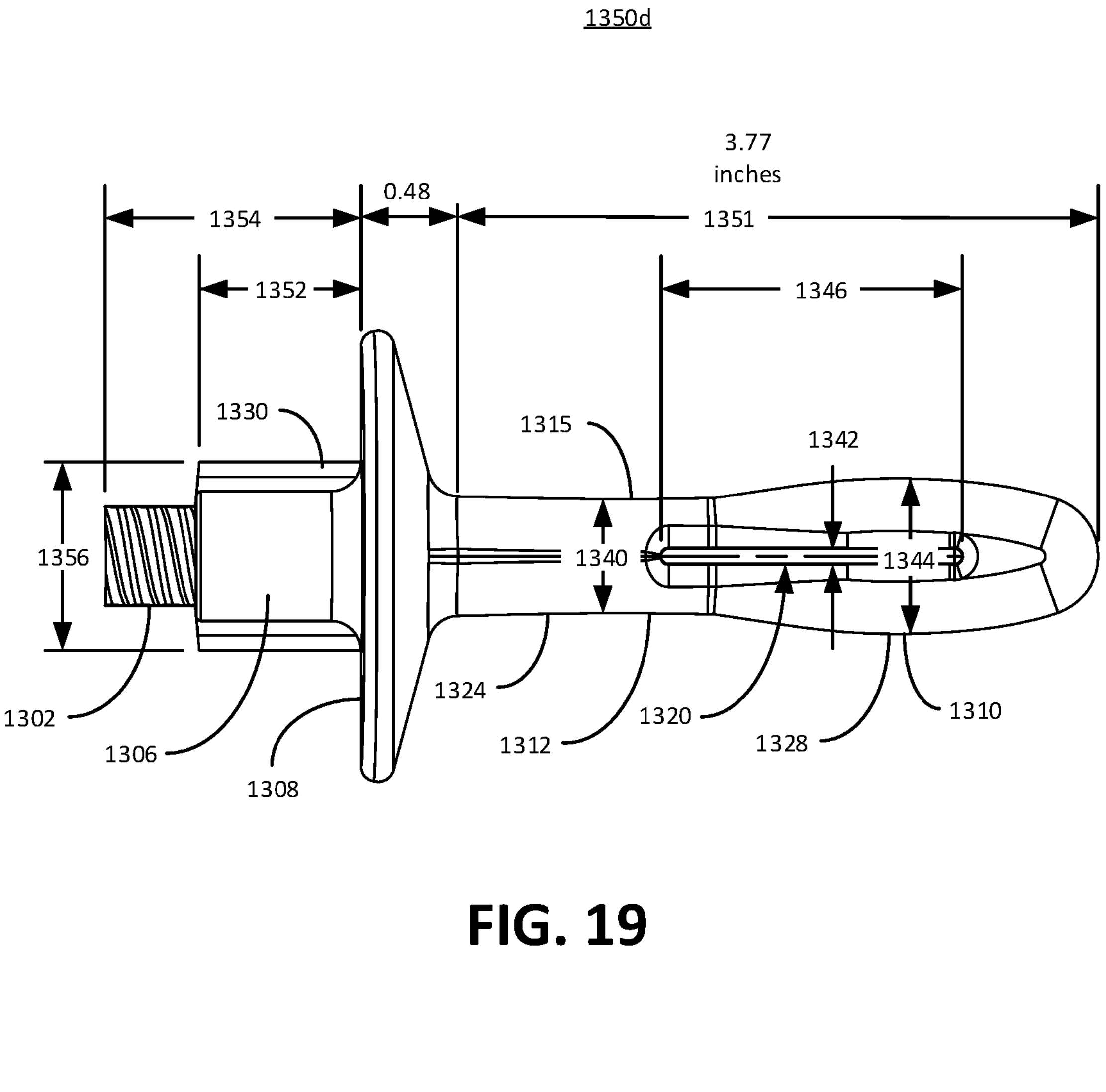
FIG. 19 depicts a commercial embodiment of a medicinal applicator with some measurements consistent with embodiments of the present invention.

FIG. 19 depicts a commercial embodiment of a medicinal applicator 1350*d* with some measurements consistent with embodiments of the present invention. Here, the largest paddle zone dimension 1344 defined by the leading edge 1315 to the trailing edge 1312 of the paddle zone 1328 is 0.815 inches. The largest proximal zone dimension 1340 is 0.598 inches as defined from the leading edge 1315 to the trailing edge 1312, which is always smaller than the smallest paddle zone dimension from the leading edge 1315 to the trailing edge 1312. The longitudinal slot width 1342 is 079 inches wide and the longitudinal slot length 1346 is 1.575 inches long. The shaft length 1351 is 3.77 inches long, the stop plate 1308 is 0.48 inches from the base 1306 to the shaft 1310, the base 1306 is 0.845 inches long and from the proximal end of the male threaded post 1302 to the stop plate 1308 is 1.337 inches long. The base 1306 including the protruding ribs 1330 is 0.988 inches across. Of course, these measurements can vary and will typically have normal mechanical tolerances, such as +/−0.005 inches for example.

Figure 20A:
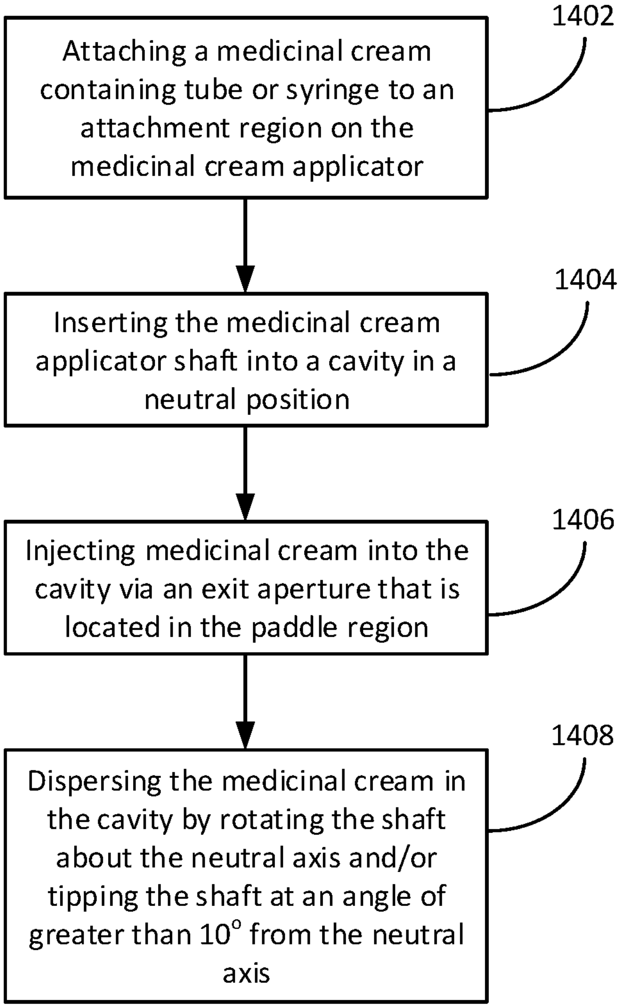
FIG. 20A is a block diagram flowchart of a method for applying medicinal cream to a human cavity consistent with embodiments of the present invention.
Figure 20B:
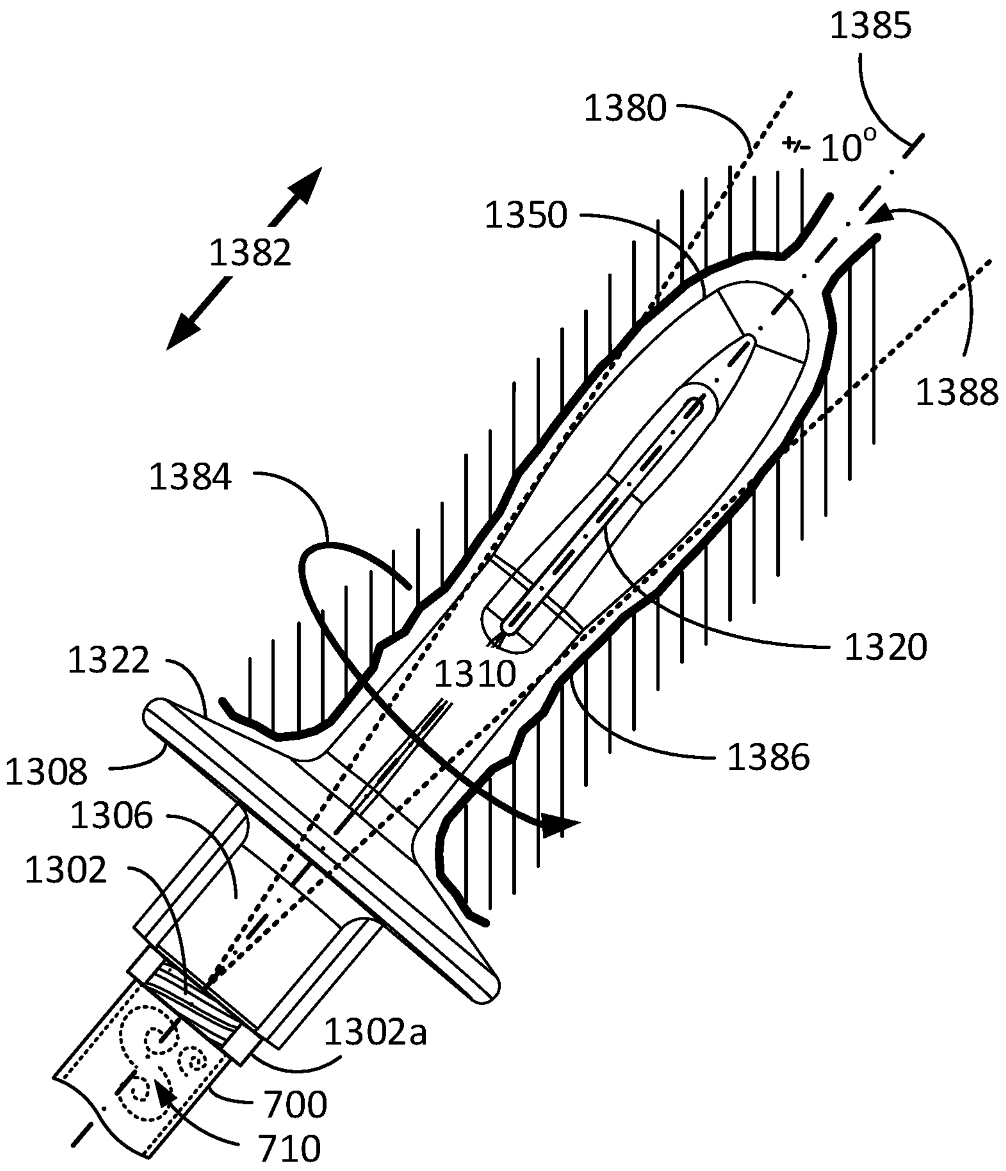
FIG. 20B is a line drawing of a medicinal applicator inserted in a human cavity.

FIG. 20A is a block diagram flowchart of a method for applying medicinal cream to a human cavity consistent with embodiments of the present invention. FIG. 20A is presented in view of FIG. 20B, which is a line drawing of a medicinal applicator 1350 inserted in a human cavity 1388. In step 1402, the medicinal cream applicator 1350 is attached to a syringe 700 containing medicinal cream 710 via the male threaded post 1302 that is screwed into the female threaded receiving cuff 1302*a*. When the medicinal applicator 1350 is inserted into a human cavity 1388 (or optionally an animal cavity), the medicinal applicator 1350 positions itself in a low energy placement inside of the cavity 1388, which defines a neutral axis 1385, step 1404. In other words, the cavity walls 1386 close in around the outside of the shaft 1310 to define the neutral axis 1385 when the medicinal applicator 1350 is devoid of any force other than the cavity walls 1386. When the medicinal applicator 1350 is neutrally located in the cavity 1388 (i.e., its natural position uninfluenced by forces other than the cavity wall 1386), the neutral axis 1385 aligns with the shaft axis 217 shown in FIG. 16B. With the medicinal applicator 1350 inserted in the cavity 1388, medicinal cream 710 is squirted through the medicinal applicator passageway 1225 (of FIG. 12B) and out through the longitudinal slots 1320, step 1406. The next step 1408 is a step for dispersing the medicinal cream 710 on the cavity wall 1386 by rotating the shaft 1310 about the shaft axis 217 as shown by the curved arrow 1384. The shaft 1310 can be rotated 1384 either clockwise or counterclockwise. The medicinal cream 710 is more effectively dispersed on the cavity wall 1386 via the oblong cross-sectional shaped paddle region 1328. Some embodiments envision the medicinal cream 710 even more effectively dispersed on the cavity wall 1386 via the ribbon/flat along the leading edge 1315 and the trailing edge 1312 (see FIG. 16A) defined by the tangents (uninterrupted linear extensions) 1360 and 1361 of FIG. 18A. In the present embodiment, the shaft 1310 is envisioned to be rotated by a person gripping the base 1306 either when self-applying the medication or one applying the medication to another person. The medication 710 is envisioned to be further applied to the cavity wall 1386 by tipping the shaft 1310 at least +/−10° off the neutral axis 1385, as shown by the dashed angled lines 1380. When the medicinal applicator shaft 1310 is tipped 10°, the shaft axis 217 aligns with the dashed lines 1380. The tipping motion is envisioned to help spread the medicinal cream 710 into any crypts or nonconformities in the cavity wall 1386. The medicinal cream application motion can further be augmented by moving the medicinal applicator shaft 1310 in an insertion/withdrawal direction shown by the double arrow 1382.

Figure 21A:
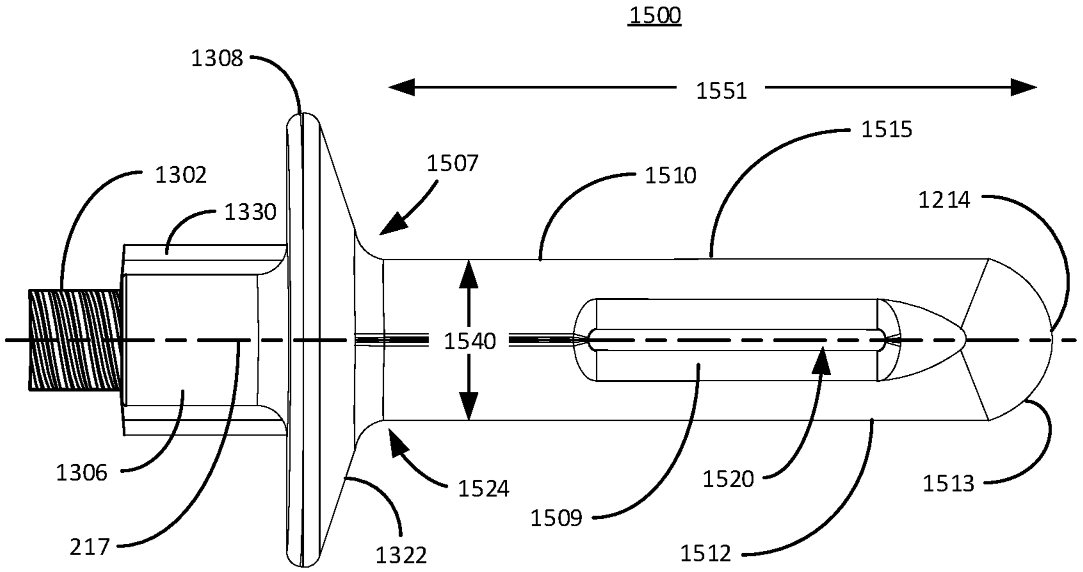
FIGS. 21A and 21B are line drawings of a side view and top view of an oblong shaped medicinal applicator shaft embodiment consistent with embodiments of the present invention.

FIG. 21A is a side view line drawing of still another embodiment of a medicinal applicator consistent with embodiments of the present invention. The medicinal applicator 1500 is similar to the medicinal applicator 1350 (of FIG. 16B) but with essentially a constant leading-edge-to-trailing-edge distance 1540 along the majority of the shaft length 1551. The majority of the shaft length 1551 is defined as at least 60% of the shaft length and preferably at least 75% of the shaft length 1551. The term "leading-edge-to-trailing-edge distance 1540" means within the normal tolerances of engineering, which is envisioned to be as much as +/−3% variation but likely less than 1% variation.

As depicted, the medicinal applicator 1500 generally comprises a handle 1306 that is separated from the shaft 1510 by a stop plate 1308. A medicinal cream receiving port 210 is located at the proximal end of the base 1306. Here, the base 1306 includes a male threaded post 1302 that is configured to matingly engage or otherwise screw into an opposing female threaded connector on a syringe 700 (of FIG. 7A) or optionally a tube/bag dispenser 755 (of FIG. 7B). The base 1306 further comprises diametrically opposed protruding ribs 1330 that can be used as 'grips' to twist the shaft 1510 either clockwise or counterclockwise when inserted in a vaginal cavity or simply cavity (simply considered a cavity). The protruding ribs 1330 extend from the threaded post 1302 to the stop plate 1308. In the present embodiment, the stop plate 1308 is circular with a tapered contact surface 1322 that is in contact with a human body just outside of the orifice/cavity when the medicinal applicator 1500 is inserted in a cavity. The contact surface 1322 tapers into the shaft proximal region 1524 via a stop plate radius 1507, which may or may not be a constant radial arc.

The shaft extends along the shaft axis 217 from the base 1306 to the distal end 1214. The base 1306 is separated from the shaft 1510 by way of the stop plate 1308. The shaft leading edge 1510 extends in a straight line from the stop plate 1308 to the dome-shaped cap 1513 located at the applicator distal end 1214. The shaft trailing edge 1512 is symmetric with the shaft leading edge 1510 in that it also extends in a straight line from the stop plate 1308 to the applicator distal end 1214. In this embodiment, the diametrically opposed leading edge 1510 and trailing edge 1512 are equidistant from the shaft axis 217.

A longitudinal slot 1520, which is in communication with the receiving port 201 (of FIG. 22A) via a passageway 1225 (of FIG. 21C), is located along the shaft 1510 in the shaft side 1525 between the leading edge 1515 and the trailing edge 1512. In the present embodiment the longitudinal slot 1520 is essentially equidistant between the leading edge 1515 and the trailing edge 1512 and mostly resides in the distal half of the shaft 1510, that is more than 50% of the longitudinal slot 1520 is at the distal half of the shaft 1510. Some embodiments envision at least 75% of the longitudinal slot 1520 residing in the distal half of the shaft 1510 with the remainder of the slot 1520 in the proximal half of the shaft 1510. As further shown, the shaft outer surface 1503 (see FIG. 22B) eases into the longitudinal slot 1520 via an upper and lower radius 1309. The upper and lower radius 1309 are symmetric in this embodiment. There are diametrically opposing slots 1520 in this medicinal applicator 1500 (i.e., on either side), however, other embodiments envision a single slot 1520 in one of the shaft sides 1525.

Figure 21B:
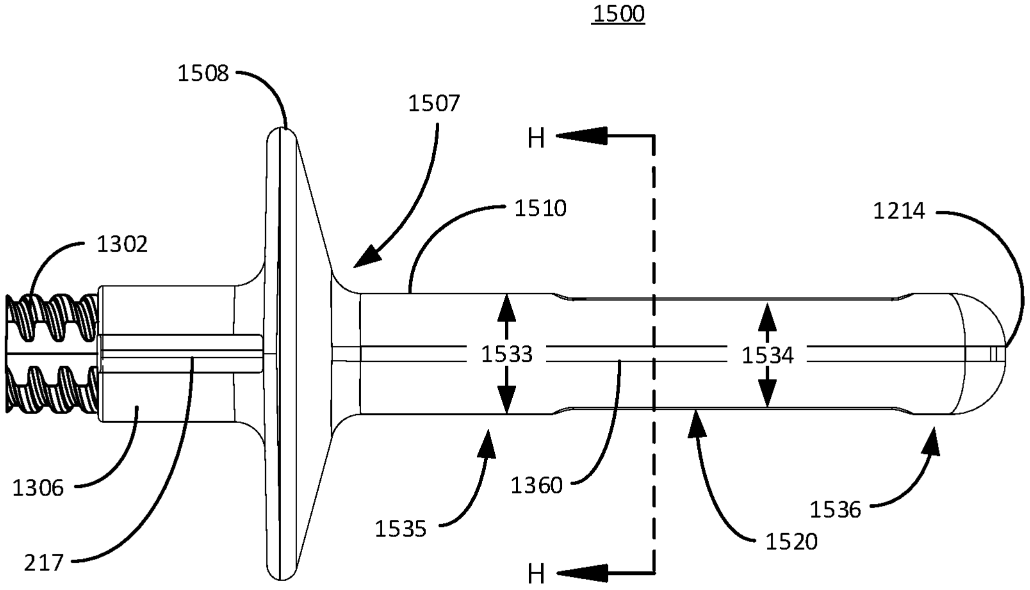

FIG. 21B is a top view line drawing of the medicinal applicator 1500 consistent with embodiments of the present invention. As shown, the shaft 1510 comprises a standard shaft width 1533 at the proximal shaft region 1535 and the distal shaft region 1536 that does not include the longitudinal slot 1520. In this embodiment, the slot region width 1534 at the longitudinal slot 1520 is narrower than the standard shaft width 1533. Other embodiments envision the standard shaft width 1533 being essentially constant along the entire length of the shaft 1310 (including at the longitudinal slot 1520). The medicinal applicator 1500 depicts a flat uninterrupted linear extension 1360 that runs along the leading edge 1515 (and the trailing edge 1513). Certain embodiments envision the dimensions of the medicinal applicator 1500 being within the range (+/−20%) of the medicinal applicator embodiment 1350*d* (described in conjunction with FIG. 19). As further shown, there is a cut-line HH (orthogonal to the shaft axis 217), which is used for reference with FIG. 21C.

Figure 21C:
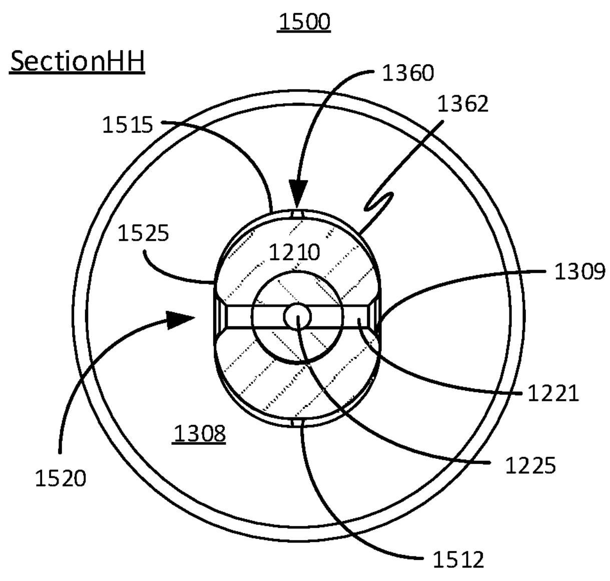
FIG. 21C is a line drawing of a cross-section of the oblong shaft at the corresponding cross-section cut line HH of FIG. 21B consistent with embodiments of the present invention.

FIG. 21C is a cross-section of the shaft 1510 at cut-line section HH. The cross-sectional shaft shape is oblong, which is essentially that of a non-square rectangle with rounded edges 1362. The rounded edges 1362 come together in tangents (uninterrupted linear extensions) 1360 but can optionally come together in arcs 1363. This is depicted more completely in FIGS. 18A and 18B, which are examples of cross-sectional oblong shapes. Certain embodiments envision the medicinal cream passageway 1225*b* being larger in diameter at the elongated slot 1520, as described in more detail in conjunction with FIG. 12B. The stop plate 1308 is shown behind the cross-section of the shaft 1510 at the cross-section HH. As previously discussed, the cross-sectional shape of the shaft 1510 is oblong shaped, which is defined herein is an object having an elongated shape such as a rounded rectangle or oval or a racetrack that is essentially a circle that has been stretched with linear sides and circular ends. As further defined herein, protrusions or features extending from an elongated shape (e.g., square, a rounded square, circle, etc., that is elongated in one dimension) do not in themselves define and oblong shape. This particular oblong shaped cross-section along the shaft 15 can is rectangular shaped with rounded corners 1362. The elongated slots 1520 are in communication with the medicinal cream passageway 1225 via exit aperture channels 1221. The elongated slots 1520 transition to the shaft side 1525 via slot rounds 1309, which in certain embodiments are radiuses. As should be appreciated, the leading edge 1515 and trailing edge 1512 of the oblong shaped shaft 1510 improves spreading medicinal cream 710 (that is dispensed through the longitudinal slots 1520) on the cavity walls 1386 when rotated 1384 about the axis 217, which is generally described in more detail in conjunction with FIG. 20B.

Figure 22A:
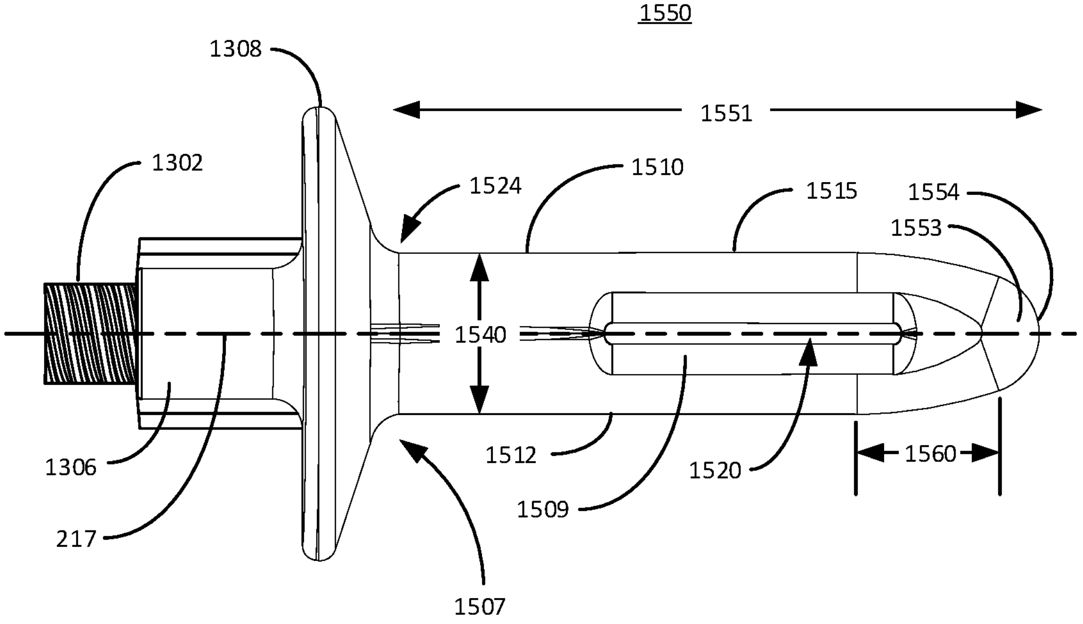
FIGS. 22A and 22B are line drawings of yet another embodiment of the oblong shaped medicinal applicator shaft with a distal end taper consistent with embodiments of the present invention.

FIG. 22A is a side view line drawing of a uniform oblong shaped shaft embodiment that is a variation of the medicinal applicator shaft 1510 shown in FIG. 21A. As shown, the medicinal applicator embodiment 1550 comprises the uniform shaft 1510 of medicinal applicator 1500 but with a distal tapered region 1560 leading into the dome-shaped cap 1553. More specifically, the oblong shaped shaft 1510 has essentially a uniform oblong shaped cross-section (as described for the shaft 1510 of medicinal applicator 1500) from the proximal shaft location 1524 to where the distal tapered region 1560 begins. The dome-shaped cap 1553 is a smaller dome-shaped cap then cap 1513 the medicinal applicator embodiment 1500 to facilitate easier penetration into the anal or vaginal cavity. The distal tapered region 1560 gently transitions from the oblong shaped shaft 1510 to the smaller dome-shaped cap 1553, as shown.

Figure 22B:
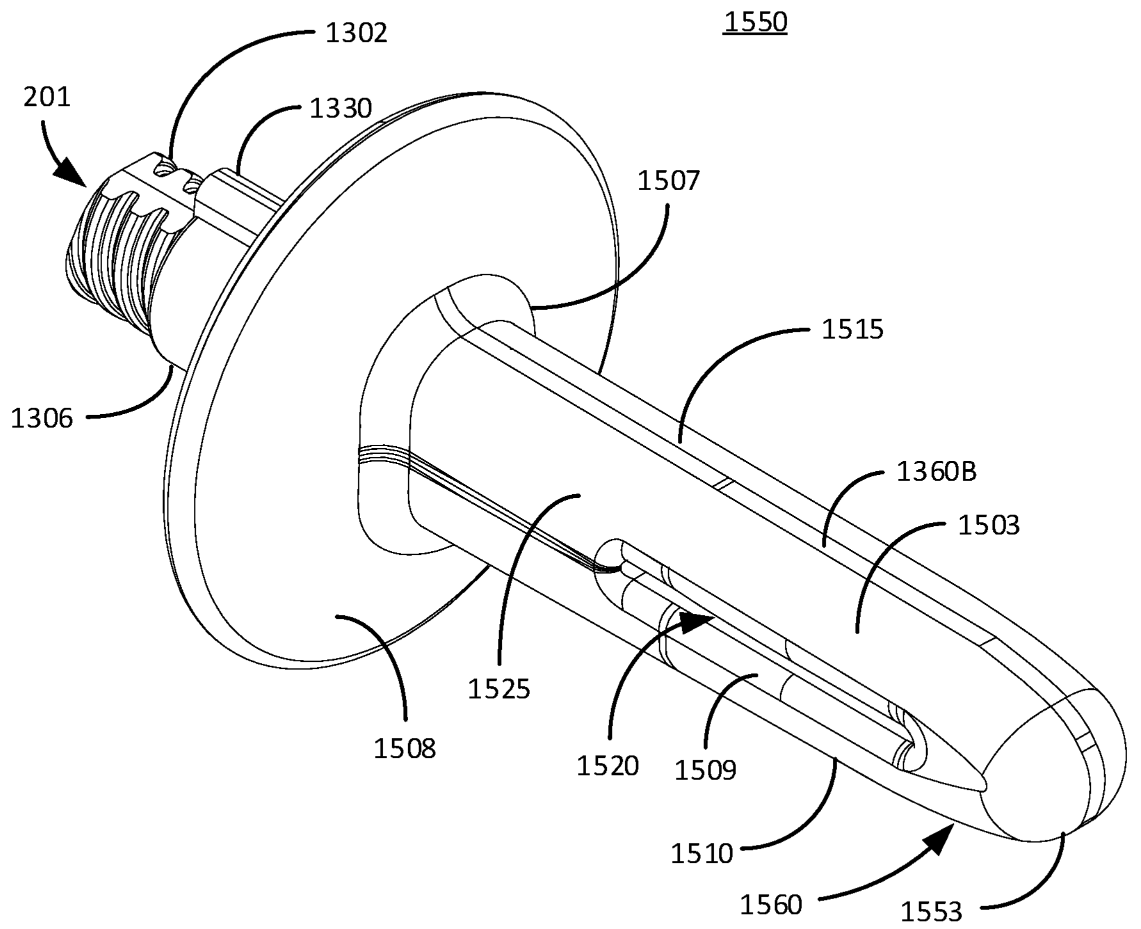

FIG. 22B is a line drawing of a front isometric line drawing of the medicinal applicator 1550 with the uniform oblong shaped shaft 1510 transitioning into a distal tapered region 1560 consistent with embodiments of the present invention. As shown, the upper uninterrupted linear extension 1360 resides along the shaft leading edge 1515. Also, though not shown is a lower tangent that resides along the shaft trailing edge 1512. In the present embodiment the oblong shaped shaft 1510 is symmetric about the axis 207 on either side of the longitudinal slot 1520.

With the present description in mind, below are some examples of certain embodiments illustratively complementing some of the methods and apparatus embodiments discussed above and presented in the figures to aid the reader. Accordingly, the elements called out below are provided by example to assist in the understanding of the present invention and should not be considered limiting. The reader will appreciate that the below elements and configurations can be interchangeable within the scope and spirit of the present invention. The illustrative embodiments can include elements from all the figures with a primary focus being directed to FIGS. 16A-22B.

In that light, certain embodiments contemplate a medicinal applicator 1350 comprising: a base 1306 with a medicinal cream receiving port 201 in the base 1306, a shaft 1310 extending along a shaft axis 217 from the base 1306 to a proximal region 1324 that is closer to the base 1306 than a paddle region 1328. The shaft 1310 terminating at an applicator tip 1314. A paddle region cross-section G-G in the paddle region 1328 defines essentially a rectangle 1364 with upper rounded corners 1362 that extend from rectangle sides 1332 and connect at the leading edge 1315 (rectangle top 1334) via an uninterrupted linear extension 1360. By essentially, it is meant that the paddle region cross-section G-G is more or less a rectangle with possible deviation of a +/−5% difference between the width of the rectangle 1332 the leading edge 1315 and the trailing edge 1312. The rectangle 1332 has lower rounded corners 1366 that extend from the rectangle sides 1325 and connect at the trailing edge 1312 (rectangle bottom 1335) via an uninterrupted lower tangent 1361. The upper uninterrupted linear extension 1360 resides along a shaft leading edge 1315 and the lower tangent 1361 resides along a shaft trailing edge 1312. At least one exit aperture 1320 is located in one of the rectangle sides 1332. An unobstructed pathway 1225 is in communication with the receiving port 201 and the exit aperture 1320, and in some embodiments is in the center of the shaft 1310 along the shaft axis 217. A proximal region distance 1340 defined from the shaft leading edge 1315 to the shaft trailing edge 1312 in the proximal region 1324 is smaller than a paddle region distance 1344 defined from the shaft leading edge 1315 to the shaft trailing edge 1312 in the paddle region 1328.

Optionally the medicinal applicator 1350 can be wherein the upper and the lower rounded corners 1362 and 1366 are a constant radius.

The medicinal applicator embodiment 1350 is further envisioned wherein the upper uninterrupted linear extension 1360 and the lower tangent 1361 are infinitesimally small with the upper and the lower rounded corners 1362 and 1366 directly in contact. In this embodiment, the upper rounded corners 1362 can meet at a leading edge apex 1365 and the lower rounded corners 1366 meet at a trailing edge apex 1368.

The medicinal applicator embodiment 1350 is further imagined wherein the uninterrupted linear extensions 1360 and 1362 are straight lines.

The medicinal applicator embodiment 1350 is further considered wherein the upper uninterrupted linear extension 1360 is parallel to the lower tangent 1361.

It is further pondered that the shaft of the medicinal applicator embodiment 1350 is between 3.0-4.0 inches long, the proximal region 1324 is between 1.0-1.6 inches long, the paddle region 1328 is between 1.4-3.0 inches long, the proximal region distance 1340 is less than 0.75 inches long and the distal region distance 1344 is less than 1.5 inches long.

The medicinal applicator embodiment 1350 is further considered contemplated wherein the paddle region 1328 is in the second half of the shaft 1310 and the proximal region 1324 is in the first half of the shaft 1310.

It is further envisioned that the shaft of the medicinal applicator embodiment 1350 has rectangle sides 1332 that are essentially separated by a constant distance in the proximal region 1324 and the paddle region 1328.

The medicinal applicator embodiment 1350 is further envisions the shaft 1310 extending to a dome-shaped applicator cap 1313 that terminates in the tip 1314.

The medicinal applicator embodiment 1350 is further imagined wherein the proximal zone 1324 defines a circular cross-section at F-F, and the paddle region cross-section G-G defines an oblong shape.

It is further envisioned that the at least one exit aperture 1320 of the medicinal applicator embodiment 1350 is an elongated slot located in the paddle zone 1328.

The medicinal applicator embodiment 1350 can further be wherein there are two exit apertures 1320 that are diametrically opposed.

Yet another embodiment of the present invention envisions an applicator 1350 for medicinal cream comprising: a rectal/vaginal shaft 1310 separated from a handle 1306 via a stop plate 1308. Here, a shaft axis 217 extends through the center of the handle 1306 to a distal end 1314 of the shaft 1310. The shaft 1310 defined by a leading edge 1315 diametrically opposed to a trailing edge 1312, wherein the leading edge 1315 is closer to the trailing edge 1312 in a shaft proximal region 1324 than in a shaft paddle region 1328. The shaft proximal region 1324 is closer to the stop plate 1308 than the shaft paddle region 1328. An unobstructed pathway 1225 is in communication with a receiving port 201 in the handle 1306 and an exit aperture 1320 in the shaft 1310, which in certain embodiments is an elongated shaft. A proximal shaft region 1324 and a paddle region 1328 define the leading edge 1315. The shaft paddle region 1324 is closer to the distal end 1314 than the proximal shaft region 1324. The proximal shaft region 1324 is a shorter distance to the shaft axis 217 than a central point 1326 along the paddle region 1328. A cross-section of the shaft 1310 at the central point 1326 is oblong shaped.

The applicator 1350 embodiment for medicinal cream 710 as viewed in addition to FIG. 12D is imagined to further comprise an inner shaft 1216 that is essentially cylindrically shaped, wherein the inner shaft 1216 extends from the stop plate 1308 towards the distal end 1314. At least a portion of the inner shaft 1216 is covered by an outer sleeve 1218 that comprises the paddle region 1328. Some embodiments contemplate the outer sleeve 1218 being a lower durometer then the inner shaft 1216. Still other embodiments contemplate the outer sleeve 1218 being a lower durometer then the inner shaft 1216. Optionally, It is further envisioned that the applicator embodiment 1350 for medicinal cream 710 is an elongated slot located in the paddle zone 1328.

The applicator 1350 embodiment for medicinal cream 710 is further contemplated wherein the base 1306 is connected to a syringe 700 that comprises medicinal cream 710 configured to move through the unobstructed pathway 1225 and out of the medicinal applicator 1350 via the exit aperture 1320.

The applicator 1350 embodiment for medicinal cream 710 is further envisioned wherein the unobstructed pathway 1225 includes more than one diameter.

It is further contemplated that the applicator embodiment 1350 for medicinal cream 710 has the trailing edge 1312 essentially identical in shape to the leading edge 1315.

Still yet another embodiment contemplates a method for applying medicinal cream 710. The method can start with providing a medicinal applicator 1350 that includes a shaft 1310 separated from a handle 1306 via a stop plate 1308. A cross-section GG of the shaft paddle region 1328 is oblong shaped. The shaft 1310 is defined by a leading edge 1315 and a trailing edge 1312 that are diametrically opposed. The distance from the leading edge 1315 to the trailing edge 1312 is shorter in a shaft proximal region 1324 than at a shaft paddle region 1328. The shaft proximal region 1324 is closer to the stop plate 1308 than the shaft paddle region 1328. There are shaft paddle region apexes 1365 and 1368 that are defined in the middle of the leading edge 1315 and trailing edge 1312 of the shaft paddle region 1328. The method further includes attaching a tube 755 or syringe 700, that contains medicinal cream 710, to an attachment region 1302 at a proximal end of the handle 1306. The shaft 1310 can be inserted into an anal or a vaginal cavity (cavity) 1388 in a neutral position, which defines a neutral axis 1385. While the medicinal applicator 1350 is in the cavity 1388, injecting medicinal cream 710 via an exit aperture 1320 that is located in the paddle region 1328 between the shaft paddle region apexes 1365 and 1368. The cream 710 that is injected in the cavity 1388 can be dispersed by rotating the shaft 1310 about the neutral axis 1385 and/or tipping (see dashed lines 1380) the shaft 1310 at an angle of greater than 10° from the neutral axis 1385. The shaft can be moved back and forth (see double arrow 1382) and/or clockwise and counter clockwise (see double arrow 1384).

Other embodiments contemplate a medicinal applicator 1200 can comprise a base 206, a medicinal cream receiving port 201 in the base 206, and a shaft 1210 extending along a shaft axis 217 from the base and terminating at an applicator tip 1214. There is at least one exit aperture 1220 located along a portion of the shaft 1210. An unobstructed pathway 1225 is in communication with the receiving port 201 and the exit aperture 1220. There is a stop plate 1208 that extends essentially radially from the base 206 delineating the base 206 from the shaft 1210. The shaft 1210 possesses a shaft outer shape defined by essentially a flat trailing edge 1212 and a shaped leading edge 1215. The shaped leading edge 1215 comprises a narrow diameter proximal zone 1224 that extends along the shaft 1210 from the stop plate 1208 to a gradually increasing diameter transition zone 1226 that extends to a large diameter paddle zone 1228, which terminates into a shaft distal end 1214.

The medicinal applicator embodiment 1200 further contemplating wherein the distal end 1214 is dome-shaped.

The medicinal applicator embodiment 1200 further considering wherein the stop plate 1208 comprises an abutting surface 1222 configured to contact the opening of a human anus or vagina.

The medicinal applicator embodiment 1200 further pondering wherein the narrow diameter proximal zone 1224 comprises a diameter that is between 0.3 inches and 1 inch, and the large diameter paddle zone 1228 comprises a maximum diameter 1238 that is between 0.4 inches and 1.25 inches.

The medicinal applicator embodiment 1200 further imagining wherein the narrow diameter proximal zone 1224 essentially defines a circular cross-section, and the large diameter paddle zone 1228 essentially defines an oblong cross-section.

The medicinal applicator embodiment 1200 further envisioning wherein the exit aperture/s 1220 is/are located in the large diameter paddle zone 1228.

The medicinal applicator embodiment 1200 further contemplating wherein the exit aperture(s) 1220 is an elongated slot 1320.

The medicinal applicator embodiment 1200 further comprising a distal aperture penetrating through approximately the distal end 1214.

The medicinal applicator embodiment 1200 further comprising an inner shaft 1216 that is essentially cylindrically shaped. The inner shaft 1216 can extend from the stop plate 1208 towards the distal end 1214, wherein at least a portion of the inner shaft 1216 is covered by an outer sleeve 1218 that comprises the shaped leading edge 1215. This can further include a removable outer sleeve 1218 that is removable from the inner shaft 1216.

The medicinal applicator embodiment 1200 can further comprise an inner shaft 1216 that is essentially cylindrically shaped, wherein the inner shaft 1216 extends from the stop plate 1208 towards the distal end 1214. The inner shaft 1216 is encapsulated by an outer sleeve 1218. This can further be wherein the outer sleeve 1218 is a lower durometer then the inner shaft 1216. The outer sleeve 1218 can be composed of silicone or related material. Optionally, the base 206 is connected to a syringe, wherein the syringe 700 contains medicinal cream 710 configured to move through the unobstructed pathway 1225 and out of the medicinal applicator 1200 via the exit aperture 1220.

The medicinal applicator embodiment 1200 is envisioned with the shaft 210 possessing a cross sectional shape that is oblong at the paddle zone 1228.

The medicinal applicator embodiment 1200 is imagined with the unobstructed pathway 1225 comprising more than one diameter.

The medicinal applicator embodiment 1200 is optionally imagined with the unobstructed pathway 1225, including at least two different diameters with a smaller diameter at the exit aperture 1220 and a larger diameter at the stop plate 1208.

Yet another embodiment of an applicator for medicinal cream 1200 can comprise a rectal/vaginal shaft 1210 separated from a handle 206 via a stop plate 1208 with a theoretical/conceptual shaft axis 217 defined as extending equidistant through the handle 206 to a distal end 1214 of the shaft 1210. The shaft 1210 being defined by a leading edge 1215 and a trailing edge 1212 and an unobstructed pathway 1225 that is in communication with a receiving port 201 in the handle 206 and an exit aperture 1220 in the shaft 1210. The leading edge 1215 is defined by proximal shaft region 1224 and a paddle shaft region 1228, the paddle shaft region 1228 is closer to the distal end 1214 then the proximal shaft region 1224, the proximal shaft region 1224 is a shorter distance to the shaft axis 217 than the paddle shaft region 1228. A cross-section of the shaft 1210 located in the paddle shaft region 1228 is oblong shaped.

The applicator embodiment for medicinal cream 1200 further pondering wherein the trailing edge 1212 is essentially identical in shape to the leading edge 1215.

In one commercial embodiment of the applicator embodiment for medicinal cream 1200 is further envisioned wherein the trailing edge 1212 deviates less than 0.1 inches from a straight line that starts at the stop plate 1208 to a dome portion of the distal end 1214.

In yet another embodiment of the present invention, a method for using a medicinal applicator 1200 is envisioned comprising: providing a medicinal applicator 200 that includes a rectal/vaginal shaft 1210 separated from a handle 206 via a stop plate 1208, a shaft axis 217 extending equidistant along the handle 206. The rectal/vaginal shaft 1210 is defined by a leading edge 1215 and a trailing edge 1212 with the leading edge 1215 defined by a shaft paddle region 1228 that is further away from the shaft axis 217 than a shaft proximal region 1224. A cross-section of the shaft 1210 in the shaft paddle region 1228 is oblong shaped. The method continues with attaching a tube or syringe, that contains medicinal cream, to an attachment region 1202 at a proximal end of the handle 206. Next, inserting the shaft 1210 into a cavity no further than the stop plate 1208, the cavity is selected from a group consisting of an anal cavity and a vaginal cavity; next, injecting medicinal cream into the cavity via an exit aperture 1220 located in the paddle region 1228. This is followed by dispersing the medicinal cream via the paddle region 1228 in the cavity by rotating the medicinal applicator 1200 in the cavity.

Still, another embodiment of the present invention envisions a medicinal applicator for anal use 200 comprising: a base 206; a medicinal cream receiving port 201 in the base 206; an anal shaft 210 extending along a shaft axis 217 from the base 206 and terminating at an anal tip 204; at least one longitudinal slot 220 extending along a portion of the shaft 210; and an unobstructed pathway 225 defined between and including the receiving port 201 and at least one longitudinal slot 220, an outer profile 254 of the anal shaft 210 does not map to a circular outer profile shape 161, the outer profile 254 defined by an orthogonal cross-section 250 of the shaft 210 at the at least one longitudinal slot 220.

The medicinal applicator for anal use 200 is further considered comprising three longitudinal slots 220.

The medicinal applicator for anal use 200 is envisioned wherein the at least one longitudinal slot 220 is in-line with the shaft axis 217.

The medicinal applicator for anal use 200 is further envisioned comprising a dome-shaped cap 214 at the anal tip 204.

The medicinal applicator for anal use 200 is envisioned wherein the anus abutting stop plate 208 is circular and extends radially from the shaft axis 217 and further wherein the anus abutting stop plate 208 and the base 206 are adapted to remain outside of a human body and the anal shaft 210 is adapted to penetrate inside of the human body via a human anus. The anus abutting stop plate 208 is further envisioned to be adapted to be butt up against a human anus.

The medicinal applicator for anal use 200 is also envisioned wherein the base 206 possesses at least one mechanical feature 218 configured to interface with a medicinal cream dispenser essentially at the receiving port.

The medicinal applicator for anal use 200 is also envisioned wherein the unobstructed pathway 225 is configured to transport a viscous cream 710 from the receiving port 201 and out through the at least one longitudinal slot 220.

The medicinal applicator for anal use 200 is also envisioned wherein the cross-section 250 of the outer surface of the shaft 210 at the longitudinal slot 220 maps to an oblong shape, and further wherein the oblong shape is defined by a major axis 265 and a minor axis 267, the major axis is at least 25% longer than the minor axis.

The medicinal applicator for anal use 200 is also envisioned wherein the anal shaft 210 is between 2 inches and 5 inches long.

The medicinal applicator for anal use 200 is also envisioned wherein the cross-section 526 of the outer surface 524 of the anal shaft 528 at the longitudinal slot maps to a spiral.

The medicinal applicator for anal use 200 is also envisioned wherein the cross-section 508 of the outer surface of the anal shaft 502 at the longitudinal slot maps to a semicircle 502 with a lobe 504.

Further embodiments of the present invention contemplate a method of using an applicator 200, the applicator method comprising: providing an anal medicinal applicator 200 that comprises a base 206 possessing a receiving port 201, an anal shaft 210 extending along an axis 217 from the base 206 to an anal tip 204, a probe tip at the anal tip 204, at least one longitudinal slot 220 extending along a portion of the anal shaft 210, an anus abutting stop plate 208 delineating the base 206 and the anal shaft 210, the anus abutting stop plate 208 extending radially beyond the anal shaft 210, and an unobstructed pathway 225 extending from the receiving port 201 through the anus abutting stop plate 208 and through a portion of the anal shaft 210 to the at least one longitudinal slot 220, and a cross-section outer profile 250 of the anal shaft 210 at the at least one longitudinal slot 220 that does not map to a circular outer profile shape 161; inserting the anal shaft 210 through an anus 820 and into an anal canal 804 only as far as the anus abutting stop plate 208 will allow when the anus abutting stop plate 208 butts up against the anus 820; after the inserting step, dispensing a viscous material 710 (such as medicinal cream) through the receiving port 201 and out through the at least one longitudinal slot 220; and after the inserting step, rotating the anal medicinal applicator 200 about the axis 217.

The applicator method embodiment further contemplates tipping the anal medicinal applicator 200 to force the anal tip 204 away from the axis 217 when applying medicinal cream in the anal canal 804.

The applicator method embodiment further contemplates attaching a syringe 700 to the base 206 to interface the syringe 700 with the receiving port 201, the dispensing step can be accomplished by actuating the syringe 700 containing the viscous material 710.

The applicator method embodiment also contemplates wherein the cross-section outer profile 250 does not map to the circular shape 161 because of at least one lobe 504 protruding from the circular shape 161 and further manipulating the non circular shaped anal medicinal applicator 200 to spread the viscous material 710 into crypts 806 in the anal canal 804 via the lobe 504.

Additional embodiments of the present invention contemplate an applicator 900 for applying medicinal cream in an anal canal comprising: a base 206; a medicinal cream receiving port 201 in the base 206; an anal shaft 910 extending along an axis 217 from the base 206 and terminating at an anal tip 904, the anal tip 904 possessing an anal tip radius 908 that is larger than a shaft radius 912, the shaft radius 912 and the anal tip radius 908 are defined by radii extending orthogonally from the axis 217; at least one longitudinal slot 220 extending along a portion of the anal shaft 210, the receiving port 201, the anal shaft 210 and the at least one longitudinal slot 220 defining an unobstructed pathway 225.

The applicator for applying medicinal cream is further envisioned wherein the shaft radius 912 is non-uniform along the axis 217.

The applicator for applying medicinal cream is further envisioned wherein the anal tip 904 comprises a circular cross-section which can further be where the anal tip 904 is a bulb shape or wherein the anal tip 904 is adapted to physically confine the medicinal cream 710 within a range of an anal canal 804/828 defined between an anus 820 and the anal tip 904 when the anal medicinal applicator 900 is fully deployed in the anal canal 804/828.

An anal medicinal applicator embodiment 200 can comprise: a base 206; a medicinal cream receiving port 201 in the base 206; an anal shaft 210 extending along a shaft axis 217 from the base 206 and terminating at an anal tip 204; at least one longitudinal slot 220 extending along a portion of the anal shaft 210; an unobstructed pathway 225 defined between and including the receiving port 201 and at least one longitudinal slot 220; an anus abutting stop plate 208 extending essentially radially from the anal shaft 210, the anus abutting stop plate 208 delineating the base 206 from the anal shaft 210, the anus abutting stop plate 208 essentially incapable of being pushed into an anal canal 820 when the anus abutting stop plate 208 is pressed normally against the anus 820; and an anal medicine blocking ring 610 that terminates 611 along a lower half 645 of the anal shaft 210, the anal medicine blocking ring 610 comprising a ring radius 662 that is larger than a shaft radius 664.

The anal medicinal applicator embodiment 200 further envisions wherein an outer profile 254 of the anal shaft 210 does not map to a circular outer profile shape 161, the outer profile 254 defined by an orthogonal cross-section 250 of the shaft 210 at the at least one longitudinal slot 220.

The anal medicinal applicator embodiment 200 further envisions wherein there are three longitudinal slots 220 in the anal shaft 210.

The anal medicinal applicator embodiment 200 further envisions wherein the anus abutting stop plate 208 defines an anus contact surface 222, the anal medicine blocking ring 610 is at least one centimeter from the anus contact surface 222, the anus contact surface 222 is adapted to contact the anus 820 when in the anus abutting stop plate 208 is pressed normally against the anus 820. This can be further envisioned wherein the anal medicine blocking ring 610 defines a terminal ring edge 611 at a distal location on the anal medicine blocking ring 610. Which can be further envisioned wherein the anal medicine blocking ring 610 extends from the anus contact surface 222 to the terminal ring edge 611.

The anal medicinal applicator embodiment 200 further envisions wherein the ring radius 662 is configured to prevent backflow of medicinal cream 710 out of the anus when the anal medicinal applicator 200 is deployed in an anal canal 804.

The anal medicinal applicator embodiment 200 further envisions wherein the anal medicine blocking ring 610 has a rounded outer edge 678.

Further embodiments of the present invention contemplate a method of using an anal medicinal applicator 200, the method comprising: providing an anal medicinal applicator 200 that includes a base 206, a medicinal cream receiving port 201 in the base 206, an anal shaft 210 extending along a shaft axis 217 from the base 206 and terminating at an anal tip 204, at least one longitudinal slot 220 extending along a portion of the anal shaft 210, an unobstructed pathway 225 defined between and including the receiving port 201 and at least one longitudinal slot 220, an anus abutting stop plate 208 extending essentially radially from the anal shaft 210, the anus abutting stop plate 208 delineating the base 206 from the anal shaft 210, an anal medicine blocking ring 610 that terminates 611 along a lower half 645 of the anal shaft 210, the anal medicine blocking ring 610 comprising a ring radius 662 that is larger than a shaft radius 664; inserting the anal shaft 210 into an anal canal 804 up to where the anus abutting stop plate 208 butts up against an anus 820; after the inserting step, dispensing a medicinal cream 710 through the receiving port 201 and out through the at least one longitudinal slot 220; the anal medicine blocking ring 610 blocking the dispensed medicinal cream 710 from exiting the anus 820 when the anal medicine blocking ring 610 prep is disposed in the anal canal 804; and after the inserting step, rotating the anal medicinal applicator 200 about the axis 217.

The method embodiment further contemplates when pressing the anus abutting stop plate 208 against the anus 820, the anus abutting stop plate 208 is essentially incapable of being pushed into the anal canal 820 under normal use.

The method embodiment further contemplates further comprising attaching a syringe 702 the base 206 via the receiving port 201, the dispensing step accomplished by actuating the syringe 700 containing the medicinal cream 710.

The method embodiment further contemplates wherein there are three longitudinal slots 220 in the anal shaft 210.

The method embodiment further contemplates the anal medicinal applicator 200 can only be used in the anal canal 804.

The method embodiment further contemplates the anal medicine blocking ring 610 wherein the ring radius 662 is at least one-quarter of a centimeter larger than the shaft radius 664.

The method embodiment further contemplates the anal medicine blocking ring 610 has a rounded outer edge 678.

The method embodiment further contemplates the anal medicine blocking ring 610 extends from the anus abutting stop plate 208 to a terminal ring edge 611 at a distal location on the anal medicinal blocking ring 610.

Other embodiments envision an anal medicinal applicator device embodiment 200 comprising an anal shaft 210 extending along a shaft axis 217 from a handle 206 to an anal tip 204; an unobstructed pathway 225 extending between and including a receiving port 201 in the handle 206 and at least one longitudinal slot 220 in the anal shaft 210; an anus abutting stop plate 208 extending essentially radially from the anal shaft 210, the anus abutting stop plate 208 delineating the handle 206 from the anal shaft 210; and an anal medicine blocking ring 610 that terminates 611 along a lower half 645 of the anal shaft 210, the anal medicine blocking ring 610 comprising a ring radius 662 that is larger than a shaft radius 664.

The anal medicinal applicator device embodiment 200 further envisions the ring radius 662 being at least one-quarter of a centimeter larger than the shaft radius 664.

The anal medicinal applicator device embodiment 200 further envisions the anus abutting stop plate 208 defining an anus contact surface 222, the anal medicine blocking ring 610 is at least one centimeter from the anus contact surface 222, the anus contact surface 222 is adapted to contact the anus 820 when in the anus abutting stop plate 208 is pressed against the anus 820.

The anal medicinal applicator device embodiment 200 further envisions the anal medicine blocking ring 610 extending from the anus abutting stop plate 208 to a terminal ring edge 611 at a distal location on the anal medicinal blocking ring 610.

The above sample embodiments should not be considered limiting to the scope of the invention whatsoever because many more embodiments and variations of embodiments are easily conceived within the teachings, scope and spirit of the instant specification.

An alternate embodiment contemplates a medicinal applicator 1500 (of FIGS. 21A-22B) comprising: a base 1306; a medicinal cream receiving port 201 in the base 1306; a shaft 1510 extending along a shaft axis 217 from the base 206 and terminating at an applicator cap 1513, the shaft 1510 having a cross-section HH that is essentially a rectangle 1334 with upper rounded corners 1362*a* that extend from rectangle sides 1325*a* and the upper rounded corners 1362*a* connect at the leading edge 1515 via an upper uninterrupted linear extension 1360, and lower rounded corners 1362*b* that extend from the rectangle sides 1325*a* and connect at the trailing edge 1512 via an uninterrupted lower tangent 1361, the upper uninterrupted linear extension 1360 resides along a shaft leading edge 1515 and the lower tangent 1361 resides along a shaft trailing edge 1512, the leading edge 1515 is diametrically opposed to the trailing edge 1512; at least one exit aperture 1320 located in one of the rectangle sides 1325; an unobstructed pathway 1225 in communication with the receiving port 201 and the exit aperture 1320.

The medicinal applicator embodiment 1500 further imagining the upper and the lower rounded corners 1362*a* and 1362*b* being a constant radius.

The medicinal applicator embodiment 1500 further imagining the upper uninterrupted linear extension 1360 and the lower tangent 1361 are infinitesimally small with the upper and the lower rounded corners 1362*a* and 1362*b* are directly in contact, and wherein the upper rounded corners 1362*a* meet at a leading edge apex 1365 and the lower rounded corners 1362*b* meet at a trailing edge apex 1368.

The medicinal applicator embodiment 1500 further imagining the uninterrupted linear extension 1360 and 1361 are straight lines. This can further be arranged with the upper uninterrupted linear extension 1360 being parallel to the lower tangent 1361.

The medicinal applicator embodiment 1500 further imagining the shaft 1510 is between 3.0-4.0 inches long.

The medicinal applicator embodiment 1500 can further comprise a baseplate 1308 between the shaft 1510 and the base 1306.

The medicinal applicator embodiment 1500 further envisioning the cross-section HH is essentially uniform along the shaft length from the base 1306 to the applicator cap 1513.

The medicinal applicator embodiment 1500 further imagining the applicator cap 1513 is dome-shaped.

The medicinal applicator embodiment 1500 further considering the cross-section HH is defined by an oblong shape 1350*b* or 1350*c*.

The medicinal applicator embodiment 1500 further pondering the at least one exit aperture 1320 is an elongated slot 1520 located closer to the applicator cap 1513 than the base 1306.

The medicinal applicator embodiment 1500 additionally contemplating two exit apertures 1320, which are diametrically opposed.

Another embodiment of the present invention envisions an applicator 1500 for medicinal cream 710 (of FIGS. 21A-22B) comprising a rectal/vaginal shaft 1510 separated from a handle 1306 via a stop plate 1308. A shaft axis 217 is defined extending through the center of the handle 1306 to a shaft cap 1513 to where the shaft 1510 terminates distally 1514. The shaft 1510 is further defined by a leading edge 1515 diametrically opposed to a trailing edge 1512. The applicator further has an unobstructed pathway 1225 that is in communication with a receiving port 201 in the handle and an exit aperture 1320 in the shaft 1510. In this embodiment, a cross-section HH of the shaft 1510 is oblong shaped (such as 1350*b* or 1350*c*) and the cross-section HH is essentially uniform along the entire length of the shaft 1510.

The applicator 1500 for medicinal cream 710 additionally contemplating the shaft 1510 comprising an outer sleeve 1218 that covers at least a portion of an inner shaft 1216. The outer sleeve 1218 can have a lower durometer then the inner shaft 1216, for example it can be composed of silicone.

The applicator 1500 for medicinal cream 710 additionally contemplating the base 1306 being connected to a syringe 700, wherein the syringe 700 comprises medicinal cream 710 configured to move through the unobstructed pathway 1225 and out of the medicinal applicator 1500 via the exit aperture 1320.

The applicator 1500 for medicinal cream 710 additionally envisioning the unobstructed pathway 1225 including more than one diameter.

The applicator 1500 for medicinal cream 710 further pondering the trailing edge 1512 being essentially identical in shape to the leading edge 1515.

Still another embodiment contemplates a method for applying medicinal cream 710 (of FIGS. 20B-22B). Fundamentally, a medicinal applicator 1500 is provided, which includes a shaft 1510 separated from a handle 1206 via a stop plate 1508 with a cross-section HH of the shaft 1510 being oblong shaped (such as in FIGS. 18A and 18B, cross-sections 1350*b* or 1350*c*). The method includes attaching a tube 756 or syringe 700, that contains medicinal cream 710, to an attachment region 1302 at a proximal end 202 of the handle 1306. Next, the shaft 1510 is inserted into an anal or a vaginal cavity (cavity) 1388 in a neutral position, which defines a neutral axis 1385. When inserted, inject the medicinal cream 710 into the cavity 1388 via an exit aperture 1320 that is located in the shaft 1510. The injected/dispense medicinal cream 710 now in the cavity 1388 is dispersed by rotating 1384 the shaft 1510 about the neutral axis 1385 and/or tipping 1380 the shaft 1510 at an angle of greater than 10° from the neutral axis 1385.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the dispensing slot is linear and extends axially along the length of a shaft other shapes could equally be used while still maintaining substantially the same functionality without departing from the scope and spirit of the present invention. Another example can include providing various other shaped shafts that meet the functionality of spreading medicinal cream in the folds of an anal canal without departing from the scope and spirit of the present invention. Yet another example can include variations of an enlarged dome relative to the shaft diameter within the scope and spirit of the present invention. Another example envisions that a shaft is not limited to being straight (as in FIG. 2D), but may be concave or some other shape so long as the shaft falls within the scope and spirit of the present invention. Still another example envisions a paddle zone central region 1329 being less than 10% of the paddle zone 1328 to being up to 98% of the paddle zone 1328 without departing from the scope and spirit of the present invention. It should be appreciated that elements of various embodiments described herein can be combined in obvious manners by a person skilled in the art that understands the content of the present specification without departing from the scope of the subject matter presented herein. Further, the term "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

What is claimed is:

1. A medicinal applicator comprising:
- a base;
- a medicinal cream receiving port in the base;
- a shaft extending along a shaft axis from the base and terminating at an applicator cap,
- the shaft having a cross-section that is essentially a rectangle with upper rounded corners that extend from rectangle sides and the upper rounded corners connect at a shaft leading edge via an upper uninterrupted linear extension, and
- lower rounded corners that extend from the rectangle sides and connect at a shaft trailing edge via a lower uninterrupted linear extension,
- the upper uninterrupted linear extension resides along the shaft leading edge and the lower uninterrupted linear extension resides along the shaft trailing edge, the shaft leading edge is diametrically opposed to the shaft trailing edge;
- at least one exit aperture located in one of the rectangle sides;
- an unobstructed pathway in communication with the receiving port and the exit aperture.

2. The medicinal applicator of claim 1, wherein the upper and the lower rounded corners are a constant radius.

3. The medicinal applicator of claim 1, wherein the upper uninterrupted linear extension and the lower uninterrupted linear extension are infinitesimally small with the upper and the lower rounded corners are directly in contact, and
- wherein the upper rounded corners meet at a leading edge apex and the lower rounded corners meet at a trailing edge apex.

4. The medicinal applicator of claim 1, wherein the uninterrupted linear extensions are straight lines.

5. The medicinal applicator of claim 4, wherein the upper uninterrupted linear extension is parallel to the lower uninterrupted linear extension.

6. The medicinal applicator of claim 1, wherein the shaft is between 3.0-4.0 inches long.

7. The medicinal applicator of claim 1, further comprising a baseplate between the shaft the base.

8. The medicinal applicator of claim 1, wherein the cross-section is essentially uniform along the shaft length from the base to the applicator cap.

9. The medicinal applicator of claim 1, wherein the applicator cap is dome-shaped.

10. The medicinal applicator of claim 1, wherein the cross-section is defined by an oblong shape.

11. The medicinal applicator of claim 1, wherein the at least one exit aperture is an elongated slot located closer to the applicator cap than the base.

12. The medicinal applicator of claim 1, wherein there are two exit apertures are diametrically opposed.

13. An applicator for medicinal cream comprising:
- a rectal/vaginal shaft separated from a handle via a stop plate;
- a shaft axis extending through the center of the handle to a shaft cap to where the shaft terminates distally,
- the shaft defined by a shaft leading edge diametrically opposed to a shaft trailing edge;
- an unobstructed pathway in communication with a receiving port in the handle and an exit aperture in the shaft;
- a cross-section of the shaft is oblong shaped and the cross-section is essentially uniform along the entire length of the shaft.

14. The applicator for medicinal cream of claim 13, wherein the shaft comprises an outer sleeve that covers at least a portion of an inner shaft.

15. The applicator for medicinal cream of claim 14, wherein the outer sleeve is a lower durometer then the inner shaft.

16. The applicator for medicinal cream of claim 14, wherein the outer sleeve is composed of silicone.

17. The applicator for medicinal cream of claim 13, wherein the handle is connected to a syringe, wherein the syringe comprises a medicinal cream configured to move through the unobstructed pathway and out of the medicinal applicator via the exit aperture.

18. The applicator for medicinal cream of claim 13, wherein the unobstructed pathway includes more than one diameter.

19. The applicator for medicinal cream of claim 13, wherein the shaft trailing edge is essentially identical in shape to the shaft leading edge.

20. A method for applying a medicinal cream, the method comprising:
- providing a medicinal applicator that includes a shaft separated from a handle via a stop plate,
- a cross-section of the shaft is oblong shaped;
- attaching a tube or syringe, that contains the medicinal cream, to an attachment region at a proximal end of the handle;
- inserting the shaft into an anal or a vaginal cavity in a neutral position, which defines a neutral axis;
- injecting the medicinal cream into the cavity via an exit aperture that is located in the shaft; and
- dispersing the medicinal cream injected in the cavity by rotating the shaft about the neutral axis and/or tipping the shaft at an angle of greater than 10° from the neutral axis.

* * * * *